(12) United States Patent
Merriam et al.

(10) Patent No.: US 11,622,680 B1
(45) Date of Patent: Apr. 11, 2023

(54) SYSTEMS AND METHODS FOR AUTOMATED SUBJECTIVE SELF-REFRACTION

(71) Applicant: M. P. Optics, LLC, Buffalo, WY (US)

(72) Inventors: Ryan R. Merriam, Henrico, VA (US); Matthew A. Phares, Plano, TX (US)

(\*) Notice: Subject to any disclaimer, the term of this patent is extended or adjusted under 35 U.S.C. 154(b) by 0 days.

(21) Appl. No.: 15/930,370

(22) Filed: May 12, 2020

Related U.S. Application Data

(63) Continuation-in-part of application No. 15/705,774, filed on Sep. 15, 2017, now Pat. No. 10,674,904.

(51) Int. Cl.
| | |
|---|---|
| *A61B 3/032* | (2006.01) |
| *A61B 3/00* | (2006.01) |
| *A61B 3/028* | (2006.01) |

(52) U.S. Cl.
CPC ............ *A61B 3/032* (2013.01); *A61B 3/005* (2013.01); *A61B 3/0025* (2013.01); *A61B 3/0033* (2013.01); *A61B 3/0075* (2013.01); *A61B 3/0083* (2013.01); *A61B 3/028* (2013.01)

(58) Field of Classification Search
CPC ..... A61B 3/032; A61B 3/0025; A61B 3/0033; A61B 3/005; A61B 3/0075; A61B 3/0083; A61B 3/028

USPC ........................................................ 351/223
See application file for complete search history.

(56) References Cited

U.S. PATENT DOCUMENTS

| | | | |
|---|---|---|---|
| 2003/0053025 A1* | 3/2003 | Turner | A61F 2/16 351/205 |
| 2005/0105044 A1* | 5/2005 | Warden | G01M 11/0235 351/159.08 |
| 2005/0225725 A1* | 10/2005 | Warden | A61B 3/0075 351/200 |
| 2016/0317025 A1* | 11/2016 | Lee | A61B 3/0041 |
| 2018/0263488 A1* | 9/2018 | Pamplona | A61B 3/0041 |
| 2019/0099072 A1* | 4/2019 | Takii | A61B 3/085 |
| 2022/0007934 A1* | 1/2022 | Raymond | A61B 3/102 |

\* cited by examiner

*Primary Examiner* — Mohammed A Hasan

(57) ABSTRACT

Systems and methods for allowing a user with no prior training to receive automated vision measurements without assistance of another individual by using subjective inputs from a user, which may be supplemented by a predictive method. The predictive method comprising artificial intelligence, patient data, user inputs, automated inputs from cameras and the like. The system may make use of a specific algorithm, decision tree, set of instructions, programming instructions, and the like, in order to provide vision measurements. The system combines programming instructions executed by a processor, output devices, input controls, and a plurality of corrective lenses to find a patient or user's vision measurements.

15 Claims, 41 Drawing Sheets

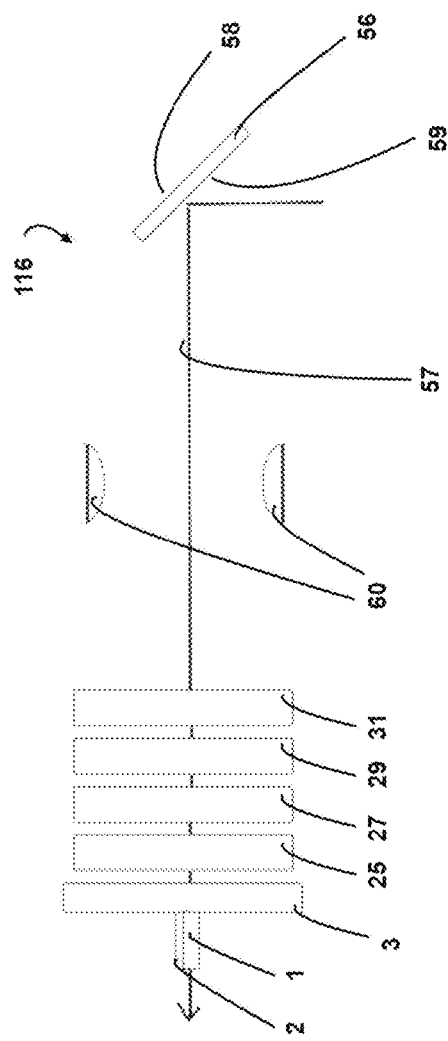
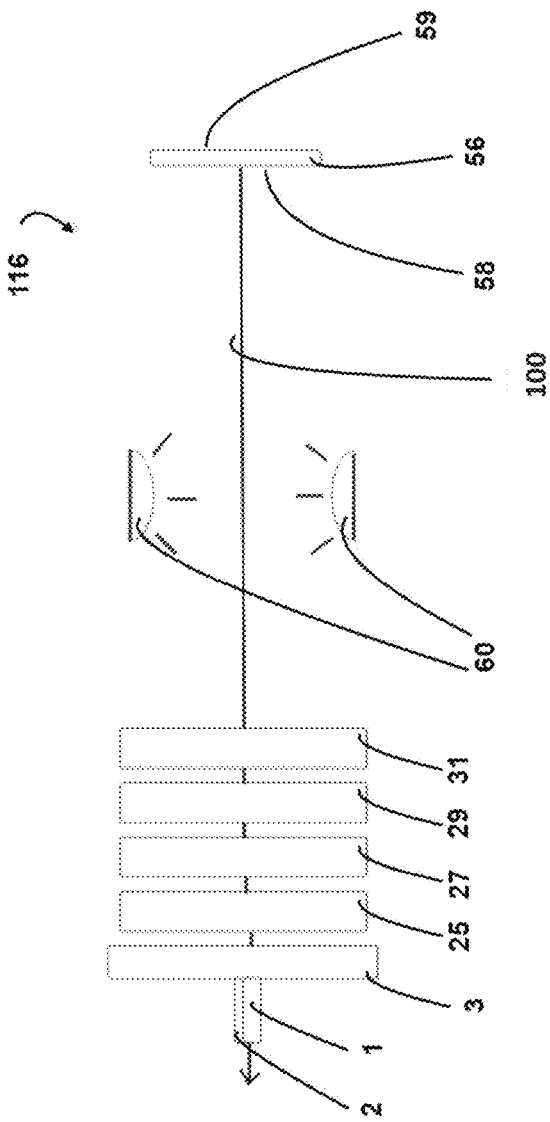

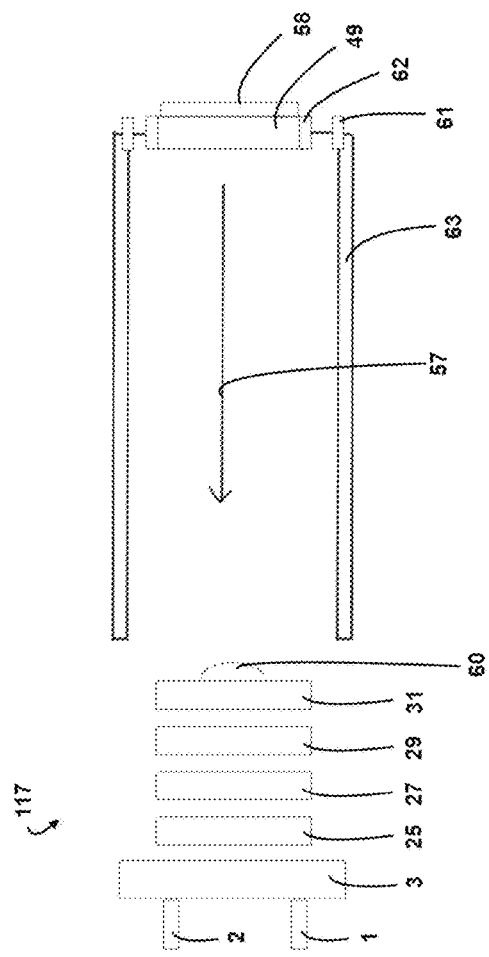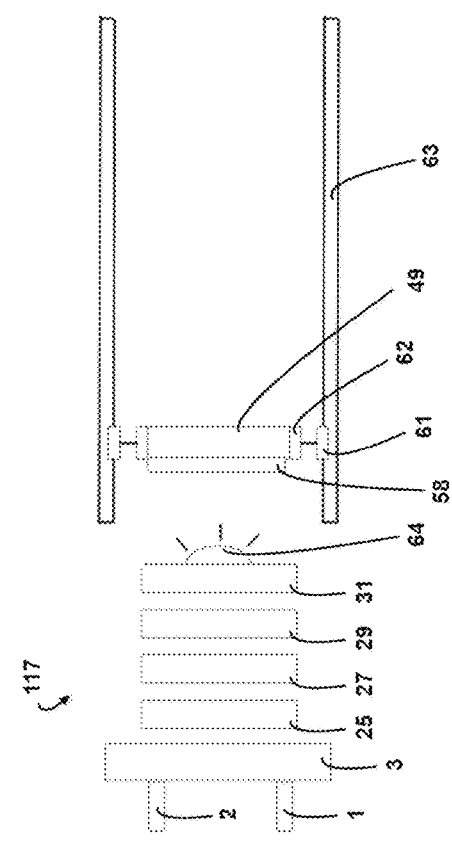
FIG. 10A
FIG. 10B

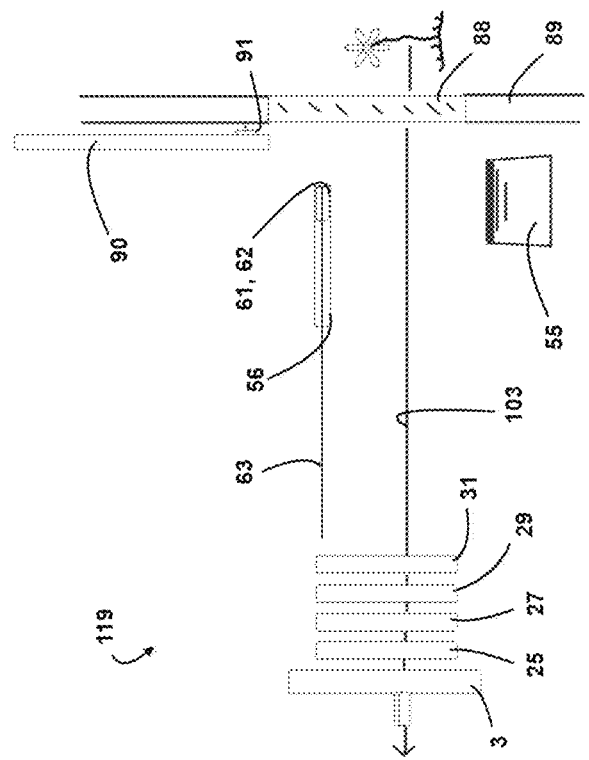
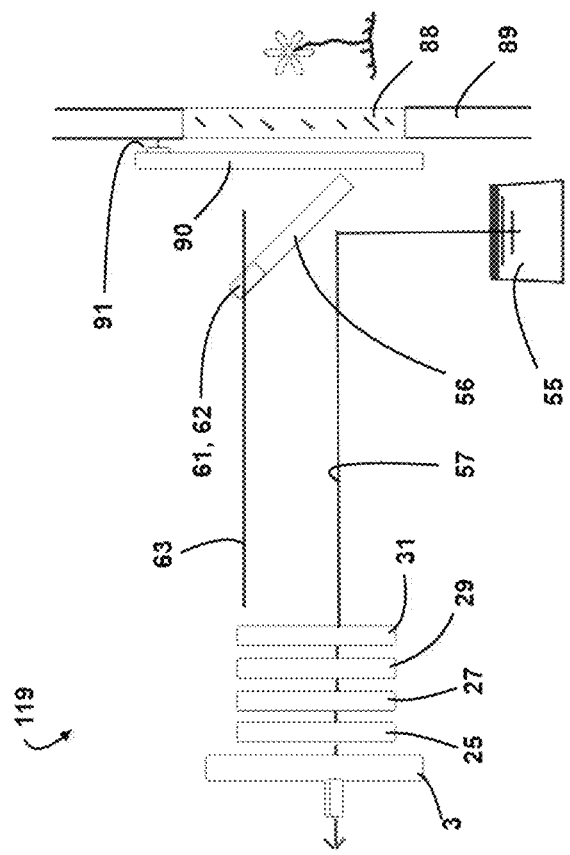

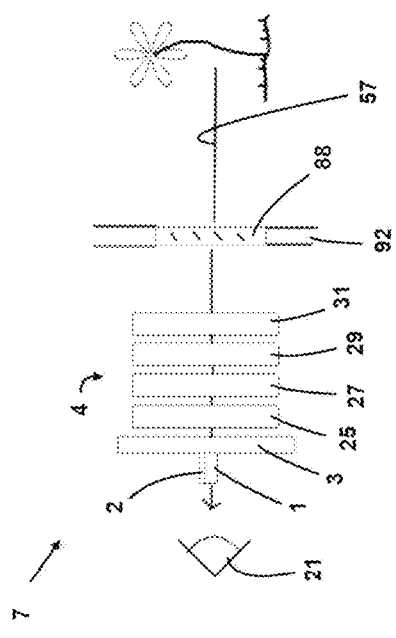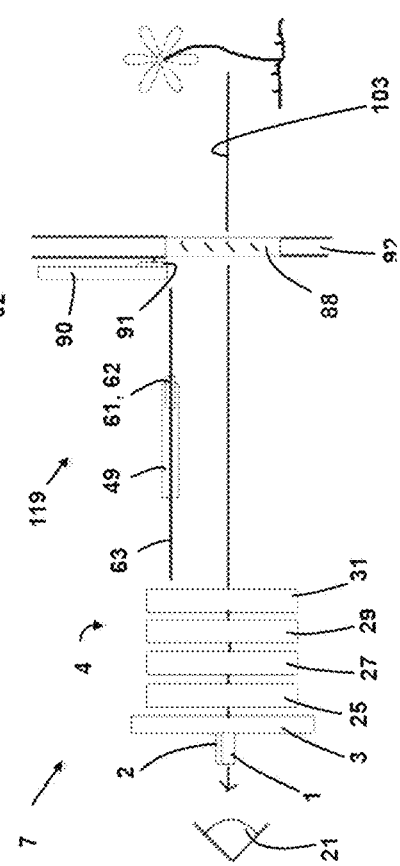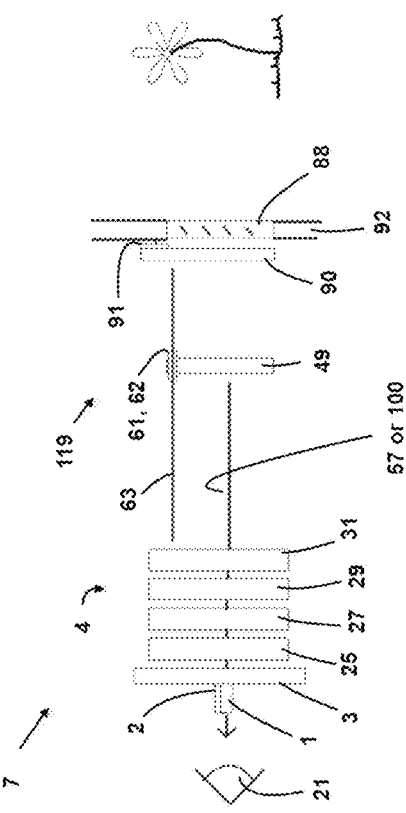

| | Optical Elements | | | | | | | |
|---|---|---|---|---|---|---|---|---|
| D | 1 | 2 | 3 | 4 | 5 | 6 | 7 | 8 |
| H-SPH | Plano | -2.00 | -4.00 | -6.00 | -8.00 | +2.00 | +3.00 | +4.00 |
| L-SPH | Plano | -0.25 | -0.50 | -0.75 | +0.25 | +0.50 | +0.75 | +1.00 |
| H-CYL | Plano | -1.00 | -2.00 | -3.00 | | | | |
| L-CYL | Plano | -0.25 | -0.50 | -0.75 | | | | |

FIG. 14

| Left Eye | Right Eye |
|---|---|
| Sph: | Sph: |
| Cyl: | Cyl: |
| Axis: | Axis: |
| Acuity: | Acuity: |
| Add 1: | Add 1: |
| Add 2: | Add 2: |
| Add 3: | Add 3: |
| VD: | VD: |
| PD: | PD: |

FIG. 17

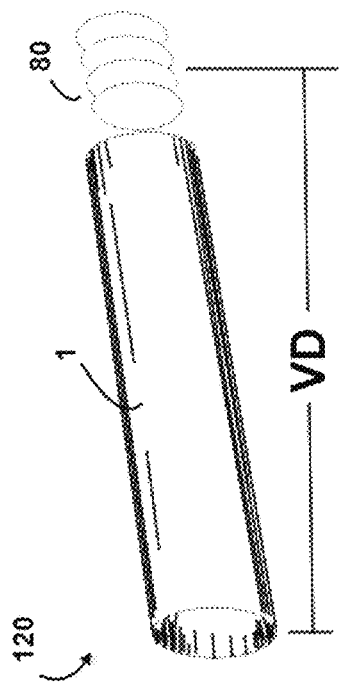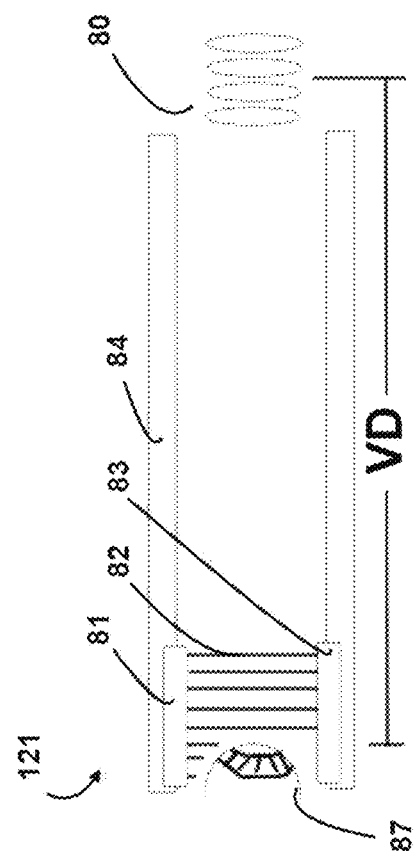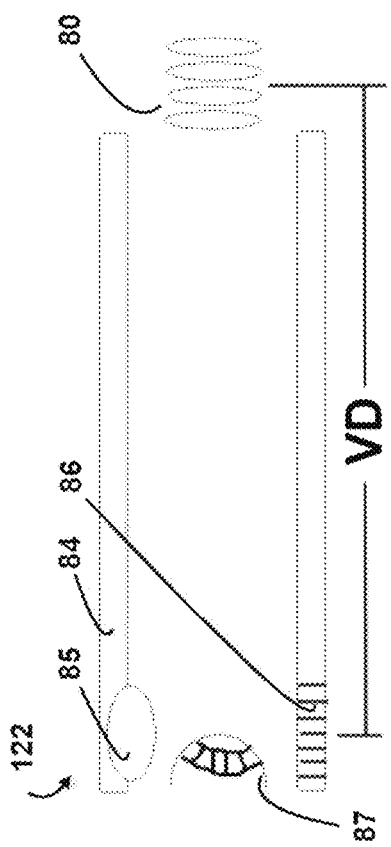

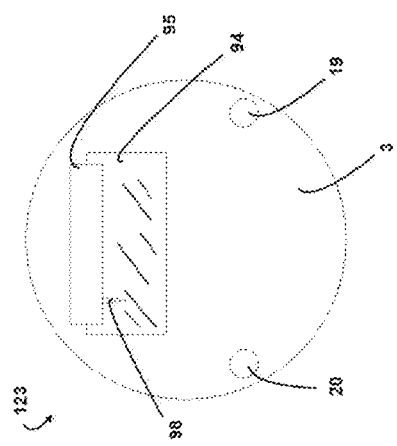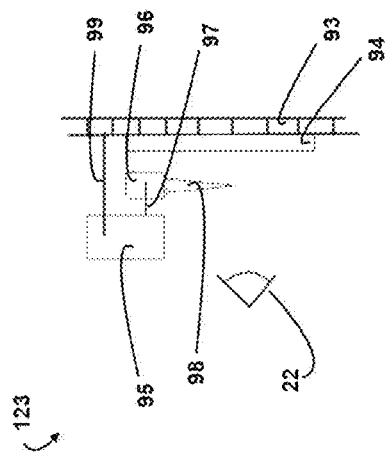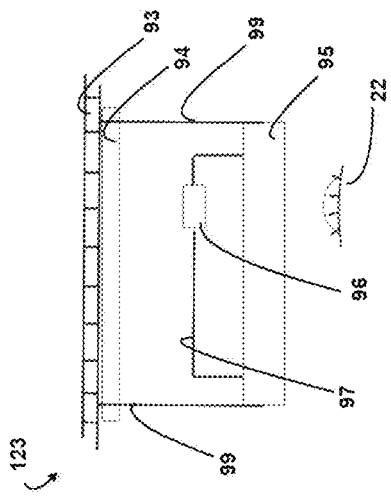

| Sphere | 0.00 | -0.25 | -0.50 | -0.75 | -1.00 | -1.25 | -1.50 | -1.75 | -2.00 | -2.25 | -2.50 | -2.75 | -3.00 | -3.25 |
|---|---|---|---|---|---|---|---|---|---|---|---|---|---|---|
| Microsteps | 0 | 1600 | 1700 | 800 | 750 | 750 | 700 | 675 | 700 | 850 | 900 | 1600 | 2000 | 3200 |

| Sphere | 1.00 | <pad> | <pad> | <pad> | <pad> | <pad> | <pad> | <pad> | <pad> | <pad> | <pad> | <pad> | <pad> | <pad> |
|---|---|---|---|---|---|---|---|---|---|---|---|---|---|---|
| Microsteps | 3450 | <pad> | <pad> | <pad> | <pad> | <pad> | <pad> | <pad> | <pad> | <pad> | <pad> | <pad> | <pad> | <pad> |

Fig. 35

SYSTEMS AND METHODS FOR
AUTOMATED SUBJECTIVE
SELF-REFRACTION

CROSS-REFERENCE TO RELATED
APPLICATIONS

This application is a continuation-in-part to application Ser. No. 15/705,774, filed on Sep. 15, 2017, entitled, "SYSTEMS, METHODS AND APPARATUSES FOR SUBJECTIVE SELF-REFRACTION", the entire specification of which is incorporated herein by reference.

BACKGROUND

Field of the Art

The disclosure relates to the field of vision care, and more particularly to a subjective self-refraction (SSR) system for providing eye measurements.

Discussion of the State of the Art

According to the World Health Organization's August 2014 update on visual impairment and blindness, uncorrected refractive errors are the main cause of moderate and severe visual impairment in the world and 80% of all visual impairment can be prevented or cured. Even within the U.S., many people lack the funds, insurance, or time needed for a traditional office-based refraction with an eye care professional.

Uncorrected refractive error results in loss of productivity and quality of life. More recently, objective refraction techniques have become common in the field. Objective refraction techniques attempt to correct for refractive error without a response from the user or patient. Types of objective refraction comprise (but are not limited to): retinoscopy, auto-refractors, and waveform aberrometers. These methods are costly and typically cannot provide the most accurate assessment of a person's refractive error. Currently the "gold standard" or most accurate method of refraction is subjective refraction using a set of trial lenses or corrective lenses. A disadvantage of this gold standard is that it currently requires another person who is highly trained in the art of refraction to manipulate a phoropter or use a Jackson-Cross cylinder. In the U.S. it currently takes four years of undergraduate training followed by four years of Optometry school to obtain a Doctor of Optometry along with associated tuition costs. Obtaining a Doctor of Ophthalmology is even more difficult and costly. Because of these difficulties in obtaining training, according to the World Health Organization, in certain parts of the world, the ratio of eye care professionals to people is considered a world health crisis. In Africa, for example, it is estimated that there is only one mid-level eye-care specialist for every 500,000 people and the minimum human resource requirement is 1 eye health professional for every 55,000 people (The Crisis in the Eye Health Workforce in Africa, IAPB, 2014). Presently, a system that allows an untrained user/patient or customer to perform subjective refraction on themselves does not exist. Such an SSR would prove beneficial both in the U.S. and worldwide.

In recent years, computer processing power has reached a point where Artificial Intelligence (AI) has increased productivity and reduced human labor in the workplace across a wide range of industries, including the medical industry. Additionally, various machine and deep learning techniques, which are a type of AI can be successful with improving accuracy across a multitude of processes. For example, a refraction starting and/or ending point may be calculated by feeding a user's health data through one or more predictive models, including Artificial Neural Networks (ANNs). The use of AI, including ANNs will have numerous benefits to a refraction process by supplementing or replacing interactions between the practitioner and patient, thereby improving efficiency, quality and lowering cost. The use of AI will further increase efficiencies and accuracy in a refraction process by reducing the required number of user inputs and by predicting starting and/or ending points for a refraction. The development, training, use, and integration of predictive models with an SSR process is described herein. It should be understood that these methods will continue to improve over time as the number of patient data points grow, and as computer processing power and software capabilities also improve.

In completing office-based subjective refractions, it is uncommon for skilled practitioners to start a patient with plano/plano (0/0) spherical and cylindrical power lenses. Doing so would increase the time needed to complete an office-based refraction resulting in greater time between patients and less clients served. Practitioners who have a client history with a patient will often use a patient's latest prescription as a starting point and then add spherical or cylindrical power, according to a patient's verbal feedback. Other practitioners will utilize results from objective methods, such as auto-refractors, wavefront aberrometers, and the like, for the purpose of entering spherical or cylindrical starting points for a refraction. It is further understood that completing a refraction by these means will ultimately save time and improve accuracy. This can be a time-consuming process and it would beneficial to automate the steps using an SSR system. In addition, prior prescription data for a patient is not always available and in these cases, it would be beneficial to start a refraction with a data point that is unique and relevant to the patient's refractive error using other available health data that has a relationship with eye measurement(s). It would further prove beneficial to utilize a similarly derived eye measurement as an endpoint in SSR or to benchmark other refractive methods or predict a refraction as a standalone method.

When conducting an office-based subject refraction, skilled practitioners, through years of training and experience, are able to apply judgement based on feedback, including response time, tone, and other non-verbal cues from a patient in an office-based refraction. For example, a medical professional may ask a patient "can you see better with "1" or "2". If the patient answers "2" with a perceived level of confidence, the medical professional may skip through spherical lens power at a faster rate than they would if the patient provided verbal or non-verbal cues that revealed less certainty. This patient and practitioner interaction may be emulated with SSR which includes specific algorithms for the purpose of speeding up the process of providing vision measurements. For example, an SSR system may increase the 0.25 D step changes when the user is switching through lenses at a rapid rate using an input device. The step changes may increase from 0.25 D to 0.50 D when a user changes the diopter strength of the spherical component three consecutive times in the same direction at a predetermined threshold rate. Once the rate of change decreases below a threshold rate, software and a processor in the SSR system may change the step-change magnitude back to 0.25 D. Additionally, ANNs may be trained to predict an endpoint for a subjective refraction based on data gathered from an SSR system. An endpoint may be used to benchmark subjective or objective methods of refraction, including SSR.

In light of the above, what is needed in the art is a system, method and apparatus that allows a person with no prior training to receive automated vision measurements based on inputs without assistance from an eye care professional. Such an invention will improve access to vision services, convenience, and lower cost by increasing the speed and accuracy of refraction.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Systems, methods, and apparatuses are provided for allowing a user with no prior training in the art to perform subjective self-refraction (SSR) on at least one of their eye(s). Specific embodiments provide different means that generally may be described as a camera, a data processor with memory storage, supporting algorithms to synthesize data for the purpose of predicting and communicating refractive error, and a system, method and apparatus for completing SSR as further disclosed in US patent publication US 2019/008251 A1. These methods may standalone or be paired in any combination with each other.

The provided systems and methods generally relate to predicting and measuring refractive error based on variable inputs and an SSR process. Refraction is the process of finding a corrective lens that can compensate for an eye that has the presence of refractive error. The scope of refractive error for purposes of describing the provided systems and methods encompasses but is not limited to the following types: hyperopia, myopia, presbyopia, and astigmatism. The provided systems and methods increase access to vision correction services by improving convenience and decreasing the cost of refraction versus more traditional methods.

There are many variables that have a relationship with refractive error that may be used as a refraction starting point or to aid in predicting refractive error. For example, it is widely understood that refractive error increases with age. Presbyopia, for example is caused by age related changes to the ciliary muscle and lens of the eye, causing difficulty when focusing on objects at arm's length or closer. The prevalence of certain diseases typically occur in adulthood which may result in vision problems. For example, diabetes has been linked to changes in refractive error under hyperglycemic conditions. Diabetic retinopathy is a leading cause of impaired vision and results from high blood sugar, which over time, can damage a retina. This condition is further known as diabetic retinopathy. Age-related macular degeneration (AMD), cataracts, and glaucoma are also leading causes of vision impairment or blindness and increase in prevalence with age. While age is certainly a predictor of refractive error, there are widely accepted risk factors that contribute to the fore mentioned underlying conditions that may result in refractive error. For example, risk factors for diabetes are better understood to be: weight, family history, and the presence of gestational diabetes in pregnancy.

It has been known and widely understood by those skilled in the art for decades that certain ethnic groups are predisposed to vision ailments. For example, according to Kleinsten, Jones, and Hullett, et. al. (2003), there are significant differences in the prevalence of refractive error as a function of ethnicity, even after controlling for age and sex. Asians, for example have the highest prevalence of myopia, followed by Hispanics, African Americans and whites. For astigmatism, Asians and Hispanics have the highest prevalence followed by whites and Africans. Medical conditions resulting from genetics, such as a Slanting of Palpebral Fissure, or Enlarged Palpebral Fissure are more prevalent with certain Asian races. The angle or slanting of the palpebral fissure has been shown to predict the severity of astigmatism. Garcia, L. M., Huang, D., Crowe, S., Traboulsi, E., et. al, (2003) established a relationship between the axis and degree of high astigmatism and obliquity of palpebral fissure as published in the Journal of American Association for Pediatric Ophthalmology and Strabismus, 7(1), 14-22.

Other studies have identified relationships between nearwork, or work related to reading, writing and computers, as a cause for myopia; particularly among school age children and into adulthood. Hsiu-Mei Huang, Dolly Shuo-Teh Chang, and Pei-Chang Wu (2015) found that "near work activities were associated with myopia and that increased diopter-hrs of near work might increase myopia prevalence."

Moreover, a patient's last known eyeglasses prescription may be the most relevant and significant data point in predicting refractive error. While it is widely understood that most myopic patients stabilize in their 20s or 30s, Bullimore et al. (2003) reported that 21% of contact lens wearers between the ages of 20 and 40 years of age progressed at least 1 D over 5-year period of follow-up indicating a progression for some patients.

All of these variables, or other variables, when taken in combination may be relevant for predicting refractive error and serving as a starting or ending point for a subjective refraction method, or to provide a benchmark with subjective or objective methods.

It must also be understood that future advancements in technology, medical knowledge about refractive error, and storage/access to digital data, will only strengthen machine and deep learning capabilities with regard to predicting refractive error. The scope of independent variables that have the potential to affect refractive error are expansive and thus, should not be limited only to ones discussed herein. It is widely understood by data scientists that machine and deep learning algorithms are often able to determine the presence of relationships within data sets that humans are unable to identify. Thus, ANNs can be developed to benefit humans in ways that would not be possible otherwise. One way that ANNs may benefit humans, which has not been disclosed in the prior art, is by predicting eye measurements. It is anticipated that the methods disclosed herein will continue to improve as training data sets grow and computer processing power becomes even greater.

Given this novel approach to a method for predictive refraction, it may stand alone or serve as a supplement to existing refractive methods or SSR. There are many traditional subjective refraction methods administered by medical professionals. While effective, these methods remain costly and inconvenient for many users. As such, a predictive refraction method, when supplemented with more traditional subjective methods may create a faster and more accurate user experience. In another embodiment, a predictive method only may interface with objective methods of refraction such as a physician-based retinoscopy, wavefront sensors, aberrometers, or auto refractors. In another embodiments, a predictive method may serve as a benchmark model or method to these already known and widely utilized methods including a traditional office-based refraction. In yet another embodiment, it may serve as a completely stand-alone method by capturing patient or user health data on a smart-phone application and predict eye measurements based on that data and a supporting model.

In the preferred embodiment, there will be an intake process whereby a user approaches an intake kiosk and looks directly into one or more cameras. The camera(s) along with manually entered user inputs will be combined to determine a data set that is useful in creating a patient profile for the purpose of determining a starting point for SSR. A user may enter health related data such as age, race, gender, weight, family history, medical history, prior eyeglasses prescription and date, or other information that may have a relationship with refractive error. These data may be entered through an already standardized intake process or through an application that interfaces with a tablet or smartphone that is connected to the internet. Additionally, camera(s) may capture certain characteristics, including variables that are not commonly known such as the slant of the user's palpebral fissure or the palpebral fissure width. Both data are relevant for ascertaining the presence of astigmatism. Rather than manually entering data, a system comprising cameras, transfer learning, and developed artificial neural networks (ANN), may assess age, gender, height, and other feature data, which may be used by a computer to auto-update or create a user profile. In other embodiments, the camera(s) may capture more obvious variables such as if a user is wearing glasses. Detailed cameras with higher resolution may be able to measure the eye's axel length, curvature of the cornea, curve of the lens, the presence of corneal ectasia to further determine the presence of potential refractive errors or other disease. All of these variables, when taken in combination, have proven to be relevant for predicting the presence and severity of refractive error.

The variables and resulting dataset may be greatly expand based on advancements in knowledge as discussed above. Additionally, data may be gathered from prior clinical studies, health records, prior recorded SSR sessions, and the like. Therefore, the variables discussed in this specific embodiment serve as examples only and should not be limiting in nature. Further it should be obvious that health data entered by a user or obtained from a camera can flow through a network and be stored in a server, such as a cloud server. Each user profile will strengthen the data set which will be applied to improve future predictive refraction models.

There are many algorithms having their roots in multivariate regression analysis that could be applied to a training data set to predict a refraction. In general, multiple mathematical models, such as regression equations or location parameters may be developed for both spherical power and cylindrical power models which will serve as dependent variables. Cylindrical power can be further categorized for common vision ailments such as hyperopia, myopia, and presbyopia which could serve as dependent variables, each requiring a separate mathematical model and training data set. Independent variables may be those based on previously discussed physical attributes (i.e. age, race, gender, etc.) or other data points with potential to affect one's refractive error (e.g. the presence of diabetes or other known medical conditions, one's occupation, etc.). Further, other algorithms, an example of such is discussed herein, use Artificial Neural Network (ANN) modeling to predict spherical and cylindrical lenses based on certain input variables. Over time, the types of models created to predict refractive error will continue to expand and improve.

ANNs may be employed to further speed up the refraction process. In one embodiment, this may be done by training an ANN to predict a user's best spherical component based on one or more features, such as demographic data, facial/eye measurements, the direction and speed of prior spherical incremental changes during SSR, and the like. This prediction may be used as a starting or endpoint in a refraction, or to benchmark other refractive methods.

ANNs are complex computational algorithms. They take in one or more input values through an order of mathematical operations, then output one or more values. These calculations are overly time consuming, long, tedious, and prone to human error, thus they are best computed using computers. The number of calculations, types of calculations, and order of calculations is meant to simulate a biological brain. The human brain is made up of many single functional working units called neurons. Likewise, an ANN is made up of many mathematical units called perceptrons. A perceptron takes an input value X, multiplies it by a weight W, and adds a bias B. The result is then taken through an activation function A to produce an output value Y. Many perceptrons may be connected in both series and parallel in order to create complex ANNs. The output of one perceptron becomes the input of another perceptron. The inputs of the ANN that first enter a set of perceptrons is called the input layer. The last set of output values of the ANN is called the output layer. The layers of perceptrons in the middle of the ANN are called the hidden layers. Each perceptron in a hidden layer is called a node.

Similar to the human brain, sensory inputs are passed through many interneurons (analogous to many hidden layers of perceptrons), and then output a motor response. An ANN may take in different inputs of data X, process the inputs through many nodes (analogous to interneurons) and then output a response. The response is the answer to a particular question, in this embodiment, the output response Y, is a predicted best spherical component.

When developing ANNs to predicted eye measurements, the input features X, may first be converted into a numerical form that is on the same scale. This may be done using MinMaxScaler equation, StandardScaler equation, and the like. The activation functions A, at each node may be a sigmoid function, a tanh function, a ReLU function, and the like. There are many types of ANNs, such as convolutional neural networks, recurrent neural networks (RNNs), feed forward neural networks, and the like that may be used to predict eye measurements. Any embodiment of this invention for automated vision measurements, may use any type of ANN, deep machine learning and artificial intelligence to improve the process of automated vision measurements. The neural networks may have any number of layers, nodes, connections of any combination, activation functions of any combination, any loss function, and the like. The applications of ANNs in the automated process of obtaining vision measurements, is not limited by the examples in this publication.

The accuracy of ANNs for predicting the best spherical component may be measured using a loss function, such as mean squared error (MSE).

$$MSE = \frac{1}{n}\sum_{i=1}^{n}(Y_i - \hat{Y}_i)^2$$

This equation measures how close an ANN is to answering a question. Y is the true answer and Y hat is the ANN's approximation of the true answer. The Y data represents all the true answers in a data set and may be referred to as targets. The bigger the difference between the true Y value (target) and Y hat, the bigger the error. This calculated error is then used to train the ANN. This may be accomplished using a backpropagation algorithm or other suitable training algorithms and may use a gradient descent algorithm to optimize the weights by specifying a step size in which the gradient descent algorithm iterates after each training set, to determine a local minimum of error. The weights are thus updated in such a way, that future forward passes through the network will result in Y hat's magnitude being closer to the true target value. The method of training the ANN may include a step of stopping training if a loss function calculation is less than a prespecified threshold or after a pre-specified number of epochs. ANNs may be developed using computer programing language like Python, deep learning frameworks like Keras, data many be processed using data science tools such as Numpy and Pandas, and end-to-end open source platforms for machine learning like Tensor-Flow. Many techniques well known to those skilled in the art may be used in Keras and TensorFlow to design, shape, and train the ANN. This may include utilization of different batch sizes, dropout to avoid overfitting, different learning rates, Adam optimization algorithm, and different loss functions such as crossentropy. A more detailed explanation of this process is beyond the scope of this text, but is well understood by those skilled in the art. It is important however, to understand conceptually that the weights W, are adjusted after each epoch of training data set is passed through the ANN, so as to allow the ANN to provide future outputs that more closely approximate the targets. When the ANN's outputs are sufficiently close to the targets, the ANN may then be taken out of training mode, tested on new users, and then used to predict visual measurements at, for example, remote kiosks, clinics, and the like.

MSE is only an example. Other cost functions may be used depending on the types of data and targets.

When the weights and particular design of an ANN are sufficiently useful to solve a problem, the weights may be held constant, the output layer replaced with more hidden layers along with a new output layer. The weights in the new layer may be trained. This process is known as transfer learning. In this way, previously well designed and trained ANNs, may be used in new ANNs to solve similar problems. For example, there are ANNs that are already trained to take input data from a video camera and output a person's age and gender. Transfer learning may be used to automatically detect demographic data and use it in other ANNs that predict vision measurements based off of camera detected demographic data.

While the ANN is in training mode, every time X is passed forward through the ANN, the weights W are optimized, so that future forward passes through the ANN will result in more accurate answers. Thus, each weight W in the ANN is a variable that is adjusted during the learning process. The larger the training dataset (i.e. the more individuals from the population that are used to develop the training dataset) the more meaningful the updates to the weights after each epoch, thus the better the ANN will become at predicting eye measurements. Once the outputs (i.e. eye measurements) are sufficiently accurate, an ANN may be used to predict refractive error or other vision measurements.

An output device, such as a speaker, a video screen and the like may instruct a user during an SSR process. A user makes changes to a plurality of lenses with use of an input device. This input device may be a handheld device receiving tactile input from the user or a microphone receiving sound wave input from the user. Other input devices may be used that receive input from the user such as a tablet or smartphone. This input device transmits responses to one or more processor(s) within an SSR device in order to complete SSR.

A more simplified version of SSR may include a device wherein a user views written instructions through an eye piece, along with plano, or only plus spherical lenses which are mechanically manipulated to focus a near object. For example, a newspaper or one or more sentences at less than an arm's length. The lenses providing the best vision in this embodiment could be used to provide an eye measurement for making reading glasses or bifocals for the user. In this embodiment, instructions for keeping the circle of least confusion focused on the retina would not be necessary. An example of such an embodiment is provided in U.S. patent application: 20190082951, the example incorporated herein by reference. The instructions for such a refraction may involve keeping one eye closed or using an occluder, while the other open eye peers through an eyepiece. The user's hand may be instructed to turn a knob on the same side of the device as the open eye, in order to search for the best plus spherical lenses in 0.25 D increments, while focusing on an image. The device may refract one or both eyes at the same time using plano lens power, the same spherical lens power, or only one eye at a time.

At the end of an eye test as illustrated in this embodiment, a vision number, measurement, or even a prescription may be provided to the user. The system may further convert or extrapolate the number provided into a different number, measurement or even a prescription for computer glasses or for glasses used for very near vision activities such as for use in soldering or sewing. The system may provide three or even four numbers for vision uses at different ranges for different purposes. These measurements may be provided via software or from calculations taken from a simple chart using a starting measurement by taking ½ the standard near vision number and by rounding down to the nearest quarter diopter. For instance, if a user's starting number is +2.0 D for reading glasses, for example, then for computer glasses the result may be +1.0 D. If their vision measurement was +2.25 D, then for computer glasses, the result may still be +1.0 (half of +2.25 rounded down to the nearest quarter diopter). The system, method and apparatus, along with the supporting software would increase spherical power by +1.0 D for very near vision needs as a starting point such as for soldering or completing other detailed craft works. For example, if a user measures +2.25 for standard near vision, the additional spherical strength needed to complete these works may increase to +3.25 for very near vision glasses. These measurements may be taken in one or both eyes at the same time, through automated or manual means.

The current SSR system may store a vast amount of health-related data. In addition to refractive eye measurements at different distances, measurements such as visual acuity with an accuracy assessment, visual quality, automated vertex distance, pupillary distance and the like may also be measured and stored. Further, other health measurement data such as blood pressure, pulse, oxygen saturation, weight and the like may be taken which can be used for predictive modeling or patient health information.

The SSR system may also have a plurality of presorted eye glass frames and or lenses, contact lenses, or other eyewear that is housed within the unit or nearby the unit, which can be dispensed onsite automatically similar to an ATM or vending machine. A fob device, smartphone, or biometric recognition technology may be used to match a user to their appropriate eye measurements before fulfillment of the order. In another embodiment, the SSR system may interface with a third party or affiliate platform to order corrective lenses on-line.

In parts of the world where the ratio of eye care professionals to people is much lower than in the U.S., and where local currencies are unstable, it would be ideal to provide an SSR kiosk that accepts cryptocurrencies and other forms of payment. It should be widely understood that health kiosks, such as those used for vision care services, will accept various forms of payment such as cash, credit card, apple pay, and the like. In recent years, the prevalence of cryptocurrencies, particularly in countries where citizens do not have access to the payment systems, have become more prevalent as a means of payment. Therefore, it is increasingly important that self-service kiosks, such as ones that may be used for refraction services include the ability to receive payment of one or more cryptocurrencies such as Bitcoin, Ethereum, Libra, and the like. In establishing a means to accept cryptocurrency, an SSR kiosk may contain a digital wallet. An embodiment of the invention may include a centralized digital wallet, which may be stored with a third-party vendor that accepts payments from all predictive refractive kiosks worldwide. The scope and responsibilities for collecting cryptocurrency payments should not be limiting in nature. Additionally, it would be fully expected by one skilled in the art of finance that the ability to accept payments will evolve as the payment systems change over time.

The embodiments provided are only examples of how this technology may be used to provide a user with one or more eye measurements. In keeping with the spirit of this invention, there are many types of systems with or without corrective lenses that may be used, just as there are many types of algorithms, programming and instructions that may be used. In this claimed invention, embodiments are provided for an invention that subjectively and in some cases objectively (e.g. vertex distance or using autorefractors as a start point) automates a process for predicting, measuring, and then verifying eye measurements. Thus, the provided examples of this technology are not to be interpreted as an exhaustive list and the fundamental elements of this technology may be combined in any combination, with no need to include all elements of the invention.

BRIEF DESCRIPTION OF THE DRAWINGS

The novel features of the invention are set forth with particularity in the appended claims. A better understanding of the features and advantages of the invention will be obtained by reference to the following detailed description that sets forth illustrative embodiments, in which the principles of the invention are utilized, and the accompanying drawings of which:

FIGS. 7A-B illustrate a system that allows a user to switch between distant and near vision test images in accordance with some embodiments of the invention.

FIGS. 10A-B illustrate a system for testing near and far vision using a digital acuity chart with a configurable operating distance of 6 feet or less and a near vision test attached posteriorly to the digital acuity chart, which is rotatable and can be adjusted for different near distances in accordance with some embodiments of the invention. The digital acuity chart may be configured to also allow for different near vision tests at different lengths, thus making the posteriorly attached near vision test and motor gears obsolete.

FIGS. 12A-B illustrate a system for switching between acuity vision testing and quality vision testing in accordance with some embodiments of the invention.

FIGS. 13A-C illustrate different lens chamber systems for testing visual quality in accordance with some embodiments of the invention.

FIG. 14 illustrates the optical elements that may be found on the disks in a lens chamber in accordance with some embodiments of the invention.

FIG. 17 illustrates an example of data that may be presented on a display screen in accordance with some embodiments of the invention.

FIGS. 18A-C illustrate different systems for automating the measurement of the VD in accordance with some embodiments of the invention.

FIGS. 19A-C illustrate a system for automating the measurement of the PD in accordance with some embodiments of the invention.

FIG. 35 illustrates exemplary sequential vision measurement data that may be fed to an RNN in accordance with some embodiments of the invention.

DETAILED DESCRIPTION

Figure 1:
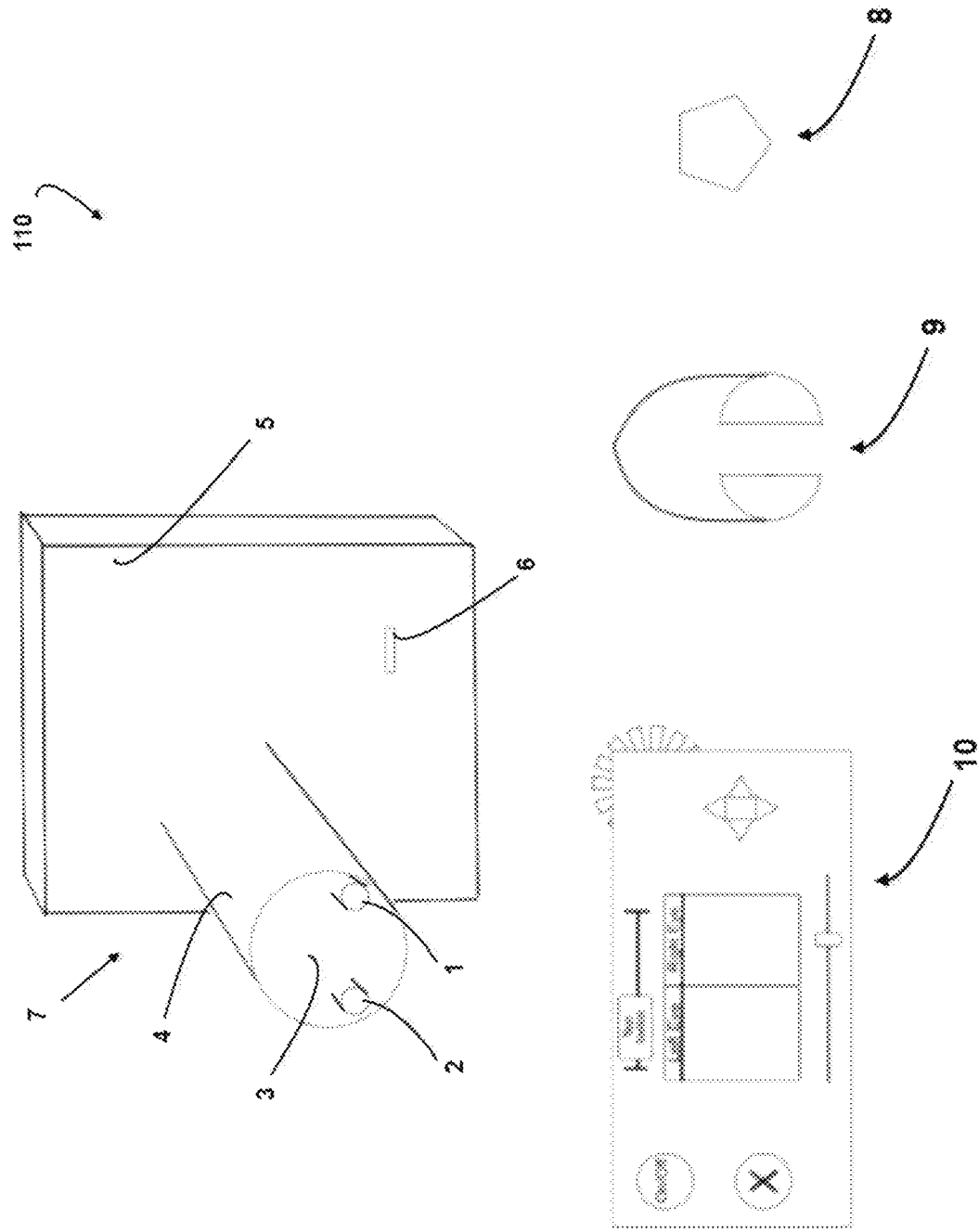
FIG. 1 illustrates an SSR system along with an optional fob device that may be used to store and transfer eye measurements or other health data in accordance with some embodiments of the invention.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

In one aspect, an improved SSR system or apparatus is provided. The system or apparatus configured for screening and testing near and far vision, assessing visual acuity and quality by guiding a user with voice commands and/or visual instructions. The system or apparatus may automate the measuring processes for assessing VD and PD without use of the Jackson-Cross Cylinder. This provides advantages for further applications such as providing eyewear at an improved efficiency in the refractive process or lowering manufacturing costs as compared to auto-phoropter.

In some embodiments, the systems and/or apparatus may comprise an outer casing covering a series of optical components such as lenses mounted on parallel discs. The system or apparatus may comprise user input controls, such as a controller, for controlling one or more motors to move the lenses in accordance with sensory cues, such as audio voice commands, and one or more user inputs. The system or apparatus may be configured to keep light rays focused on a user's retina when a user is performing SSR at different distances using different tests. This is advantageous to provide flexibility of the system to accommodate different users and/or uses under different conditions.

Embodiments of the invention that assess visual quality may be further adapted to allow the user to look either left or right by placing the lens chamber(s) on a motorized swivel that is controlled by the handheld controller. Benefits of this embodiment comprise further assessment of visual quality by testing the refractive measurements against real-world objects of different colors, at different angles and under different lighting conditions.

There are many other devices and mechanisms instead of an auto-phoropter, that may be used for manipulating trial lenses in front of a user's eye to accomplish SSR in combination with voice commands, eye tests, and a control unit. These devices may also be wirelessly controlled or physically attached to the hand-held controller. Thus, usage of an adapted auto-phoropter for manipulating trial lenses in front of the user's eye is the preferred method in the disclosed embodiments, but other embodiments may manipulate the trial lenses using a non-phoropter-like system.

The provided systems may also comprise an electronic media storage device with memory, which could be inserted into the hand-held controller for the purpose of saving eye measurements. This would greatly improve the efficiency of an office-based refraction by allowing a facilitator to direct patients to take one of these memory storage devices and insert it into the controller of the system. Alternatively, the facilitator could be replaced by a set of printed, video, and/or audio instructions that directs the patient in a similar fashion. The patient would then perform SSR while waiting to see the eye care professional. Next, the patient would be directed to a same or similar system, which is operated by an eye care professional via the handheld controller. The memory storage device would be inserted into the controller and the patient would be seated at the device, viewing through the test window(s). The data saved on the storage device may then auto-manipulate the lenses in such a way that the same prescription from the waiting room refraction is in the patient's optical path(s). The eye care professional may then make any necessary changes to the prescription before printing or transmitting the prescription. Next, the patient would then take the memory storage device with them and drop it off with the receptionist or into a bin on their way out of the office where data is removed from the device. A future patient may use the same memory storage device and the process repeats itself. Efficiency may further be improved by combining proximity or contactless or wireless card or fob technology with the memory storage device. Thus, by having the patient wear the storage device as a necklace for example or place the storage device in their pocket, the patient and eye care professional may perform the above process without needing to insert and remove the memory storage device from controller. Efficiency may further be improved by adding pager technology to the memory storage device. Thus, a patient would be alerted by sensory cues emitted from the memory storage device when a refractor device becomes available in the waiting room and it is the patient's turn to use it. The memory storage device would also be able to alert the patient when it is time to go to the exam room and meet the eye care professional. Thus, the memory storage device could be adapted to serve the purpose of holding a patient's place in line. Overall, this system and method would improve patient flow during office-based refractions, improve patient experience and satisfaction, and improve the efficiency of the eye care professional's office.

DEFINITIONS

Optical path: A straight line of sight as viewed from a user's eye, which passes forward from the user's eye through an eyepiece, then through a series of corrective lenses housed within a lens chamber, and terminating at an object such as a Snellen chart, a digital acuity monitor, a tree in a field and the like.

Visual test object: An object wherein a user is instructed to focus their vision on during SSR or during a visual acuity test. The object may be a Snellen chart, a digital acuity monitor, or another object within a user's visual field.

Visual acuity test: A system using a visual test object to automate the measurement of visual acuity. The system may further provide an automated measure of confidence of the visual acuity measurement.

Optical infinity: A distance used to test for far vision, where the light rays from an eye chart are considered parallel. Typically, the eye chart 20 feet or more from the eye.

Eye measurements: Measurements related to the eye, including, but not limited to objective or subjective refraction measurements, visual acuity and quality measurements, vertex distance, pupillary distance, slant of palpebral fissure, and the like.

Refractive measurements: An eye measurement that is a function of a user's lens and/or corneal shape.

Vertical meridian of a lens: A vertical line bisecting a lens by connecting the north and south poles. Light passing through this meridian will converge or diverge at different rates depending on the shape of the lens.

Horizontal meridian of a lens: A horizontal line bisecting a lens, i.e. at the equator. Light passing through this meridian will converge or diverge at different rates depending on the shape of the lens.

Astigmatism: The shape of an eye's refractive elements (i.e. lens and cornea) is such that light entering the eye does not focus at one point, but rather more than one point causing blur. An example is when the diopter power of the vertical meridian of an eye's refractive elements is different from the diopter power of the horizontal meridian, resulting in the vertical meridian's focal line being found in a different position in space than the horizontal meridian's focal line.

Interval of Sturm: The distance between the focal line created by the vertical meridian and the focal line created by the horizontal meridian in the above example.

Circle of least confusion: A circle created where the length of the focal lines of both the vertical and horizontal meridians cross and are of equal length, thus creating a circular image rather than an image stretched along either the vertical or horizontal meridian.

Maintaining the spherical equivalent: Adjusting the spherical power while testing or correcting for astigmatism in order to keep the circle of least confusion focused on the retina.

Feature data: data on different independent variables that may be fed through an artificial neural network. As related to the current invention, this may include variables such as demographics and prior eye measurements for one or more individual users.

Row of data: as related to this invention, a row of data represents the demographics (independent variable) and prior eye measurements (dependent variable) of one particular user that may be used to train an artificial neural network.

Training dataset: rows of data, each row in the case of our invention, represents demographics and prior eye measurements from one particular user. The entire training dataset being fed forward through an artificial neural network (i.e. one epoch) during a training algorithm.

Mini-batch: a collection of rows of data that may be fed forward through an artificial neural network (i.e. one iteration) during a training algorithm.

Parameters: Variables such as weights and biases that may be changed within an artificial neural network in order to changes the network's output(s).

Mathematical predictive model: A system for performing specific calculations on independent variables, which results in calculated dependent variables. The specific calculations and order of the calculations depends on the shape of mathematical predictive model and may include, but is not limited to artificial neural networks. The real-time use of the mathematical predictive models used in the applications described herein require a computer to be of practical use, because the calculations are computationally time consuming, expensive, and prone to human error.

Conceptual Architecture

FIG. 1 illustrates an SSR system 110 in accordance with some embodiments of the invention. The SSR system 110 may comprise a refractor 7, which is further comprises a lens chamber 4 and a built-in eye test. The built-in eye test may connect to, be housed within, or form part of the wall of a lens chamber 4. In the embodiment represented by FIG. 1, a mirror box 5 is used for the built-in eye test. Lens chamber 4 houses a plurality of trial lenses. Mirror box 5 houses a set of mirrors and an illuminated eye test. Lens chamber 4 may comprise a front cover 3. Attached to the front cover 3 is a left eyepiece 1 and a right eyepiece 2.

During the SSR process, light rays may be emitted from an illuminated eye test within mirror box 5, which reflect off a series of mirrors to reach optical infinity (i.e. become nearly parallel) before entering lens chamber 4. After entering lens chamber 4, the light rays are refracted by trial lenses within lens chamber 4 prior to entering the user's eye.

The lens chamber 4 may house any number of parallel disks with any number of optical elements. The embodiments provided use a High Power Spherical (H-SPH) Disk, which holds spherical lenses of high diopter (D) power, a Low Power Spherical (L-SPH) Disk which holds spherical lenses of low D power, a High Power Cylindrical (H-CYL) Disk which holds cylindrical lenses of high D power, and a Low Power Cylindrical (L-CYL) Disk which holds cylindrical lenses of low D power.

The system 110 may comprise a device or component for output of eye measurements. The output device or component can include any hardware, software or a combination of both. For example, a printer output 6 may deliver the eye measurements to the user. In another example, eye measurements may be displayed on a display screen or electronically transmitted to the user through a web-based or wireless platform such as a smartphone, tablet computer or email.

The system 110 may comprise headphones 9, such as wireless headphones so the user can receive auditory instructions. The system 110 may comprise a control unit 10. The control unit 10 may comprise a mobile device such as a smartphone, tablet, iPad, notebook or other mobile device as is known to one of ordinary skill in the art. While the control unit 10 can be configured in many ways, in some embodiments the control unit 10 comprises a smartphone comprising a touch screen display, in which the touch screen display is configured to receive instructions from the user, for example. The control unit 10 may be used to manipulate the trial lenses and advance the user through the SSR process. In performing SSR, a device user follows sensory cues, such as voice commands from either headphones or speakers and provides input using a wireless or wired-in handheld controller. Instructional video may be combined with audio commands, however in the case of hearing-impaired users, video instructions only may be used. Video may be available through an internet-delivery channel. It should be understood that an input controller is not always necessary to complete SSR. The user may also provide input to the device verbally via voice recognition software. At least one processor or operating unit with pre-programmed software forwards user input to at least one motor, which then drives the necessary changes in mounted lens hardware, and various systems for testing near vision, far vision, visual quality and visual acuity during the refractive process.

The system 110 may comprise a fob 8, which communicates with one or more refractor(s) 7 and electronically stores eye measurements from the SSR process for later use. The fob can be any electronic storage unit, such as memory (e.g., read-only memory, random-access memory, flash memory) or a hard disk. The communication between the fob and the system 110 may be wireless or wired communications. The communications may include communications over a network or a direct communication. Examples of wireless communications may include, but are not limited to WiFi, 3G, 4G, LTE, radiofrequency, Bluetooth, infrared, or any other type of communications. In the case when it is a wired communication, the system 110 may comprise an interface (e.g., drivers, port) to enable the data transmission with the fob.

The fob 8 may store results of refractive testing. The resulting refractive measurements, VD, PD, and the like, may be displayed, printed, or transmitted to the user or another individual for further use, such as consultations, manufacture of eyewear, and the like. For example, the eye measurements may be used with current telehealth/telemedicine technology for the purpose of brining eye care professionals and consumers together and the like. In another example, the eye measurements may be used for vision screening to aid a user in determining if more thorough follow-up eye care is needed. Details regarding applications of the fob are discussed later herein.

Figure 2:
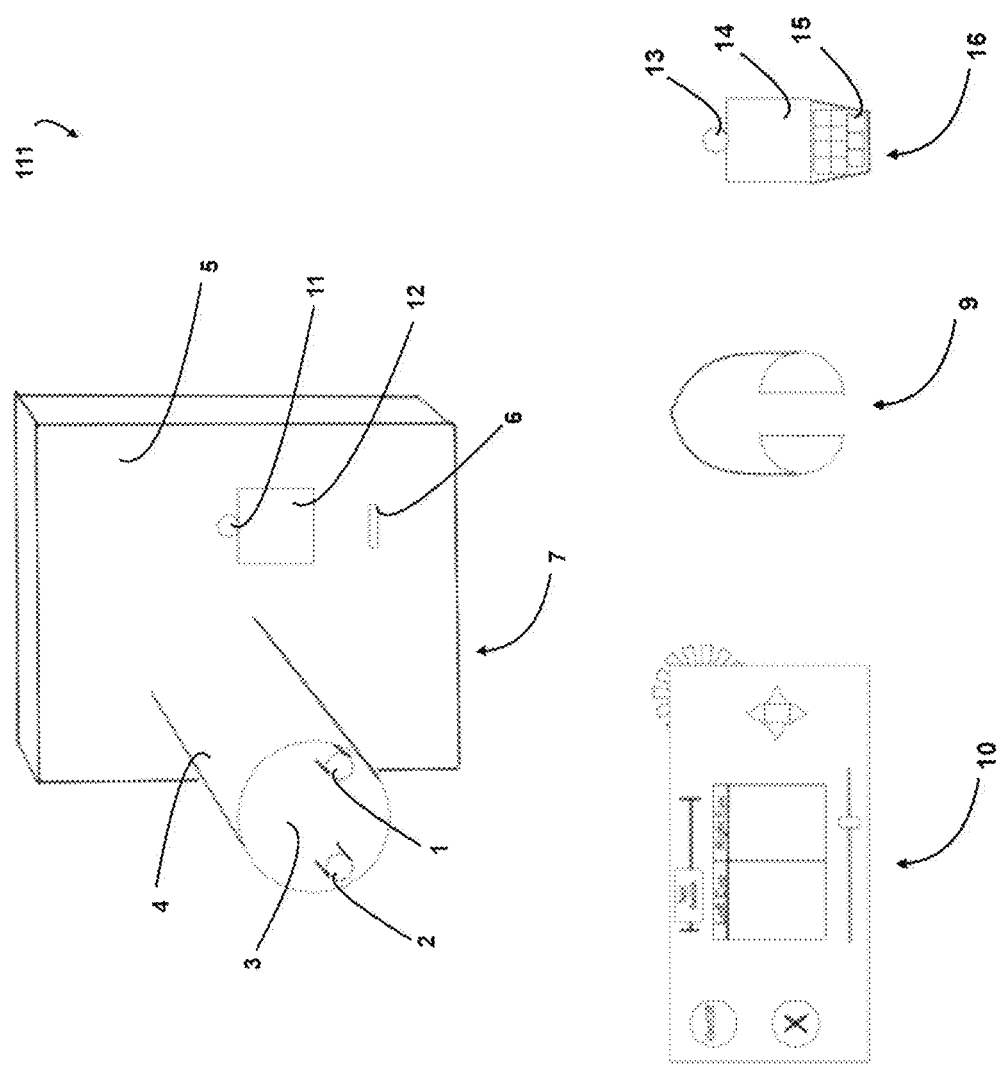
FIG. 2 illustrates a real-time audio-video portal between the user and an eye care professional in accordance with some embodiments of the invention.

In some embodiments, the SSR system may be configured to enable communication between a user and a remote eye care professional. FIG. 2 illustrates an SSR system 111 with a real-time audio-video portal between the user and an eye care professional in accordance with some embodiments of the invention. The SSR system 111 may comprise an audio-video portal that connects a user and an eye care professional in real time so they can exchange information. The audio-video portal comprises a user video camera 11, and a user video monitor 12, so that the eye care professional can interface and communicate with the device user to confirm the results of the SSR or provide other telehealth care as necessary. Similarly, an eye care professional may use a remote eye care professional portal 16 to communicate with a user and send prescriptions. The remote eye care professional portal 16 may be located remote to the audio-video portal. Eye care professional portal 16 may comprise an eye care professional camera 13, an eye care professional video monitor 14 and an eye care professional user interactive device 15 (e.g., keyboard, button, mouse, touchscreen, touchpad, joystick, trackball). The communication may be wired or wireless communication. In some embodiments, the remote eye care professional portal may be hosted on eye care professional device. The device may be a network device capable of connecting to a network, such as a local area network (LAN), wide area network (WAN) such as the Internet, a telecommunications network, a data network, or any other type of network. The device may be capable of direct or indirect wireless communications. The device may be capable of peer-to-peer (P2P) communications and/or communications with cloud-based infrastructure. The device may be a mobile device (e.g., smartphone, tablet, pager, personal digital assistant (PDA)), a computer (e.g., laptop computer, desktop computer, server) or any other type of device. Communication may be via an internet connection or other means of remote data transmission.

Figure 3:
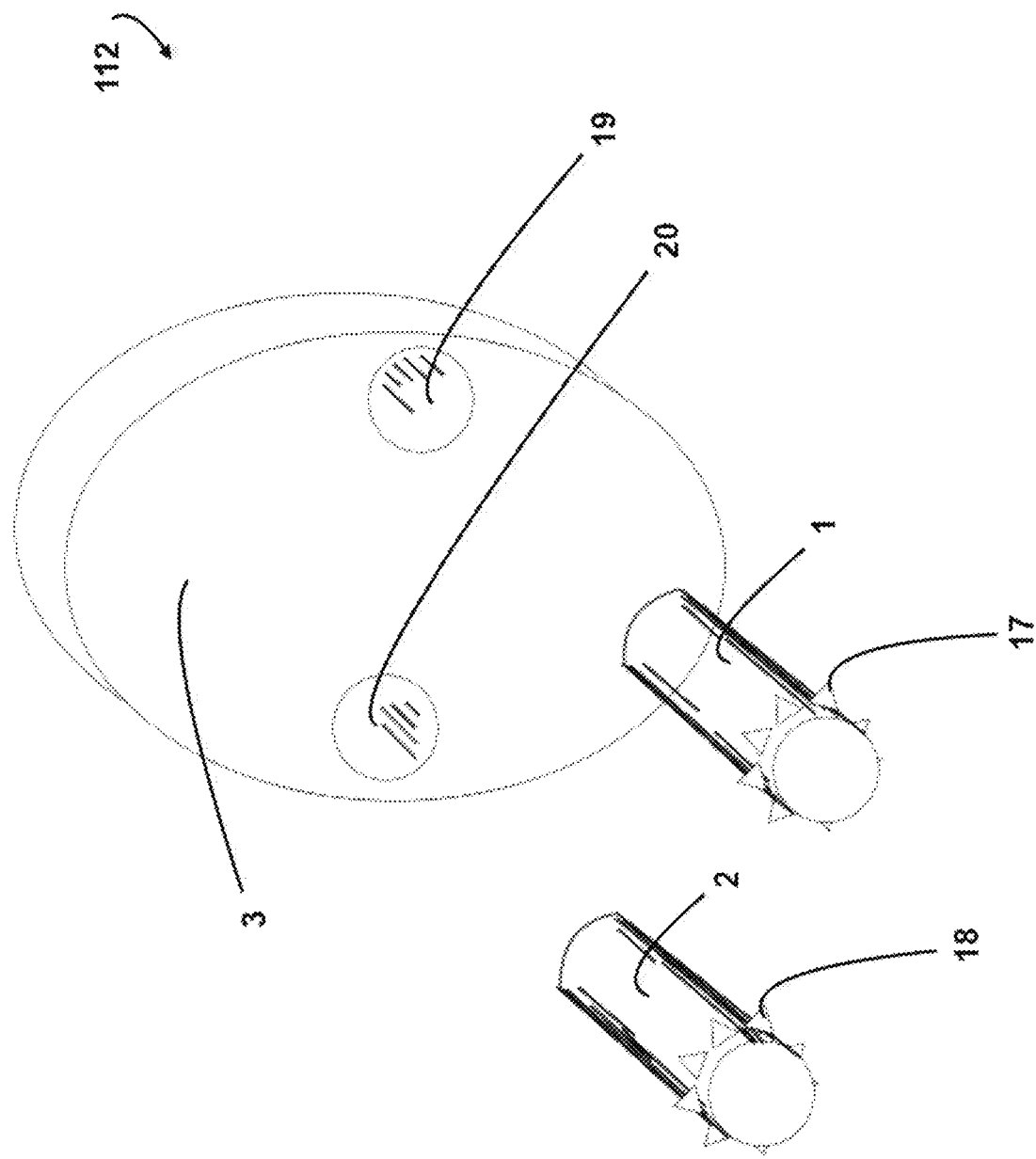
FIG. 3 illustrates a system for standardizing the VD distance using premeasured eyepieces and for ensuring correct left/right eye laterality using light signals in accordance with some embodiments of the invention.

The SSR system may comprise components for performing VD measurement. FIG. 3 is an exploded view of a system 112 for standardizing the VD distance, in accordance with some embodiments of the invention. The system 112 may comprise pre-measured eyepieces for ensuring correct left/right laterality using light signals. The system 112 may comprise a left test window 19 and a right test window 20, which are mounted to a front cover 3. Left eyepiece 1 and right eyepiece 2 are mounted directly over the left test window 19 and the right test window 20, respectively. Left eyepiece lights 17 and right eyepiece lights 18 are attached to left eyepiece 1 and right eyepiece 2, respectively. In the cases, the eyepiece lights may comprise light sources such as LED that may flash when the voice commands instruct the user to switch eyes. The lights may be turned off AFTER the user's eye is docked or may flash for just a few seconds. This is advantageous to ensure the patient looks into the correct hole and the correct prescription is provided for that eye, regardless if the user knows their right from their left. The user's end of each eyepiece is at a pre-measured and fixed position from the trial lenses, which allows for an automated and standardized measurement of VD. The eyepiece lights are preprogrammed to signal to the user, such as by flashing for example, when to look into the correct test window during SSR. This ensures that the eye measurements are recorded for the correct eye.

In some embodiments, a disk with a collimating lens and/or a Plano lens may be added to the row of disks in the lens chamber on the side furthest from the user's eye. This collimating disk may be used to further compress the refraction distance for optical infinity for the purpose of making the device smaller. The Plano lens may be added for the purpose of switching between distance refraction and near refraction.

When looking into the device, a spherical component and/or a cylindrical component is provided. The spherical component may comprise the D sum of the spherical lenses on the H-SPH Disk and the L-SPH Disk that is in the optical path. The cylindrical component may comprise the D sum of the cylindrical lens on the H-CYL Disk and the L-CYL Disk that is in the user's optical path.

In some cases, lenses of 0.25 D increments may be used, however larger or smaller D increments may be used for any number of reasons such as to lower unit cost, alter unit size, improve unit accuracy, or change the scope of refractive ailments being assessed. Astigmatism, hyperopia, myopia, and/or presbyopia and the like may or may not be tested.

Figure 4:
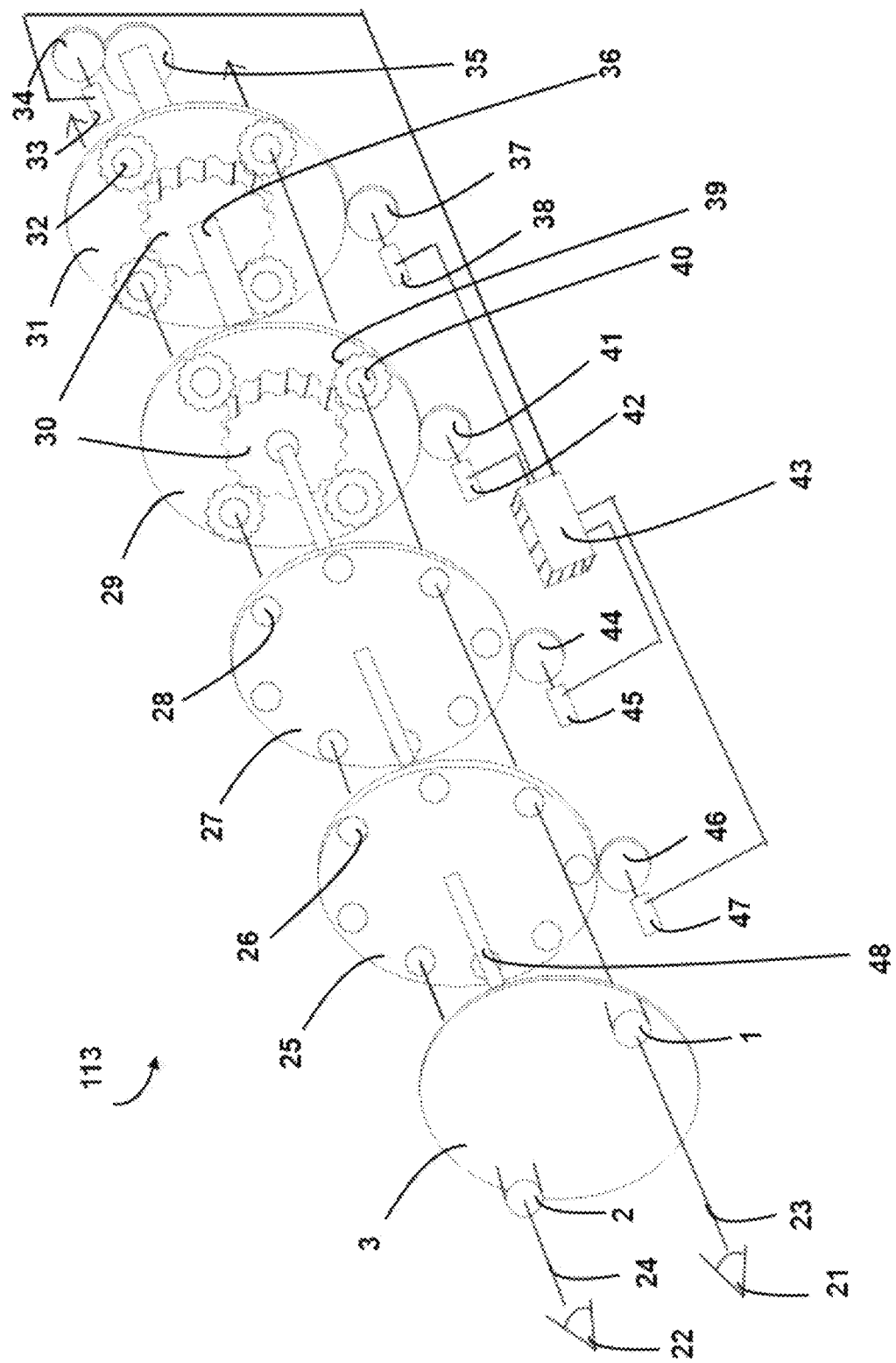
FIG. 4 is a perspective view of the front cover and internal components of a lens chamber in accordance with some embodiments of the invention.

FIG. 4 is a perspective view of a system 113, comprised of a front cover 3 and a plurality of motor driven lenses in accordance with some embodiments of the invention. The system 113 consist of a series of parallel lens disks, each with mounted spherical or cylindrical lens. Variations of phoropters and vision testers; such as those described in U.S. Pat. Nos. 4,385,813 and 5,812,241, the full disclosure of which is incorporated herein by reference, are commonly known to those skilled in the art and include different lens chamber embodiments. Possibilities for lens chamber embodiments are limitless depending on the type and severity of the refractive error conditions being diagnosed or screened. System 113 may comprise a high spherical power (H-SPH) disk 25 with its mounted H-SPH lenses 26; a low spherical power (L-SPH) disk 27 with its mounted L-SPH lenses 28; a high cylindrical power (H-CYL) disk 29 with each of its H-CYL lenses 40 mounted via planet gear cylindrical lens supports 39; a low cylindrical power (L-CYL) disk 31 with each of its L-CYL lenses 32 also mounted via planet gear cylindrical lens supports 39.

System 113 may comprise a common shaft 48 and a hollow shaft 36. The hollow shaft 36 fits around and rotates on the axis of common shaft 48. H-SPH disk 25 and L-SPH disk 27 are suspended by and rotate around the common shaft 48. H-CYL disk 29 and L-CYL disk 31 are suspended by and rotate around the hollow shaft 36. Common shaft 48 and hollow shaft 36 rotate independent of one another and in either direction.

In some embodiments, cylindrical axis may be automatically adjusted by one or more actuators and mechanical mechanisms. Any suitable mechanical mechanism may be utilized. For example, toothed sun gears 30 and hollow shaft disk 35 are both fixed to and in phase with hollow shaft 36. Thus, power from sun gear motor 33 drives a sun gear pinion 34, allowing for rotation of the sun gears 30. Rotation of sun gears 30 cause rotation of the planet gear cylindrical lens supports 39 in the opposite direction. One or more instructions may be generated by a controller and supplied to the one or more actuators for controlling the rotational movement of the H-CYL disk. This particular embodiment allows a user to change the cylindrical axis, though other embodiments may achieve manipulation of the cylindrical axis by different means.

System 113 may comprise one or more actuation units for driving a rotational movement of the H-SPH disk 25, L-SPH disk 27, H-CYL disk 29 and L-CYL disk 31. The actuation unit may comprise an actuator such as a motor and/or mechanical mechanisms. The actuators can each apply a torque to rotate the respective disk about the axis of rotation. Each actuator can be a motor including a rotor and a stator. For example, motor 47 and pinion 46; motor 45 and pinion 44; motor 42 and pinion 41; and motor 38 and pinion 37; which drive rotation of disks 25, 27, 29, and 31, respectively.

The one or more disks may be rotated in either a clockwise direction or a counterclockwise direction or be revolved in either direction. Based on the input command, one or more processors can determine an output torque to be applied to the disk in order to achieve the desired position. The output torque can be determined in a variety of ways, such as using a controller 43. Operating unit and processor 43 interfaces with the hand-held control unit 10 to provide electrical input controls for all motors. For example, motors 47 and 45 may cause H-SPH lenses 26 and L-SPH lenses 28 respectively to rotate into either the left optical path 23 or the right optical path 24. Similarly, motors 42 and 38 may cause H-CYL lenses 40 and L-CYL lenses 32 to revolve in either direction around the sun gears in such a way that the orientation of the axis of each cylindrical lens is the same as each lens passes in front of either the left eye 21 or the right eye 22. In another example, motor 33 may cause rotation in either direction of the cylindrical lenses while they are in front of either eye.

In other embodiments, SSR may be achieved using two parallel lens chambers, each with one eyepiece, similar to a conventional auto-phoropter as described in U.S. Pat. No. 7,874,676 the full reference of which is incorporated herein.

Figure 5:
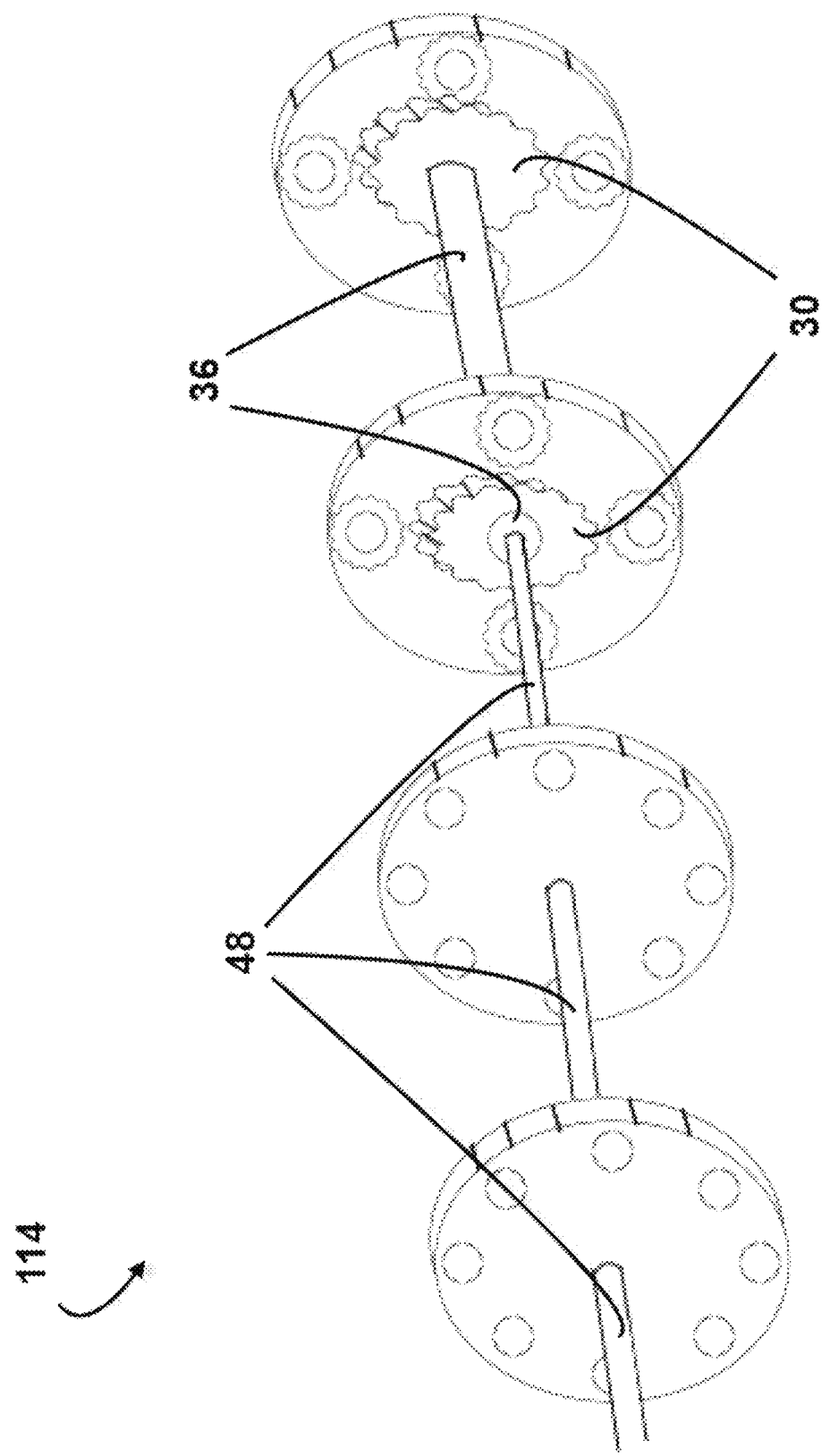
FIG. 5 is a perspective view of internal components of a lens chamber with focus on a linked sun gear mechanism for changing and retaining the cylindrical axis in accordance with some embodiments of the invention.

FIG. 5 is a perspective view of the internal components comprising a linked sun gear mechanism 114 for changing and/or retaining an axis of the cylindrical component during SSR process in accordance with some embodiments of the invention. A linked sun gear mechanism 114 may comprise one or more sun gears 30 which are affixed to and in phase with a hollow shaft 36. In some cases, the hollow shaft 36 may have a relative rotational movement about a common shaft 48. The linked sun gear mechanism 114 may be used to subjectively self-refract for astigmatism. The sun gear mechanism 114 may comprise a single sun gear. The sun gear mechanism may comprise multiple sun gears linked together such that the multiple sun gears are collectively affecting an adjustment of SSR astigmatism. Alternatively, the sun gear mechanism 114 may comprise multiple sun gears rotatable independent of each other. The linked sun gear mechanism may allow a user to change the axis of the cylindrical trial lenses in their optical path. In other embodiments that do not subjectively self-refract for astigmatism, the linked sun gear mechanism may not be necessary.

Figure 6:
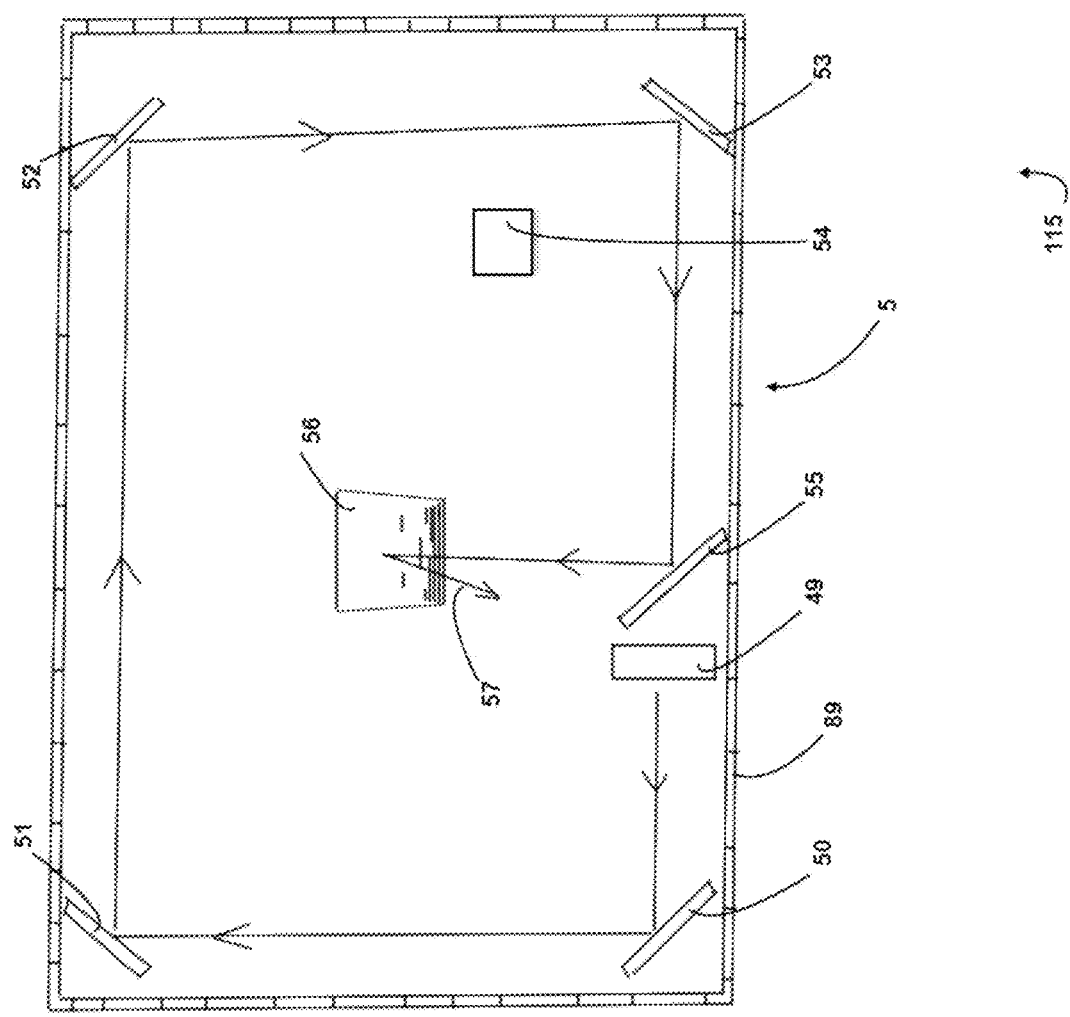
FIG. 6 illustrates a system for creating optical infinity within a compressed space in accordance with some embodiments of the invention.

FIG. 6 illustrates a system 115 for creating optical infinity within a compressed space in accordance with some embodiments of the invention. The system 115 may comprise a mirror box 5. For illustrative purposes, the mirror box 5 has a wall 89. The mirror box 5 may house a digital acuity chart 49. In this embodiment, a digital acuity chart 49 is used for the eye test, however the invention may use any type of eye test such as an illuminated image. A plurality of mirrors may be used to affect an optical path such that the digital acuity chart can be used for testing far vision, near vision and various other vision test. For example, during the SSR process, light rays 57 are emitted from a digital acuity chart 49, which sequentially reflect off a series of mirrors 50, 51, 52, 53, 55, and a rotating mirror 56. The mirrors are specifically spaced and positioned so that the light rays 57 have traveled at least 20 feet or 6 meters which is the standard distance used to represent optical infinity when testing far vision. After leaving mirror box 5, the light rays 57 are refracted by the trial lenses in lens chamber 4 prior to entering the user's eye(s). In some cases, a printer 54 may be housed in the mirror box 5 for printing eye measurements. Alternatively, the printer 54 may be external to the mirror box 5.

FIG. 7A and FIG. 7B illustrate a system 116 that allows a user to switch between distant and near vision tests in accordance with some embodiments of the invention. The system 116 may comprise near vision test light source 60 and a rotating mirror 56. The rotating mirror 56 may have a reflective surface 59 and a near vision test chart 58 on the opposite surface.

FIG. 7A shows a system 116 in a distant vision-testing configuration wherein a rotating mirror 56 is rotated into a position, which allows for reflective surface 59 to reflect optical infinity light rays 57 through trial lenses mounted on optical disks 31, 29, 27 and 25 prior to reaching a user's eye(s). In this configuration, the near vision test light source 60 is turned off.

) FIG. 7B shows a system 116 in a near vision-testing configuration wherein near vision test light source 60 may emit near vision test light rays 100, which are reflected off a near vision test chart 58. The light rays 100 travel through trial lenses mounted on optical disks 31, 29, 27 and 25 prior to reaching the user's eye(s).

In one embodiment, system 116 may be combined with a mirror box 5 and a lens chamber 4, using a rotating mirror 56 with a near vision test chart 58 affixed to one side in order to switch between distant and near vision refraction tests.

Figure 8:
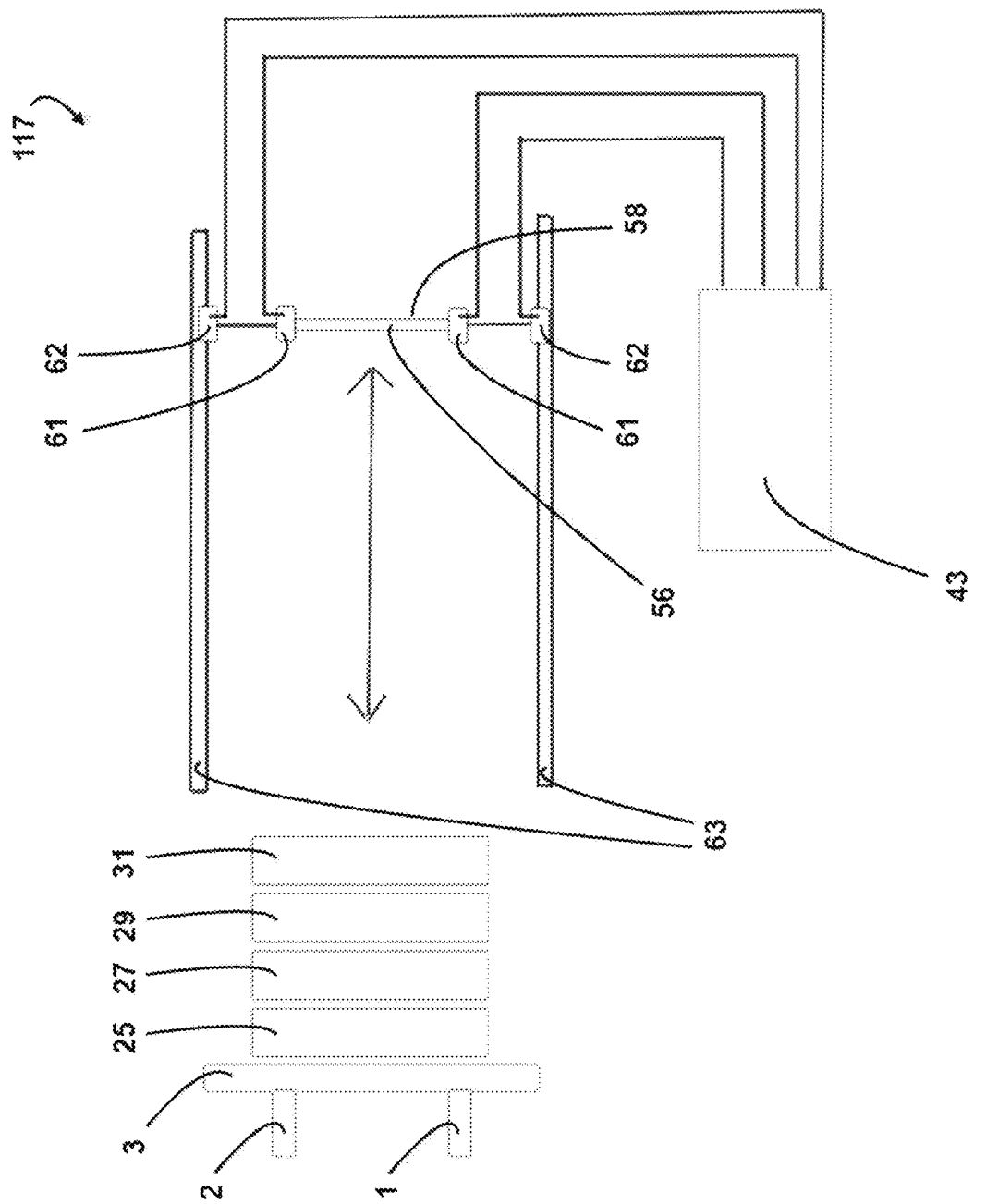
FIG. 8 illustrates a system for switching between near and far vision tests, as well as testing near vision at different distances in accordance with some embodiments of the invention.

FIG. 8 illustrates a system 117 for switching between near and far vision tests, as well as testing near vision at different distances. The system 117 may comprise one or more actuators for actuating a rotational movement of a rotating mirror for switching between near and far vision test. In an example, the system 117 may comprise motor gears 61, motorized ball screws 62 and ball screw guide rails 63. Motor gears 61 may be connected to and rotate a rotating mirror 56 in such a way that it reflects light rays towards the user from a distant vision test such as a mirror box 5. Motor gears 61 may also rotate the rotating mirror 56 in such a way that a posteriorly attached near vision test chart 58 is facing the user when refracting near vision. Near vision may further be refracted at different near distances via motorized ball screws 62 moving a near vision test chart 58 along ball screw guide rails 63.

It is important to understand that a system 117 may be used to place different eye tests at different distances in front of a user's eye(s). For example, a digital acuity chart with test images configured for near and distant vision refraction may be moved along the path of the ball screw guide rails 63.

The actuators may be controlled to drive the rotational movement of the rotating mirror in response to a user command. An operating unit and processor 43 may be configured to generate instructions to the actuator when a user command is received. In some cases, the rotating mirror may be rotated manually or in a non-motorized fashion.

Figure 9A:
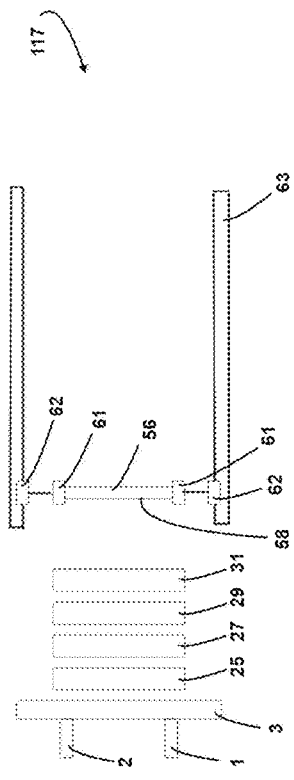
FIGS. 9A-C illustrate a motorized adjusting near vision test system at three common near vision distances encountered in everyday life in accordance with some embodiments of the invention.
Figure 9B:
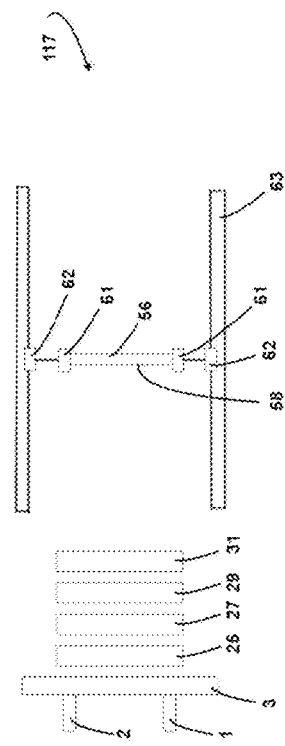
Figure 9C:
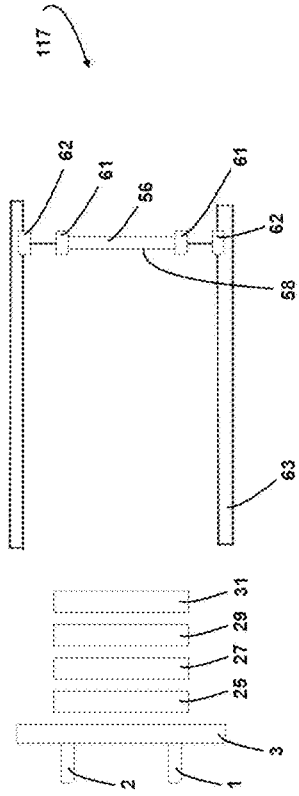

FIGS. 9A-C illustrate a system 117, placing a near vision test chart 58 positioned at multiples distances in accordance with some embodiments of the invention. In some embodiments, the near vision test chart 58 can be positioned at varied distance ranges corresponding to various situations where an eyewear may be used in everyday life. In some embodiments, a distance range may correspond to a common situation where an eyewear can be used. For instance, different distance ranges may correspond to reading glasses used for reading an object at different distances. FIG. 9A depicts a system 117 at a first close distance range for refracting a user's vision. When the near vision test chart 58 is positioned within the first close distance range, the near vision tests may be used for determining reading glasses used for tasks such as sewing, fly-tying, soldering, and the like. FIG. 9B depicts a system 117 at a second near distance range. When the near vision test chart 58 is positioned within the second near distance range, the near vision tests may be used for determining reading glasses used for refracting at book reading distance and the like. FIG. 9C depicts a system 117 at a third near distance range for refracting a user's vision. When the near vision test chart 58 is positioned within the third close distance range, the near vision tests may be used for determining reading glasses used for computer monitor reading distances, music reading distances, such as playing a piano and the like. Various ways may be used for segmenting the near distance ranges. The system 117 may be adjusted or preprogrammed to test at any number of other distances.

In some embodiments, each distance range may comprise a base distance where other distances within the range may be derived from the base distance. The increment within each distance range may or may not be the same. In some cases, a user may be allowed to choose a distance range first then perform the fine adjustment within the distance range. For example, a user may be asked to select from "computer reading glasses," "book reading glasses," "very near vision reading glasses," "standard near vision glasses" or "far vision glasses" and the like. This may provide for an efficient and accurate vision test and enable a user to obtain lenses that meet their vision needs.

In some embodiments, vision test results may be provided according to different distance ranges. In some embodiments, a user may be provided a reading glasses number according to the corresponding distance range. In some cases, the reading glasses number may be provided using different numbering methods when in different distance ranges. For example, to convert a number tested in the standard distance range into a number in the computer reading distance range, the system and supporting software may half the standard near vision number and then round down to the nearest quarter diopter. For instance, if a user measures +2.0 for reading glasses, then for computer glasses, the result may be +1.0. If they were a +2.25, then for computer glasses the result may be +1.0 (half of +2.25 rounded down do the nearest quarter diopter). In another example, if a user measures +2.25 on the standard near vision, the number may be +3.25 for very near vision glasses.

FIGS. 10A-B illustrate a system 117 for testing near and far vision using a digital acuity chart 49 in accordance with some embodiments of the invention. The digital acuity chart may have a configurable operating distance of six feet or less, along with a posteriorly attached near vision test chart 58. The digital acuity chart 49 is rotatable via motor gears 61. FIG. 10A depicts a system 117 in a distance vision refraction configuration wherein a digital acuity chart 49 is facing the user. A near vision test light source 60 is turned off in this configuration. FIG. 10B depicts a system 117 in a near vision refraction configuration with a near vision test chart 58 facing the user. A near vision test light 60 is on in this configuration. In other embodiments a digital acuity chart 49 may be configured with images, which allow for refraction at different near distances and at optical infinity, thus making a near vision test chart 58 obsolete.

Figure 25A:
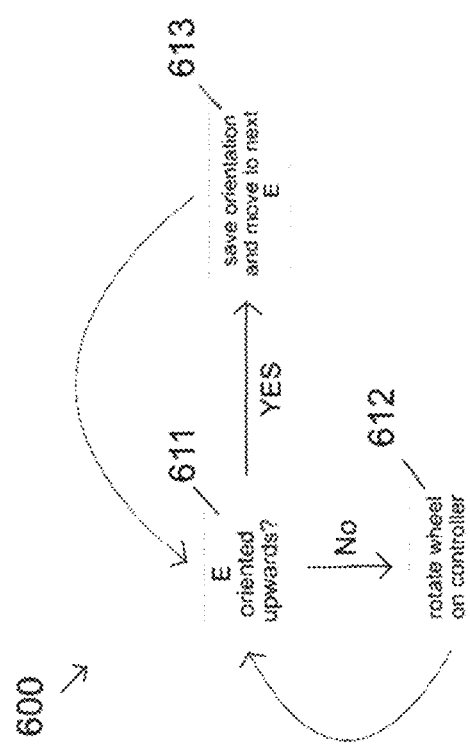
FIGS. 25A-C show an exemplary visual acuity verification system, according to an embodiment of the invention.
Figure 25B:
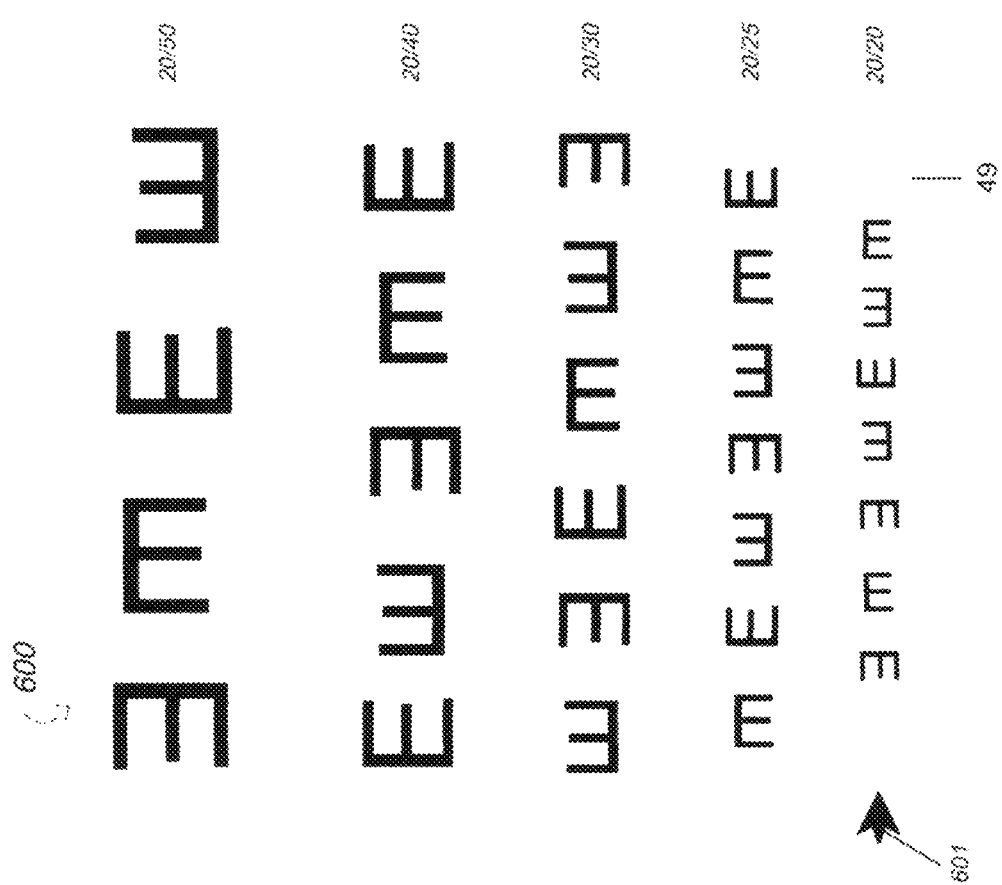
Figure 25C:
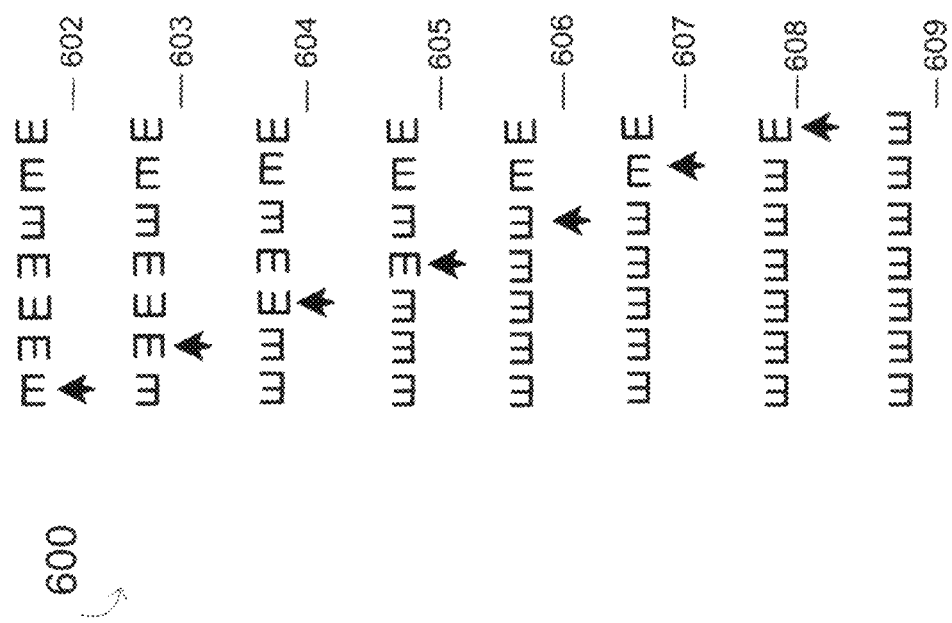

In some embodiments, the system 117 may comprise a visual acuity verification/assessment system for vision self-testing. The FIGS. 25A-C show an exemplary visual acuity verification system 600 in accordance with embodiments of the invention. FIG. 25A shows a flow diagram of the steps and preprogramming involved in a visual acuity verification system 600. System 600's hardware may comprise a digital acuity chart 49, a control unit 10, and operating unit and processor 43. In preferred embodiments, system 600 would thus be incorporated into a system 117, so that visual acuity could be verified as in step 153 of automated SSR system 169. The preprogramming allows the user to verify their visual acuity by first finding the lowest line they can read on a tumbling E chart and then orienting upwards all of the E's for that line. The process starts by first asking the user if a particular E is oriented upwards 611. Though in a preferred embodiment a tumbling E may be used, any letter, shape, icon, emoji, or the like, may be used for the visual acuity verification system.

If the user answers "no" then they are instructed to rotate the wheel on control unit 10 until the E is oriented upward 612. The axis control wheel 70 only rotates one E at a time on the digital acuity chart 49, which displays the tumbling E's. Clockwise rotation of the axis control wheel 70 causes clockwise rotation of the selected E, while counter clockwise rotation of the axis control wheel 70 causes the E to rotate in the opposite direction. The user is instructed to press the X button 67 once the E is oriented upward. Pressing the X button 67 takes the user back to stage 611 in the program, regardless if the E is correctly oriented upwards and the result for that E is saved.

If the user answers "yes" (i.e. the E was already oriented upwards according to the user's vision) then he/she is instructed to press the X button 67, which takes them back to stage 611.

When system 600 is incorporated into system 169, the axis control wheel 70 will not affect the axis of the cylindrical component during this stage of the preprogramming. Once the user has attempted to correctly orient all of the E's for that line, their verified visual acuity results are displayed.

The user may go back to reorient any of the previous E's at any time by pressing the left button 74 as needed. They may use the right button 72 to go forward.

FIG. 25B illustrates how the lowest line that can be read on a tumbling E chart (e.g. 20/20 line) may be selected by using a pointer 601 on a digital acuity chart 49 using system 600. The up button 71 and down button 73 on control unit 10 may be used to make the selection, before confirming the selection by pressing the X button 67.

FIB. 25C illustrates how the sequence of screenshots may look for someone with perfect 20/20 vision after using system 600. Screenshot 602 shows that the first E for that line has been selected. After the user orients the E in the direction that they believe to be upward and presses the X button 67, they are taken to the next E 603. This process continues 604, 605, 606, 607, 608, until the user finishes 609. For a user who selected the 20/20 line in FIG. 25B and then oriented every E correctly as in Fig. C, their verified visual acuity results may be displayed as "20/20 100%" meaning that they were able to correctly read each letter on the 20/20 line. To ensure understanding of the test, the user may be shown a quick tutorial with one very large E that is shown in the upward orientation so that the user knows how to correctly perform the test.

At the end of the automated SSR process some embodiments may provide a mechanism whereby a user's refractive measurements are tested for visual acuity. The SSR system may provide an acuity value along with statistics derived from a visual acuity test such as a level of confidence regarding the acuity measurement or an accuracy percentage a user arrives at from completing an acuity test. For example, 20/20 100% could mean the refractive set of lenses provided by the SSR system allowed a user to correctly identify all 8 out of the 8 letters on the 20/20 line of a Snellen chart. In other embodiments, the visual acuity test can be more generalized to include shapes, images, or characters on a digital acuity monitor or chart. User's that know the alphabet, may simply speak the letters they see on the lowest line of a typical Snellen eye chart form left to right and an input speaker with automated speech recognition software along with preprograming, would detect the number of correct and incorrect responses and provide this as a percentage of correct responses. In other embodiments a user may input one or more responses via an input device, (e.g. speaking responses into a microphone), wherein the one or more responses describes all or parts of a visual test object. A computer (e.g. measurement computer 3000 or SSR unit 3040) then uses the responses to provide a visual acuity measurement along with a representation verifying the accuracy of the visual acuity measurement (e.g. number of correct responses and number of incorrect responses). Thus, the assessment of the accuracy of visual acuity can also be done without needing to orient any images on a digital acuity chart using a hand-held control unit 10. If the accuracy falls below a certain threshold, such as 80%, for example, the system may instruct the user to see an eye care professional and assist with making a referral. In these cases, no vision measurements may be provided. In addition, a visual acuity assessment that includes an accuracy assessment can be performed at the beginning of an SSR process and results can be compared to a second visual acuity assessment at the end of the SSR process. The before and after results may be used to verify visual acuity and the user's improved vision after using the SSR system.

Figure 11:
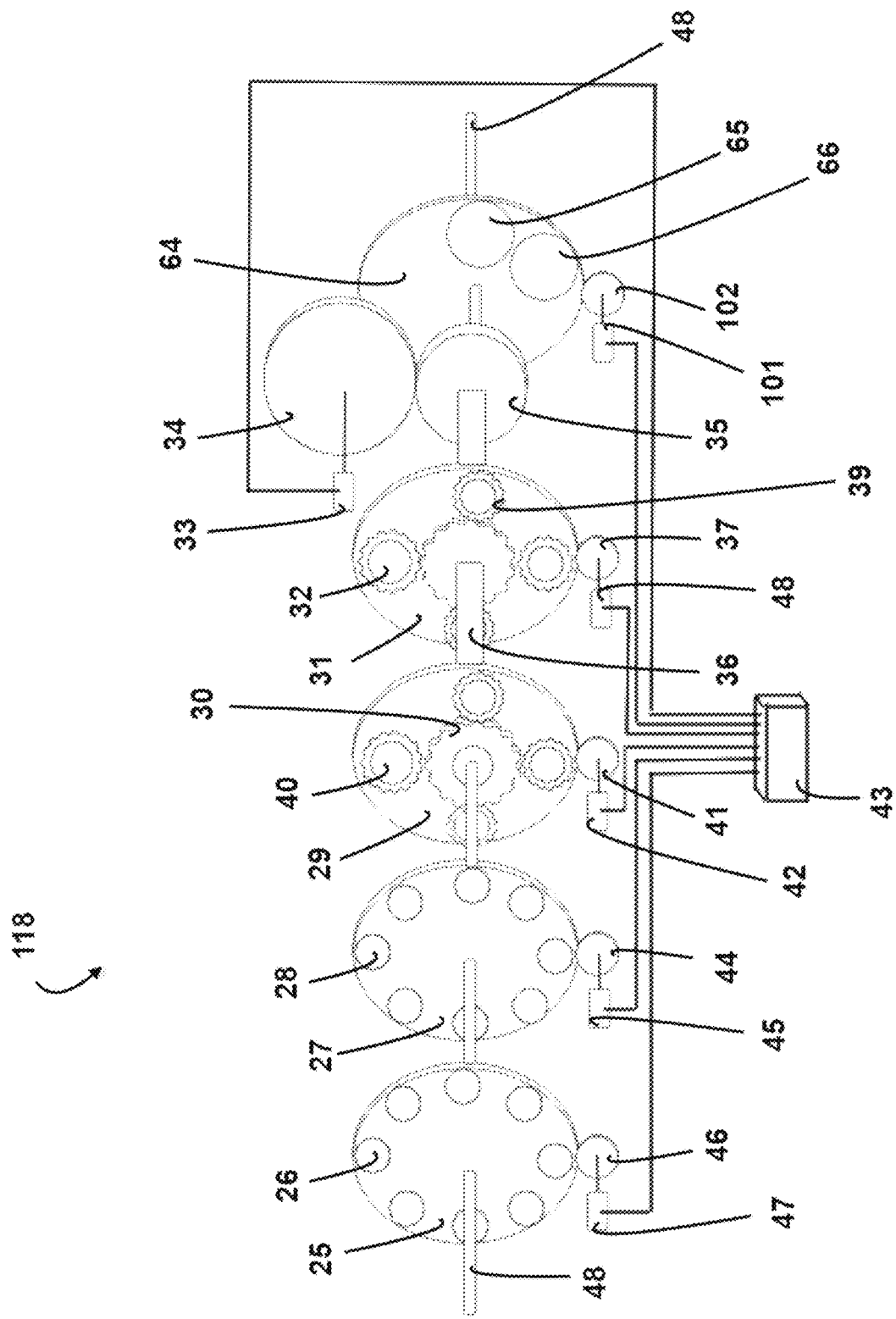
FIG. 11 is an expanded view of some components of a lens chamber with focus on a collimating lens used to create optical infinity within a smaller test space in accordance with some embodiments of the invention.

FIG. 11 illustrates a system 118 for creating parallel light rays for a vision test in accordance with some embodiments of the invention. A collimating lens 65 may be used for creating the parallel light such that distant vision refraction can be performed in a short distance rather than the standard 20 feet or 6 meters. A collimating lens is used to cause divergent light rays to become parallel. Thus, when looking at a near object through a collimating lens, the eye may perceive the near object as being much farther away than it actually is. System 118 may comprise a collimating lens 65 along with a plano lens 66, both of which may be placed on a rotating lens disk 64. A motor 101 and a pinion 102 may power rotation of a lens disk 64. Non-parallel light rays from a vision test placed much closer than the standard 20 feet may enter a collimating lens 65 and then exit with a parallel orientation. Thus, the eye perceives these light rays as emanating from an object placed at optical infinity. After exiting a collimating lens 65, the light rays enter at least one trial lens in the user's optical path. The user then refracts for distant vision using different trial lenses. A plano lens 66 may also be placed on a lens disk 64 for the purpose of allowing the user to switch between distant and near refraction. When switching to near vision refraction, a system 118 would rotate a collimating lens 65 out of a user's optical path and rotate a plano lens 66 into a user's optical path. The user then refracts for near vision using different trial lenses. The digital acuity chart used for distance refraction may remain in the same position or be placed closer to a lens disk 64 during near vision refraction.

FIGS. 12A-B illustrate a system 119 for switching between acuity vision testing and quality vision testing in accordance with some embodiments of the invention. Quality vision testing may comprise having a user viewing real word objects for testing the quality of their vision. System

119 may comprise a visual quality window 88, a window cover 90, and a window cover motor gear 91.

FIG. 12A shows a system 119 in a visual acuity configuration. A pivoting mirror 56 may be positioned in order to reflect optical infinity light rays 57 through at least one trial lens in a user's optical path. The optical infinity light rays 57 may emanate from a series of mirrors within a mirror box; the last mirrors in the series are represented herein by mirrors 55 and 56, respectively. A digital acuity chart, an illuminated eye chart and the like may be used in place of the mirror box and mirror 56. In this particular embodiment, a window cover 90 may be used to block outside light from entering the device. A collimating lens system 118 may be placed between a pivoting mirror 56 and front cover 3 for the purpose of decreasing the space required for distance acuity refraction.

FIG. 12B shows a system 119 in a visual quality configuration. When refracting for visual quality, a pivoting mirror 56 and a window cover 90 may be rotated out of a user's optical path or a user's viewing direction by motor gears 61 and 91, respectively. This allows for visual quality light rays 103 emanating from objects outside of the device to enter the device along a user's optical path.

Various other systems or methods can be used to allow a user to switch between refracting for visual acuity and refracting for visual quality using the provided systems and methods.

FIG. 13A illustrates a refractor 7 wherein a visual quality window 88 has replaced a mirror box 5. In this particular embodiment of a refractor 7, visual quality alone may be tested, however other tests may be added outside a window 88. In some cases, the visual quality window 88 may be part of the wall of a lens chamber 4. For illustrative purposes, the wall of lens chamber 4 has been cross-sectioned along window 88 and labeled.

FIG. 13B and FIG. 13C both illustrate a refractor 7 which may use a system 119 for switching between refraction for visual quality and visual acuity. The refractor 7 may be the same refractor as described FIG. 13A with the addition of a system 119. The system 119 may comprise a pivoting digital acuity monitor 49, a visual quality window 88, and a window cover 99.

FIG. 13B shows a system 119 in the visual quality configuration, wherein a window cover 90 and a digital acuity chart 49 are positioned out of a user's optical path. The window cover and the digital acuity chart may be rotated by the motor gears 61 and 91 respectively.

FIG. 13C illustrates a system 119 in the visual acuity configuration, wherein a window cover 90 blocks any outside light from entering a lens chamber 4 and a digital acuity chart 49 is positioned in a user's optical path. Digital acuity chart 49 and window cover 90 are powered into position again via motor gears 61 and 91, respectively. In this configuration, a digital acuity monitor 49 may be configured with test images for optical infinity and near vision acuity testing. A digital acuity chart 49 may slide closer to the user's eye for near vision refraction via motorized ball screws 62 riding along ball screw guide rails 63. During visual acuity refraction at optical infinity (i.e. light rays emitted from digital acuity monitor travel 20 feet or more before entering a user's eye) and at any more near distance (i.e. light rays emitted from digital acuity monitor travel less than 20 fee before entering a user's eye), optical infinity light rays 57 and near vision test light rays 100, may travel along a user's optical depending on how far a digital acuity chart 49 is positioned from a user's eye.

In other embodiments, a digital acuity monitor 49 may act as a window cover, when switching between visual acuity refraction and visual quality refraction. This may occur by way of a sliding mechanism that keeps a digital acuity monitor 49 tightly fitted against the wall of a refractor 7 as it is positioned over a window 88. This may correspond to the configuration for visual acuity refraction. A digital acuity monitor 49 may be positioned out of the user's optical path exposing a user's eye to a window 88 for visual quality refraction.

FIG. 14 illustrates a table illustrating a plurality of optical elements and their position on each lens disk in accordance with some embodiments of the invention. In addition to a plurality of lenses that may be found on disks inside a lens chamber, there may also be a pinhole occluder added to one of the disks. A pinhole occluder will improve visual deficits caused by refractive errors, but not visual deficits caused by other eye diseases. Thus, a pinhole occluder would be useful as a screening test and as a decision tree, whereby those who do not have improvement of their visual deficit may be referred to an eye care professional.

Figure 15:
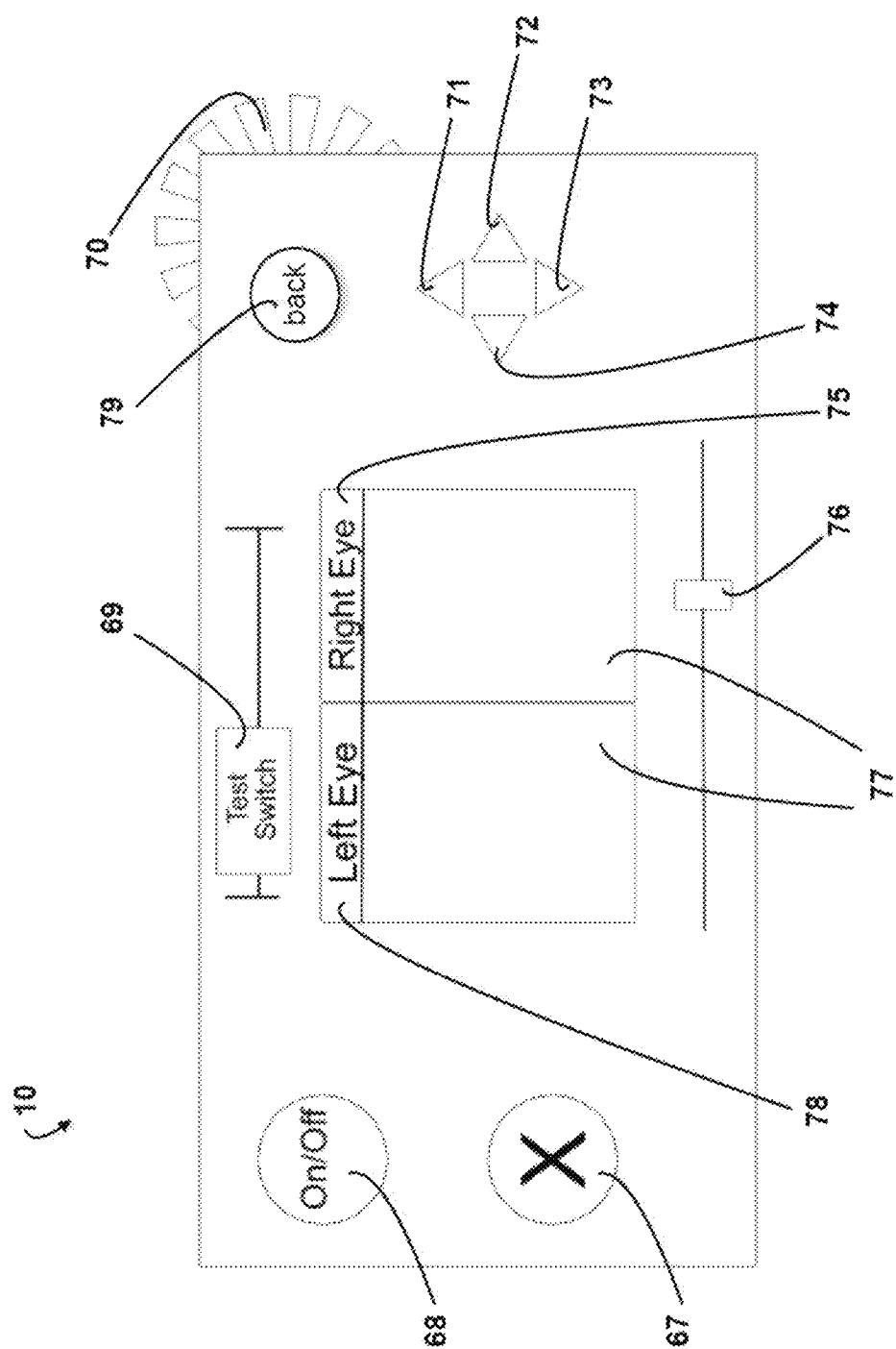
FIG. 15 illustrates the many functions of a control unit in accordance with some embodiments of the invention.

FIG. 15 illustrates a hand-held control unit 10 which a user may interact with during SSR in accordance with some embodiments of the invention. A control unit 10 may comprise an on-off button 68 that turns the invention on or off. In other embodiments, the invention may automatically turn off if left unused for a pre-determined amount of time or turn on using voice command technology. A control unit 10 may comprise an input device such as a test switch 69 that allows a user to select which eye is being tested. In some embodiments, a control unit 10 may comprise an up button 71, which may cause negative 0.25 diopter (D) changes to either the spherical or cylindrical components; and a down button 73, which may cause positive 0.25 D changes to either the spherical or cylindrical components. Various other input devices may be used for a user to input the diopter. For example, a dial may be turned left/right to increase to decrease the diopter. The dial may be snapped in to discrete positions that corresponding to a step in adjusting the diopter. The step or increment for adjusting the diopter may or may not be the same when in different distance ranges. Larger or smaller diopter steps may be used for adjusting the spherical or cylindrical components.

An X button 67 may be used to toggle an up button 71 and a down button 73 between controlling for only changes in the spherical component and controlling for only changes in the cylindrical component. An X button 67 may also be used along with preprogramming, to guide a user through the SSR process. A left button 74 and a right button 72 may be used to provide verification of a user's visual acuity during the SSR process. These buttons may also be used to measure a user's PD. A volume adjuster 76 allows a user to adjust the volume of auditory instructions, which may be transmitted via headphones 9. A back button 79 may allow a user to go back one step in the SSR process.

Figure 16:
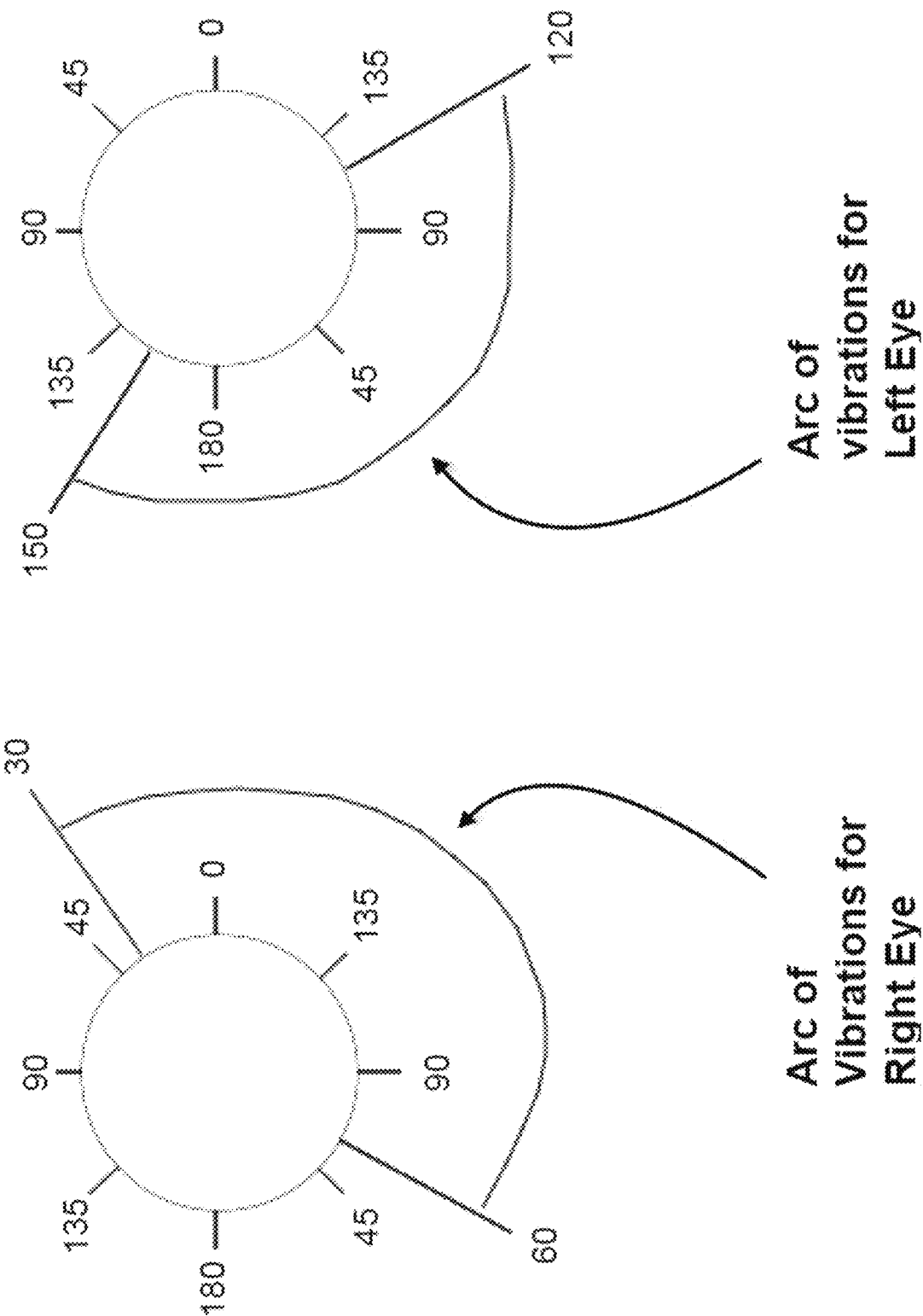
FIG. 16 illustrates the degrees in which a control unit will vibrate when using a control unit to find the cylindrical axis in accordance with some embodiments of the invention.

Cylindrical axis control wheel 70 may be used to make continuous fine-tuned adjustments to the axis of the cylindrical component. A wheel 70 may rotate the axis of the cylindrical component clockwise or counter clockwise, depending on which direction a wheel 70 is rotated. A control unit 10 may vibrate if the user rotates the wheel outside an approximate 180-degree arc which signals a user to rotate the axis control wheel 70 in the opposite direction. This is further illustrated by FIG. 16. The purpose of these vibratory signals is to speed up the process of diagnosis and refracting for astigmatism during the SSR process.

A display screen 77 may be used to display information to a user, such as refractive measurements, PD, VD, and the like. A right eye label 75 and a left eye label 78 may be used to orient a user as to which eye they are currently testing, which depends on the position of test switch 69. Label 75 and 78 may be further used to ensure eye measurements and other data is recorded for the correct eye.

FIG. 17 further illustrates some of the data, which may be displayed on a display screen 77 for each eye. This may comprise refractive measurements, verified acuity data, VD, PD, and the like. A display screen 77 may also comprise other display items such as advertisements, contact information, or other instructional material.

FIG. 18A-C illustrates three different automated systems for measuring the refractor VD. Each system measures the VD from the user's end of an eyepiece 1 or 84, to a series of trial lenses 80.

FIG. 18A illustrates a system 120 comprising voice commands and an eyepiece 1. An eyepiece 1 may have a predetermined length. This predetermined length is used to standardize the VD for each user. During the SSR process, a user is asked to keep their eye snug against an eyepiece 1. Since a user's end of an eyepiece 1 is stationed at a fixed and predetermine length from the trial lenses, a standardized VD for each user can be achieved.

FIG. 18B and FIG. 18C allow for further accuracy when measuring the VD.

FIG. 18B illustrates a system 121 comprising an eyepiece, of which the wall is cross-sectioned and labeled 84 for illustrative purposes. Further comprising a system 121 is a laser emitter 81, lasers beams 82, and a laser detector 83. During SSR, laser beams 82 are intercepted by a user's corneal surface 87. Laser beams 82, which are not intercepted, will become detected by a laser detector 83. The transition point at which lasers start becoming intercepted by corneal surface 87 is used to measure the distance to the trial lenses or the VD.

FIG. 18C illustrates a system 122 comprising a camera 85 and a ruler 86 printed on the inner surface of an eyepiece. A camera 85 may line up a user's corneal surface 87 to a point on a ruler 86. An operating unit and processor 43 may determine the VD so it may be presented on display screen 77.

FIGS. 19A-C illustrates a system 123 in accordance with some embodiments of the invention. The system 123 may comprise a mirror 94, a headrest 95, a motorized ball screw 96, a ball screw guide rail 97, a PD needle 98 and a headrest mount 99.

FIG. 19A illustrates a front view of a system 123, which may be mounted to a front cover 3. A user is instructed to place their forehead against a headrest 95 and close one eye while looking straight into mirror 94 with their other eye. Control unit 10 may be used to move a PD needle 98, so that it is in line with the center of a user's pupil. The provided systems may record the position of the user's first pupil. Next, a user closes their open eye and opens their other eye. A user lines up PD needle 98 with their other pupil. Based on these measurements, the provided system calculates the distance from the previous to the current position of the PD needle 98. This represents the PD, which may be displayed on a display screen 77. In other embodiments with two lens chambers that allow for simultaneous refraction of both eyes, PD distance may be calculated by sliding the lens chambers along a rail, through manual or automated means.

FIG. 19B illustrates a side view of system 123. Headrest mount 99 fastens and stabilizes a headrest 95 to a front cover. For illustrative purposes, the front cover has been cross-sectioned and labeled 93. A ball screw guide rail 97 can be seen mounted to a headrest 95 in this side view. A PD needle 98 can be seen lined up with a right eye 22.

FIG. 19C illustrates a system 123 from a bird's eye view. A motorized ball screw 96 with its attached PD needle 98 (not seen from this view) rides left and right on a ball screw guide rail 97. This is a different view of the same configuration as seen in FIG. 19B. In this view, the same right eye 22 is lined up with a motorized ball screw 96.

Figure 20:
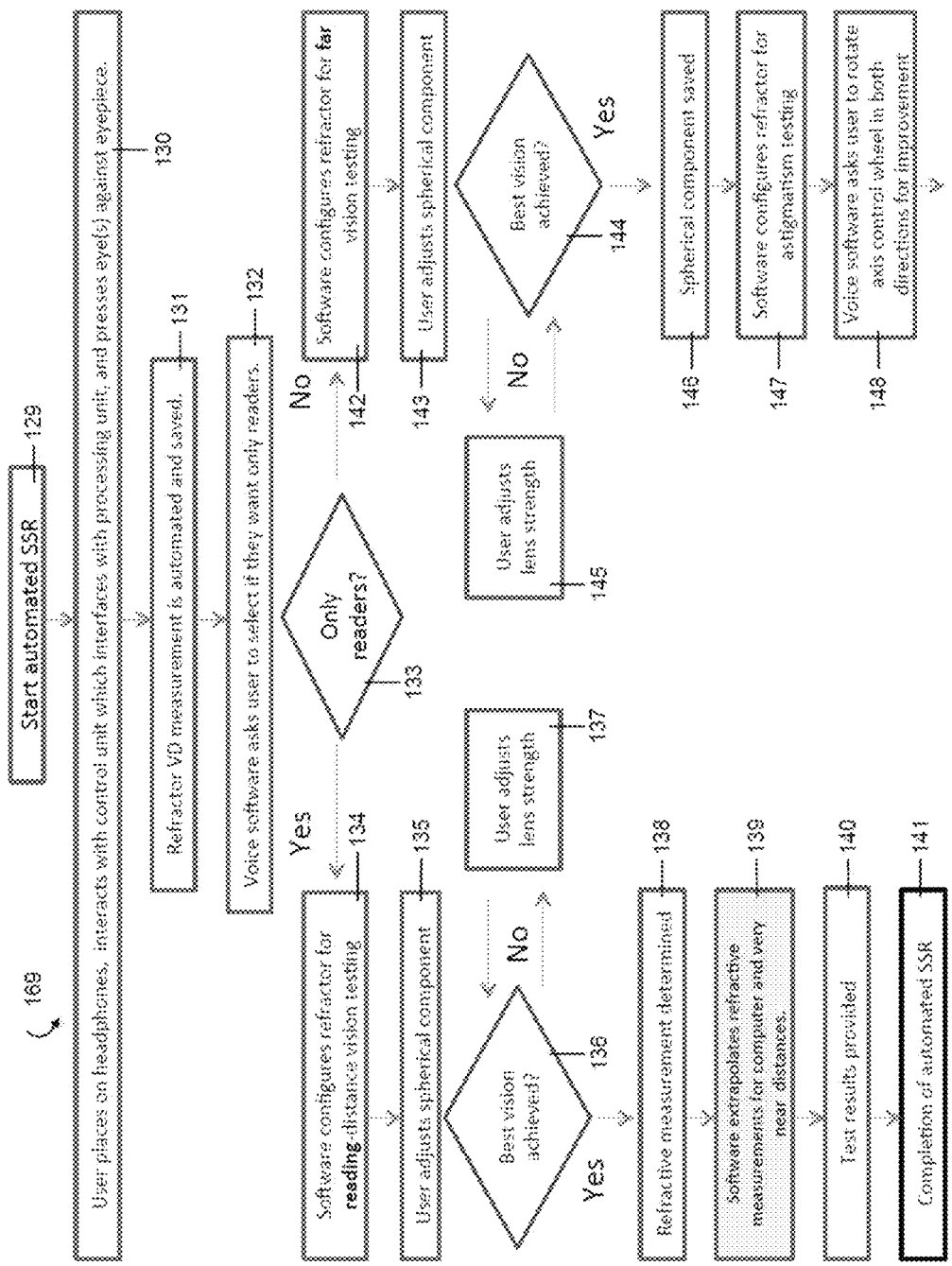
FIG. 20 illustrates a system for directing a user through a comprehensive SSR process in accordance with some embodiments of the invention.

FIG. 20 shows an example of an automated subjective self-refracting (SSR) process using an SSR system 169 in accordance with some embodiments of the invention. The SSR system 169 may comprise a refractor device as described elsewhere herein. The SSR system 169 can be implemented by software, hardware or a combination of both. The automated SSR process may be initiated 129 with a voice command, a user's interaction with a control unit 10, motion detection of a user, and the like. The automated SSR system 169 then sets the user up for SSR 130 by instructing them to apply a set of headphones 9, followed by a quick tutorial on the use of a control unit 10, and finally by having the user apply their eye(s) to eyepiece(s) 1 or 2. Next, system 169 automates and saves the refractor VD 131. The user is then asked by preprogrammed voice commands whether they want only reading glasses only 132. The user may provide input 133. System 169 receives the answer from the user via voice recognition software or control unit input, 10 or the like.

If the user answers "yes," then a refractor 7 is configured for reading-distance vision testing 134. In some embodiments, a user may be further provided options to choose from different distance ranges or reading distances. For example, a user may be asked to choose form "computer reading glasses," "book reading glasses," "very near vision reading glasses," "stand near vision glasses" and the like.

Upon selection of a category, the user may be guided by a series of preprogrammed voice commands, beginning with adjustment of the spherical component 135, followed by subjective self-assessment of visual acuity and/or quality 136. Voice commands instruct the user to keep adjusting the spherical power 137 until best vision is achieved 136. Once best vision is achieved, the exact refractive measurements are determined 138. Special software programming then calculates the appropriate refractive measurements for computer monitor reading distance and very close up working distance 139. The three refractive measurements (i.e. for reading at computer monitor distance, book distance, and very close working distance) are displayed to the user, stored on FOB 8 or transmitted to the user using email, text messaging, web-application or the like 140. The system completes the automated SSR process 141. Completion of the automated SSR process 141 may include but is not limited to allowing the user to receive a prescription, order eye wear, procure eye wear at the location, book an office appointment with an eye care professional or interact with an eye care professional in real time with an audio-video feed.

If the user answers "no" then a refractor 7 is configured for far distance vision testing 142. The user follows a series of preprogrammed voice commands, beginning with adjustment of the spherical component 143, followed by subjective self-assessment of visual acuity and/or quality 144. Voice commands instruct the user to keep adjusting the strength of the spherical component 145 until best vision is achieved 144. Once best vision is achieved, system 169 saves the spherical component refractive measurements 146.

Next, system 169 is configured so that a refractor 7 can test for astigmatism 147. Voice software asks the patient to rotate axis control wheel 70 in both directions 148 and if there is any improvement in vision, to stop on the axis with the clearest vision. Next, the preprogrammed voice instructions ask the user whether or not their vision was improved 149. If the user answers "yes" they are asked to adjust the cylindrical power to check for more visual improvement 150. System 169 now auto-adjusts the spherical component to keep the circle of least confusion on the retina, while changes are made to the cylindrical component. The user is then asked if best vision is achieved 151 and if not, the user continues to adjust the cylindrical lens power and/or axis 152 until best vision is achieved 151. Once best vision is achieved, the user is taken to a novel interactive visual acuity assessment test 153. The user is also taken to the same visual acuity test 153 if they answered "no" to question 149, which excludes the diagnosis of astigmatism.

The visual acuity assessment test 153 is conducted by having the user select the lowest line he/she can read on a digital tumbling E chart. The tests may rely on a user turning an axis control wheel 70 which rotates each of the E's so they all point upwards. When finished, system 169 saves the lowest line that was selected (e.g. the 20/20 line) and the percentage of E's in that line that were correctly oriented to point upwards (e.g. 100%). In this way, the system 169 measures the user's visual acuity and also verifies the result (i.e. as a percentage of the number of correctly oriented E's) without the need for assistance from another person. Next, visual quality is assessed, and the user is instructed to make any needed final adjustments 154.

System 169 then adds positive 0.25 D to the spherical component only if it improves or causes no change in the visual acuity 155. This is to help keep the ciliary muscles in the eye relaxed when looking at near objects.

The user is then asked if they would like bifocals 156. User chooses either "yes" or "no" 157. If the user answers "no" the acuity and refractive measurements for far vision are determined 158. This data is displayed to the user, stored on FOB 8 or transmitted to the user using email, text messaging and the like 159. The system completes the automated SSR process 160. Completion of the automated SSR process 160 may include but is not limited to allowing the user to receive a prescription, order eye wear, procure eye wear at the location, book an office appointment with an eye care professional or interact with an eye care professional in real time with an audio-video feed.

If the user answers "yes," then a refractor 7 is configured for near vision testing 161. The user follows a series of preprogrammed voice commands, beginning with adjustment of the spherical component 162, followed by subjective self-assessment of visual acuity and/or quality 163. Voice commands instruct the user to keep adjusting the strength of the spherical component 164 until best vision is achieved 163. Once best vision is achieved, the far vision acuity along with the far and reading distance vision refractive measurements are determined 165. System 169 extrapolates the refractive measurements for both computer distance work and very near vision work (e.g. fly tying) from the data previously gathered at near distance 166. At the end of an eye test as illustrated in this embodiment, a vision number, measurement, or even a prescription may be provided to the user. The system may further convert or extrapolate the number provided into a different number, measurement or even a prescription for computer glasses or for glasses used for very near vision activities such as for use in soldering or sewing. The system may provide three or even four numbers for vision uses at different ranges for different purposes. These measurements may be provided via software or from calculations taken from a simple chart using a starting measurement by taking ½ the standard near vision number and by rounding down to the nearest quarter diopter. For instance, if a user's starting number is +2.0 D for reading glasses, for example, then for computer glasses the result may be +1.0 D. If their vision measurement was +2.25 D, then for computer glasses, the result may still be +1.0 (half of +2.25 rounded down to the nearest quarter diopter). The system, method and apparatus, along with the supporting software would increase spherical power by +1.0 D for very near vision needs as a starting point such as for soldering or completing other detailed craft works. For example, if a user measures +2.25 for standard near vision, the additional spherical strength needed to complete these works may increase to +3.25 for very near vision glasses. These measurements may be taken in one or both eyes at the same time, through automated or manual means.

This data is displayed to the user, stored on FOB 8 or transmitted to the user using email, text messaging and the like 167. The system then completes the automated SSR process 168. Completion of the automated SSR process 168 may include but is not limited to allowing the user to receive a prescription, order eye wear, procure eye wear at the location, book an office appointment with an eye care professional or interact with an eye care professional in real time with an audio-video feed.

In some embodiments, one or more lens chambers may house minus (concave) spherical lenses, plus (convex) spherical lenses, minus (concave) cylindrical lenses, and plus (convex) cylindrical lenses. This will allow for correction of myopia with or without astigmatism and hyperopia with or without astigmatism. The device may use preprogramming, such that the lenses are auto adjusted to keep a circle of least confusion on a retina, while assessing for astigmatism. This is also known as maintaining the spherical equivalent. Specifically, when cylindrical lenses are added to correct for astigmatism, the focal point of an image may move in front of or behind the retina depending whether the cylindrical lenses are concave (minus) or convex (plus). Adjustments in the spherical component are needed to keep the circle of least confusion or the distorted image from a person's astigmatism near the retina, while cylindrical lenses are changed in order to correct the distortions of the image. For example, if a hyperopic user with astigmatism has plus spherical lenses in front of their eye and they are searching for the best cylindrical lens power, then the preprogramming may provide a set of plus cylindrical lenses wherein the preprogramming may be a mechanism comprising a plurality of programming instructions that when executed by a processor cause the processor to keep a circle of least confusion focused on a retina of a user. The preprogramming may refer to specific strengths of the lenses. For example, as the user iteratively toggles through the plus cylindrical lenses in 0.25 diopter (D) increments the device may automatically remove 0.25 D of plus spherical lens power from the spherical component for every 0.50 D plus cylindrical power that is added. Alternatively, if the lens chamber was designed without plus cylindrical lenses, in order to make the device smaller and to save on manufacturing cost, then the device may add 0.25 D of plus to the spherical component for every 0.50 D of minus added to the cylindrical component. This should be clear to those skilled in the art. These auto-adjustments follow a linear relationship, but other linear relationships with different slopes, or even nonlinear relationships may be used to keep the circle of least confusion focused on the retina. This rule may also be applied to phoropters that are not motorized, wherein the user mechanically makes the lens adjustments by following written or audio instructions.

Figure 22:
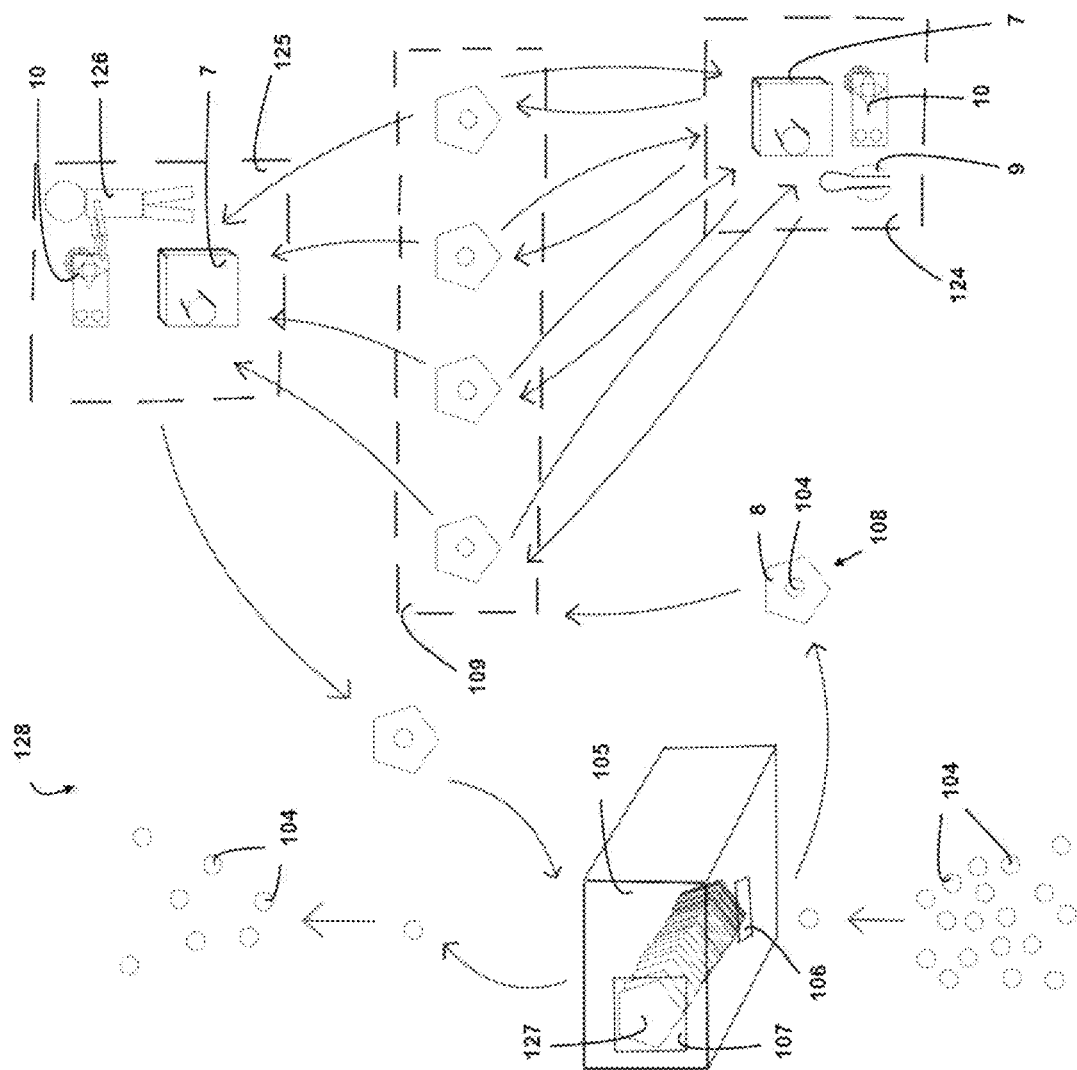
FIG. 22 illustrates a method for using the fob device in accordance with some embodiments of the invention.

FIG. 22 illustrates a system 127 for employing multiple refractions that are facilitated by an eye care professional. The system 127 may comprise a fob 8, a fob receptacle 105, a queue 109, an SSR station 124 and an eye care professional station 125. Fob 8 is a contactless, proximity device that may communicate wirelessly with a refractor 7 when in its proximity. Fob 8 may receive data from a refractor 7, store that data, and then transfer that data to another refractor 7. Together, a fob 8 and a refractor 7 may provide paging capabilities to improve patient flow in an office-based setting by signaling patients to move from a queue 109 to an eye care professional station 125 or an SSR station 124 at the appropriates times. The fob receptacle 105 may be used to keep the fobs in order which ensures that each patient is paged to complete SSR, as appropriate.

In this particular embodiment of a system 127, efficiency is improved when patients 104 grab their own fob 8 from a stack of fobs 127 via a dispensing end 106 of a fob receptacle 105, thereby becoming a patient-fob pair 108. Multiple patient-fob pairs 108 enter a queue 109, whereby each patient 104 waits for a page from their fob 8 to engage in SSR. Next, a refractor 7 at SSR station 124 sends a page to the next patient-fob pair 108 waiting in line at queue 109. The fob 8 signals the patient via any number of sensory cues, to move to SSR station 124, where they undergo the SSR process. In some cases, the fob is configured to convert an alert into a sensory cue and/or message that is picked up by the user. At the end of the SSR process, a refractor 7 sends the eye measurements to the patient's fob 8 for storage and later use. The patient-fob pair 108 moves back to the queue 109 to await a second page. Next, a refractor 7 at eye care professional station 125 sends a page to the next patient-fob pair 108 waiting in the queue. The fob signals the patient to move to eye care professional station 125. Once the patient-fob pair 108 is in close proximity of the refractor 7, the fob 8 transmits the eye measurements to refractor 7 directly, through a local area network, by wireless peer-to-peer means, or the internet. The refractor 7 automatically manipulates its trial lenses to correct for the patient's refractive error based on the custom eye measurements saved on the fob from the SSR process. An eye care professional 126 uses a control unit 10 to make any beneficial changes to the trial lenses prior to preparing a prescription. Finally, the patient-fob pair 108 moves to a fob receptacle 105. The patient places their fob on the stack of fobs 127 through an opening 107 of the fob receptacle 105. The patient then leaves with their prescription.

The functions of a fob 8 are not limited to a fob and may be replaced with a web-based application, a smartphone or tablet device, and the like.

System 127 may be set up in many ways. For example, the eye care professional may control a refractor from a remote location using telemedicine technology. There may be many versions of SSR stations, eye care professional stations and fob receptacles.

Figure 23:
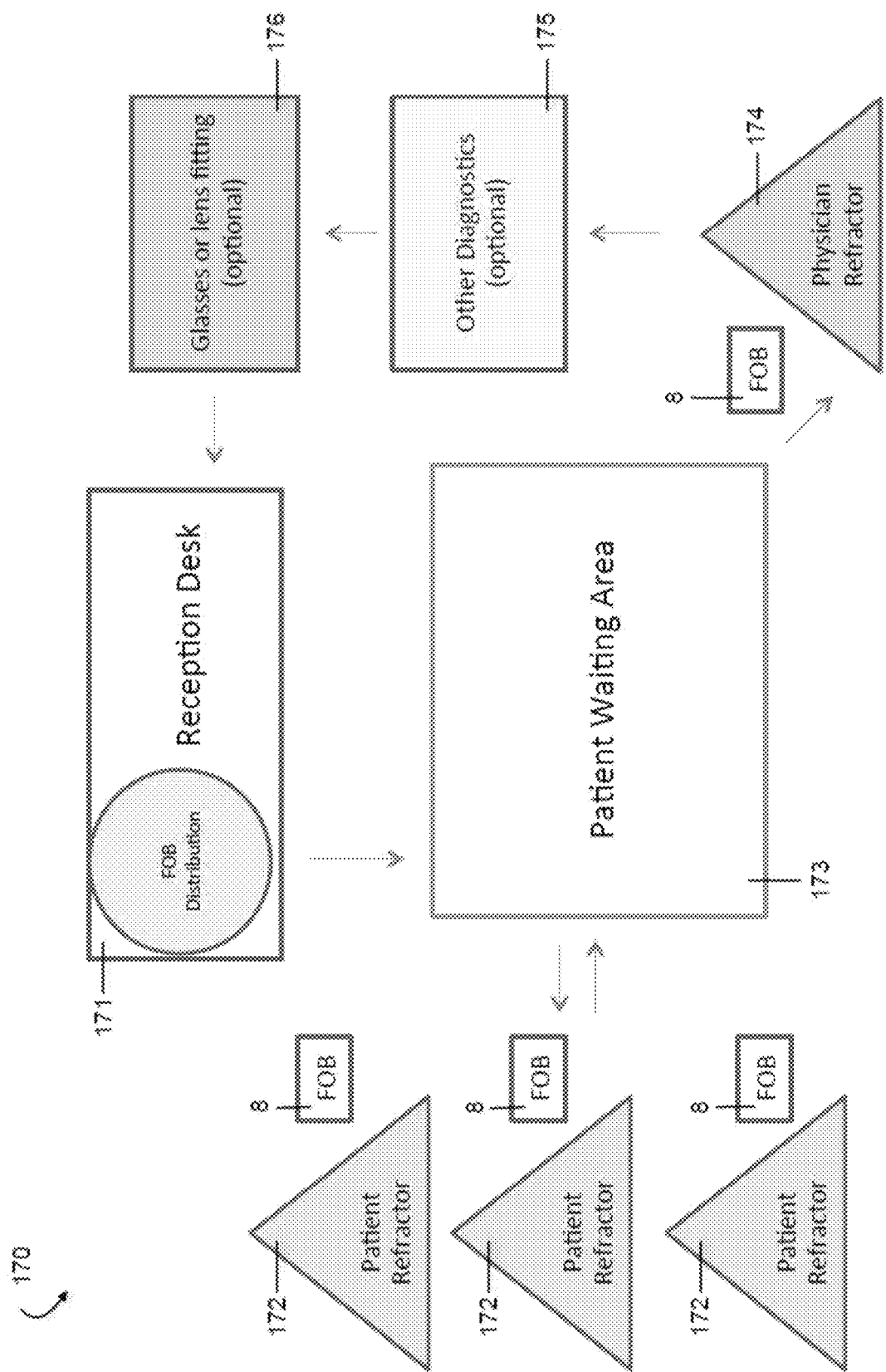
FIG. 23 illustrates a method for using the fob device in accordance with some embodiments of the invention.

FIG. 23 is a flowchart of a high throughput office-based refraction system 170 in accordance with some embodiments of the invention. System 170 may comprise a reception desk with FOB distribution area 171, multiple FOBs 8, multiple patient refractors 172, a patient waiting area 175, a physician refractor 174, other diagnostics 175, and eye wear fitting area 176. Patients are assigned a FOB 8 at the reception desk 171. The patient and FOB 8 then enter patient waiting area 173. When a patient refractor 172 becomes available, the patient refractor 172 pages the next patient in line via their FOB 8. After being alerted by FOB 8, the patient is signaled to use the available patient refractor 172. The patient then utilizes automated SSR system 169. Upon completion of the automated SSR process, the patient refractor 172 wirelessly sends the SSR measurements to the patient's FOB 8 and is signaled back to the patient waiting area 173. When the physician refractor 174 becomes available, the physician refractor 174 pages the next patient in line via their FOB 8. After being alerted by FOB 8, the patient is signaled to physician refractor 174. Once the patient and their FOB 8 reach the physician refractor 174, the FOB 8 automatically and wirelessly sends the SSR measurements to the physician refractor 174, which automatically places the corrected lenses in the optical path of the patient based on the SSR measurement data. An eye care professional may make any needed changes to the eye measurements and run further tests. Next, the patient and FOB 8 are signaled to other diagnostics 175 for more testing if appropriate, then to eye wear fitting 176 if appropriate, and then to the reception desk 171 to drop off the FOB 8 and check out. The FOB 8 is able to also communicate wirelessly with any office based electronic medical records and update the records as needed during the office visit. FOB 8 may also be replaced with a smartphone app that uses contactless technology for communication, such as those used by POS machines (e.g. apple pay).

In other embodiments a video camera communicatively connected to an SSR system may use facial recognition technology, by digital imaging device 3001, to identify a user, match that particular user to a previously saved user profile comprising user-specific information, for example, eye measurements, demographic information, and the like, or create a new user profile for them, then merge the eye measurements and other data to a digital account. These accounts may be stored in a cloud-based service or on a local network. If a user later uses an SSR system that may require an associated user profile, a camera communicatively connected to the system, may automatically recognize the user's face, match that face to a prior account and retrieve stored eye measurements and/or other data auto-adjust, at least, a plurality of lenses based on the retrieved data. Thus, when a medical professional has the patient look through the eye chamber, the patient may be looking through the best set of corrective lenses for each eye respectively based on data comprising, at least, a last refraction. Also, when the user is in another location, a camera at a point of sale may automatically assign correct eye measurements to a set of eye glass frames, contact lenses, or the like, so the user advantageously does not need to remember or bring this information with them to purchase corrective eyewear. The point of sale may also be online using any connected device. Other biometrics, such as a fingerprint may also be used instead of a face. For example, fingerprint biometric data could be captured from the hand-held control unit 10. This system could be used in much the same way as a fob, but in this embodiment, some of steps or inconveniences of FOB 8 may be removed or improved upon. For example, instead of someone needing to assign or dispense a FOB 8 to a user, a user video camera 11 with supporting facial recognition software may evaluate biometric data from the user's face when stepping near the camera 11. This biometric data may then be used to create a new user account or open the user's existing account. New eye measurements, purchases, and the like, may be made before, during, and/or after an SSR process, and the data may be saved to user database 3020, cloud service 3030, or stored in a user device 3010 over network 2810 instead of on a FOB 8. Based on how the faces are saved in order, this order can be used to keep a user's places in line during SSR, later at the point of sale, or while meeting with an eyecare professional, where prescriptions may be signed with a handwritten, electronic or digital signature and the like.

Eye measurements and other unique health related data would be assigned to each patient's account. The eye measurements and other data saved in the cloud may further be used at a later time for automatic adjustments of a plurality of lenses, for purchases, data storage, and the like. In preferred embodiments an SSR system automatically records and stores patient data to a digital account for future use, including for patient usage and for training future ANNs.

Figure 24:
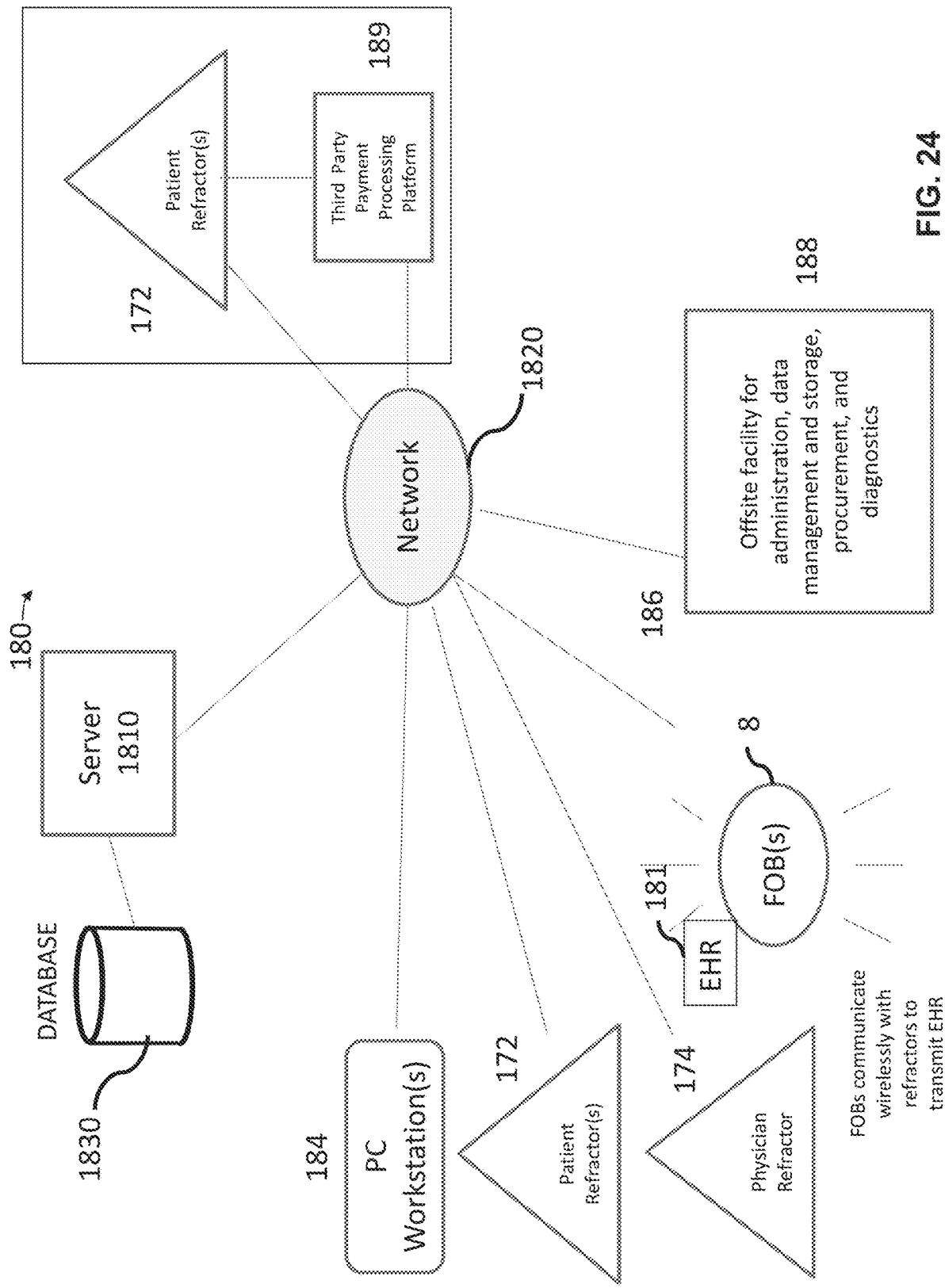
FIG. 24 illustrates an exemplary visual acuity verification system in accordance with embodiments of the invention.

FIG. 24 is a network diagram of system 180 in accordance with some embodiments of the invention. System 180 may comprise a server 1810, a plurality of refractor devices 172, 174, one or more media transportation devices (e.g., fob 8), a network 1820, an offsite facility 188 and optional computing devices 184. Each of the components 172, 174, 184, 1810 and 188 may be operatively connected to one another via network 1820 or any type of communication links that allows transmission of data from one component to another.

In the embodiment of FIG. 24, two-way data transfer capability may be provided between the server and each refractor device. The refractor devices can also communicate with one another via the server (i.e., using a client-server architecture). In some embodiments, the refractor devices can communicate directly with one another via a peer-to-peer communication channel. The peer-to-peer communication channel can help to reduce workload on the server by utilizing resources (e.g., bandwidth, storage space, and/or processing power) of the refractor devices.

The components may be located in any locations. The server 1810 may or may not be located remote to the one or more refractor devices. The patient refractors and physician refractors may or may not be located in the same location. The offsite facility 188 may or may not be located with the one or more refractor devices or the server.

A server may comprise one or more server computers configured to perform one or more operations consistent with disclosed embodiments. In one aspect, a server may be implemented as a single computer, through which a refractor device is able to communicate with other components of the network layout. In some embodiments, a refractor device may communicate with the server through the network. In some embodiments, the server may embody the functionality of one or more SSR systems or methods. In some embodiments, the SSR systems may be implemented inside and/or outside of the server. For example, the SSR systems may be implemented by software and/or hardware components included with the server or remote from the server.

In some embodiments, a refractor device may be directly connected to the server through a separate link (not shown in FIG. 24). In certain embodiments, the server may be configured to operate as a front-end device configured to provide access to one or more SSR system(s) consistent with certain disclosed embodiments. The server may, in some embodiments, utilize the SSR system(s) to process input data from a refractor device in order to generate next voice command, test results and the like. The server may be configured to store the users' data in the database. The server may also be configured to search, retrieve, and analyze (compare) user data and test result or prescription data stored in the database. In some cases, the data and information may include a user's previous vision related data obtained with or without an SSR system.

A server may include a web server, an enterprise server, or any other type of computer server, and can be computer programmed to accept requests (e.g., HTTP, or other protocols that can initiate data transmission) from a computing device (e.g., a user device) and to serve the computing device with requested data. In addition, a server can be a broadcasting facility, such as free-to-air, cable, satellite, and other broadcasting facility, for distributing data. A server may also be a server in a data network (e.g., a cloud computing network).

A server may include known computing components, such as one or more processors, one or more memory devices storing software instructions executed by the processor(s), and data. A server can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods disclosed herein can be implemented in hardware components or combinations of hardware and software such as, for example, ASICs, or special purpose computers. While FIG. 24 illustrates the server as a single server, in some embodiments, multiple devices may implement the functionality associated with the server.

The network may be configured to provide communication between various components of the network layout depicted in FIG. 24. The network may be implemented, in some embodiments, as one or more networks that connect devices and/or components in the network layout for allowing communication between them. For example, as one of ordinary skill in the art will recognize, the network may be implemented as the Internet, a wireless network, a wired network, a local area network (LAN), a Wide Area Network (WANs), Bluetooth, Near Field Communication (NFC), or any other type of network that provides communications between one or more components of the network layout. In some embodiments, the network may be implemented using cell and/or pager networks, satellite, licensed radio, or a combination of licensed and unlicensed radio. The network may be wireless, wired, or a combination thereof.

The SSR system(s) may be implemented as one or more computers storing instructions that, when executed by one or more processor(s), generate a series of command to guide a user in an SSR process, in response to a user input automatically generate instructions to adjust lenses and components of the SSR system to perform one or more operations consistent with disclosed embodiments. The SSR system(s) may further store data generated during the SSR process such as vision test result, prescription and the like. In some embodiments, the server may be the computer in which the SSR system(s) are implemented.

The server may access and execute the SSR system(s) to perform one or more processes consistent with the disclosed embodiments. In certain configurations, the SSR system(s) may be software stored in memory accessible by the server (e.g., in a memory local to the server or remote memory accessible over a communication link, such as the network). Thus, in certain aspects, the SSR system(s) may be implemented as one or more computers, as software stored on a memory device accessible by the server, or a combination thereof. For example, one SSR system may be computer hardware executing one or more SSR components such as the controller for generating instructions to the refractor, and another SSR system may be software that, when executed by the server, performs one or more SSR processes such as generating voice command and interacting with a user.

The refractor devices, the server, and the other component(s) may be connected or interconnected to one or more database(s) 1830. The database(s) may be one or more memory devices configured to store data (e.g., computer commands, instructions, user test result, health records, etc.). Additionally, the database(s) may also, in some embodiments, be implemented as a computer system with a storage device. In one aspect, the database(s) may be used by components of the network layout to perform one or more operations consistent with the disclosed embodiments. In certain embodiments, one or more the database(s) may be co-located with the server or may be co-located with one another on the network. One of ordinary skill will recognize that the disclosed embodiments are not limited to the configuration and/or arrangement of the database(s).

Any of the refractor devices, the server, the database(s), and/or the offsite facility system(s) may, in some embodiments, be implemented as a computer system. Additionally, while the network is shown in FIG. 24 as a "central" point for communications between components of the network layout, the disclosed embodiments are not limited thereto. For example, one or more components of the network layout may be interconnected in a variety of ways, and may in some embodiments be directly connected to, co-located with, or remote from one another, as one of ordinary skill will appreciate. Additionally, while some disclosed embodiments may be implemented on the server, the disclosed embodiments are not so limited. For instance, in some embodiments, other devices (such as one or more user devices) may be configured to perform one or more of the processes and functionalities consistent with the disclosed embodiments, including embodiments described with respect to the server and the SSR system.

In an example, a server 182 may be located in an office-based location 178, connected through a HUB to a router in a local area network (LAN) which wirelessly transmits data. The router is connected to the internet through a firewall. Within the network are one or more patient or physician refractors 174, 175 which communicate wirelessly with FOBs 8 to transmit electronic health records (EHR) 181. The electronic health records (EHR) 181 are transmitted to FOB(s) 8 and physician refractor 174 wirelessly in any network setting. The EHR 181 may also be transmitted to or from patient refractor(s) 172 at any satellite location(s). This system will also allow for appointment booking, updating a patient's eye measurements, ordering glasses, or other health-related necessities through the network.

In another example, all devices may interface with a Personal Computer (PC) workstation 184 through the wireless network in an office-based setting, or even a satellite location which coordinates workflows or stores data on a server 182. The office-based location(s) may utilize automated SSR system 169 and/or high throughput office-based refraction system 170. The satellite location(s) utilize automated SSR system 169 and may be used with or without an appointment by patients or non-patients. The satellite location(s) provides the general public with 24-hour access to the automated SSR system 169, allows eye care professionals to advertise and book appointments, and allows patients and eye care professionals to interface remotely with an audio-video feed via the Internet 1820. Satellite locations may be housed in retail stores or centers, or other high foot traffic areas. Since satellite locations will generally be unmanned in many embodiments, payment may be taken through a third-party payment processing platform (189), such as Square Pay, Apple Pay, Samsung pay, PayPal, and the like. The FOB(s) 8 may also be taken with users to each satellite location for the purpose of wirelessly auto-transmitting previous eye measurements in order for the patient refractor 172 to automatically place the correct refractive lenses in the user's optical path. Data may also be saved on the FOB(s) 8 for later use at office-based locations. Alternatively, other devices such as a user device (e.g., smart phones, cell phones, personal digital assistants (PDAs), tablets and other portable devices, smartwatches and other wearable devices) may be used for storing and transmitting the data among the office based or satellite locations. FOB 8 in office based, or satellite locations. EHR 181 information may also be distributed via an email platform.

In some cases, given the critical nature of EHR 181, network complexities, requirements for user interface, needed software updates, and patient-physician interface, it may be appropriate to establish an offsite administrative facility 188, or headquarters in a remote location for data management, and storage, system and network administration, procurement, and diagnostics. In some embodiments, this facility will interface with an office-based location through a firewall, or a satellite location through a virtual private network (VPN) 1820. Other security measures may also be taken to secure the network and preserve EHR 181.

Figure 26:
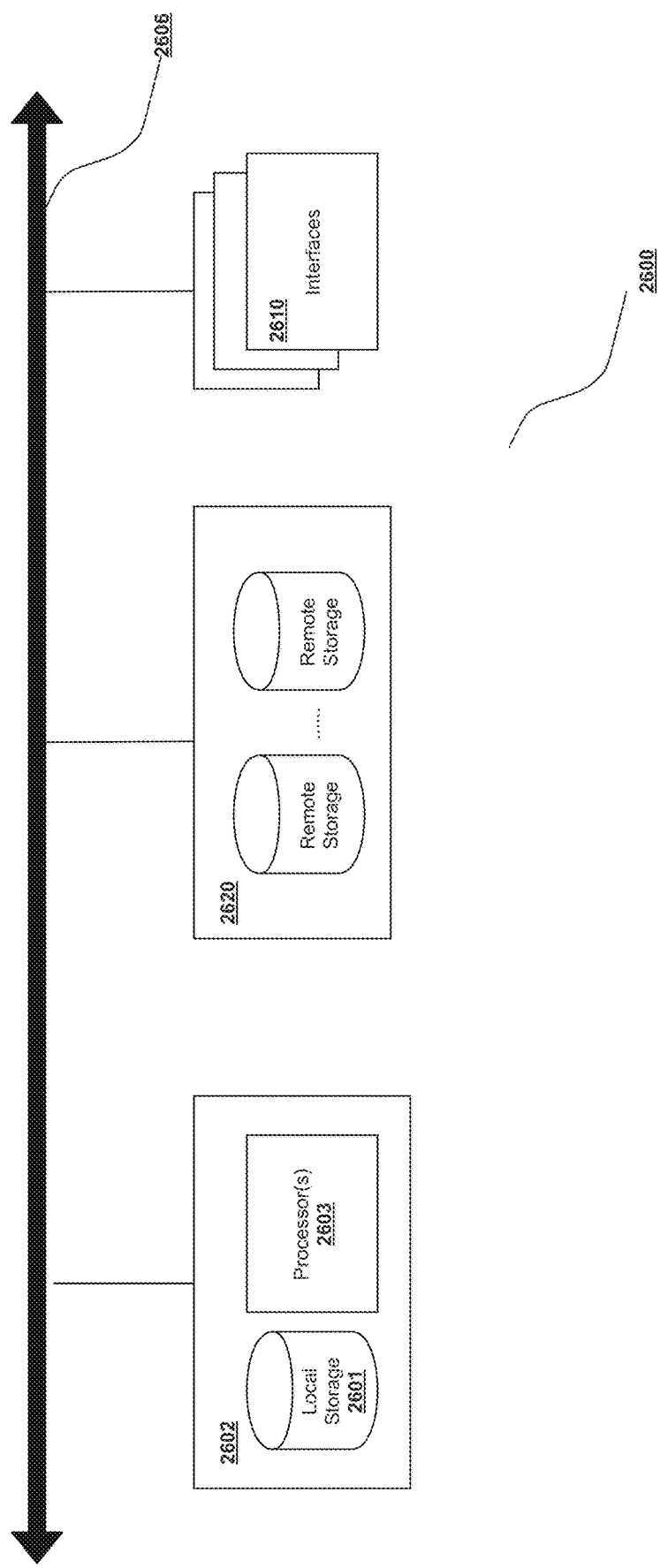
FIG. 26 is a block diagram illustrating an exemplary hardware architecture of a computing device used in an embodiment of the invention.

Referring now to FIG. 26, there is shown a block diagram depicting an exemplary computing device 2600 suitable for implementing at least a portion of the features or functionalities disclosed herein. It should be noted that FIGS. 26-29 comprise another embodiment to at least some of the components disclosed in FIG. 24, and components of FIG. 4. Accordingly, computing device 2600 may be, for example, any one of the computing machines listed in the previous paragraph, or indeed any other electronic device capable of executing software- or hardware-based instructions according to one or more programs stored in memory. Computing device 2600 may be adapted to communicate with a plurality of other computing devices, such as clients or servers, over communications networks such as a wide area network a metropolitan area network, a local area network, a wireless network, the Internet, or any other network, using known protocols for such communication, whether wireless or wired.

In one embodiment, computing device 2600 includes one or more central processing units (CPU) 2602, one or more interfaces 2610, and one or more busses 2606 (such as a peripheral component interconnect (PCI) bus). When acting under the control of appropriate software or firmware, CPU 2602 may be responsible for implementing specific functions associated with the functions of a specifically configured computing device or machine. For example, in at least one embodiment, a computing device 2600 may be configured or designed to function as a server system utilizing CPU 2602, local memory 2601 and/or remote memory 2620, and interface(s) 2610. In at least one embodiment, CPU 2602 may be caused to perform one or more of the different types of functions and/or operations under the control of software modules or components, which for example, may include an operating system and any appropriate applications software, drivers, and the like.

CPU 2602 may include one or more processors 2603 (also herein referred to as processor 43) such as, for example, a processor from one of the Intel, ARM, Qualcomm, and AMD families of microprocessors. In some embodiments, processors 2603 may include specially designed hardware such as application-specific integrated circuits (ASICs), electrically erasable programmable read-only memories (EEPROMs), field-programmable gate arrays (FPGAs), and so forth, for controlling operations of computing device 2600. In a specific embodiment, a local memory 2601 (such as non-volatile random-access memory (RAM) and/or read-only memory (ROM), including for example one or more levels of cached memory) may also form part of CPU 2602. However, there are many different ways in which memory may be coupled to system 2600. Memory 2601 may be used for a variety of purposes such as, for example, caching and/or storing data, programming instructions, and the like. It should be further appreciated that CPU 2602 may be one of a variety of system-on-a-chip (SOC) type hardware that may include additional hardware such as memory or graphics processing chips, such as a Qualcomm SNAP-DRAGON™ or Samsung EXYNOS™ CPU as are becoming increasingly common in the art, such as for use in mobile devices or integrated devices.

In some embodiments CPU 2602, processor 43, and/or processors 2603 may be comprised of one or more Graphical Processing Units (GPUs) to function as a single instruction multiple data (SIMD) architecture whereby multiple processing elements perform the same operation on multiple data points simultaneously. Accordingly, an exploitation of data level parallelism is employed in certain embodiments of the invention to facilitate a faster processing speed.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one embodiment, interfaces 2610 are provided as network interface cards (NICs). Generally, NICs control the sending and receiving of data packets over a computer network; other types of interfaces 2610 may for example support other peripherals used with computing device 2600. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (Wi-Fi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 2610 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 26 illustrates one specific architecture for a computing device 2600 for implementing one or more of the inventions described herein, it is by no means the only device architecture on which at least a portion of the features and techniques described herein may be implemented. For example, architectures having one or any number of processors 2603 may be used, and such processors 2603 may be present in a single device or distributed among any number of devices. In one embodiment, a single processor 2603 handles communications as well as routing computations, while in other embodiments a separate dedicated communications processor may be provided. In various embodiments, different types of features or functionalities may be implemented in a system according to the invention that includes a client device (such as a tablet device or smartphone running client software) and server systems (such as a server system described in more detail below).

Regardless of network device configuration, the system of the present invention may employ one or more memories or memory modules (such as, for example, remote memory block 2620 and local memory 2601) configured to store data, program instructions for the general-purpose network operations, or other information relating to the functionality of the embodiments described herein (or any combinations of the above). Program instructions may control execution of or comprise an operating system and/or one or more applications, for example. Memory 2620 or memories 2601, 2620 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a Java™ compiler and may be executed using a Java virtual machine or equivalent, or files containing higher level code that may be executed by the computer using an interpreter (for example, scripts written in Python, Perl, Ruby, Groovy, or any other scripting language).

Figure 27:
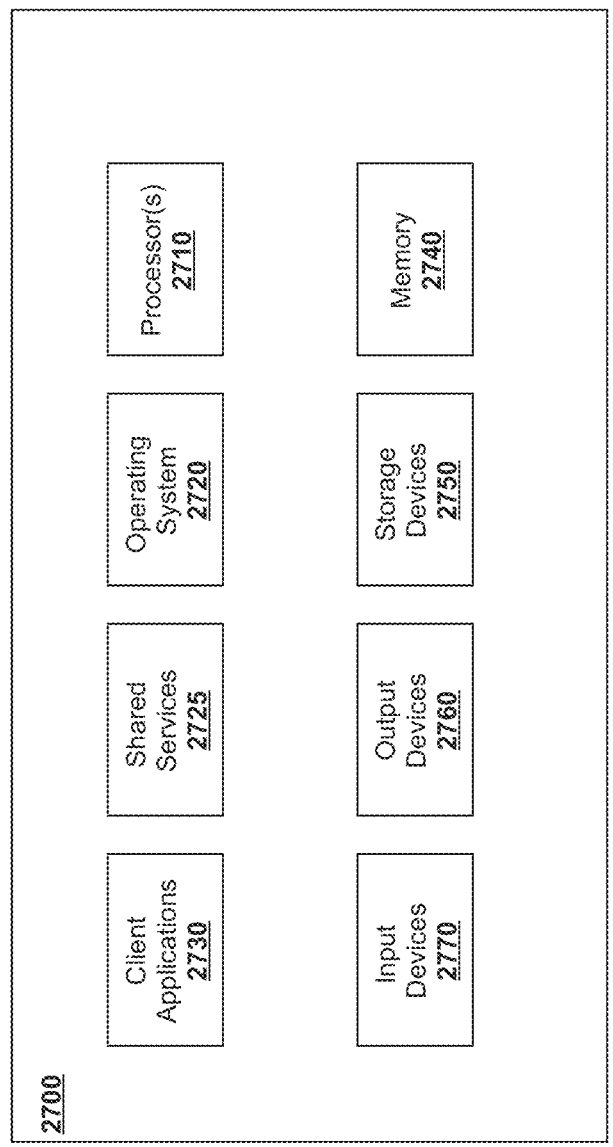
FIG. 27 is a block diagram illustrating an exemplary logical architecture for a client device, according to an embodiment of the invention.

In some embodiments, systems according to the present invention may be implemented on a standalone computing system. Referring now to FIG. 27, there is shown a block diagram depicting a typical exemplary architecture of one or more embodiments or components thereof on a standalone computing system. Computing device 2700 includes processors 2710 that may run software that carry out one or more functions or applications of embodiments of the invention, such as for example a client application 2730. In a preferred embodiment, processor 2710 works in conjunction with processor 43 (referring to FIG. 4). In some embodiments, processor 2710 is used in place of processor 43 and is capable of performing the same functions. Processors 2710 may carry out computing instructions under control of an operating system 2720 such as, for example, a version of Microsoft's WINDOWS™ operating system, Apple's Mac OS/X or iOS operating systems, some variety of the Linux operating system, Google's ANDROID™ operating system, or the like. In many cases, one or more shared services 225 may be operable in system 2700 and may be useful for providing common services to client applications 2730. Services 2725 may for example be WINDOWS™ services, user-space common services in a Linux environment, or any other type of common service architecture used with operating system 2710. Input devices 2770 may be of any type suitable for receiving user input, including for example a keyboard, touchscreen, microphone (for example, for voice input), mouse, touchpad, trackball, or any combination thereof. Output devices 2760 may be of any type suitable for providing output to one or more users, whether remote or local to system 2700, and may include for example one or more screens for visual output, speakers, printers, touchscreens, or any combination thereof. Memory 2740 may be random-access memory having any structure and architecture known in the art, for use by processors 2710, for example to run software. Storage devices 2750 may be any magnetic, optical, mechanical, memristor, or electrical storage device for storage of data in digital form (such as those described above, referring to FIG. 26). Examples of storage devices 2750 include flash memory, magnetic hard drive, CD-ROM, and/or the like.

Figure 28:
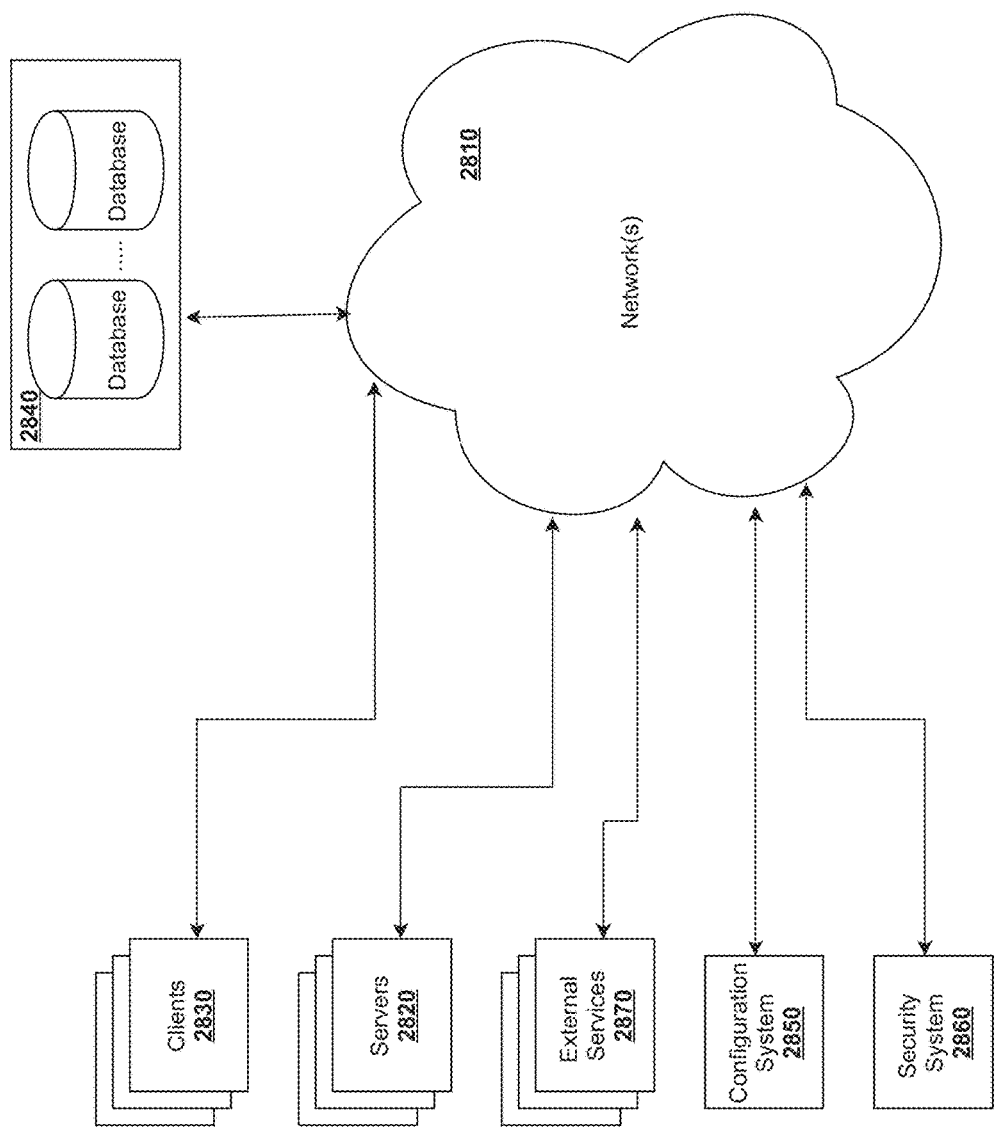
FIG. 28 is a block diagram showing an exemplary architectural arrangement of clients, servers, and external services, according to an embodiment of the invention.

In some embodiments, systems of the present invention may be implemented on a distributed computing network, such as one having any number of clients and/or servers. Referring now to FIG. 28, there is shown a block diagram depicting an exemplary architecture 2800 for implementing at least a portion of a system according to an embodiment of the invention on a distributed computing network. According to the embodiment, any number of clients 2830 may be provided. Each client 2830 may run software for implementing client-side portions of the present invention; clients may comprise a system 2700 such as that illustrated in FIG. 27. In addition, any number of servers 2820 may be provided for handling requests received from one or more clients 2830. Clients 2830 and servers 2820 may communicate with one another via one or more electronic networks 2810, which may be in various embodiments any of the Internet, a wide area network, a mobile telephony network (such as CDMA or GSM cellular networks), a wireless network (such as Wi-Fi, WiMAX, LTE, and so forth), a local area network (or indeed any network topology known in the art; the invention does not prefer any one network topology over any other) or BLUETOOTH™ technology. Networks 2810 may be implemented using any known network protocols, including for example wired and/or wireless protocols.

In addition, in some embodiments, servers 2820 may call external services 2870 when needed to obtain additional information, or to refer to additional data concerning a particular call. Communications with external services 2870 may take place, for example, via one or more networks 2810. In various embodiments, external services 2870 may comprise web-enabled services or functionality related to or installed on the hardware device itself. For example, in an embodiment where client applications 2830 are implemented on a smartphone or other electronic device, client applications 2830 may obtain information stored in a server system 2820 in the cloud or on an external service 2870 deployed on one or more of a particular enterprise's or user's premises.

In some embodiments of the invention, clients 2830 or servers 2820 (or both) may make use of one or more specialized services or appliances that may be deployed locally or remotely across one or more networks 2810. For example, one or more databases 2840 may be used or referred to by one or more embodiments of the invention. It should be understood by one having ordinary skill in the art that databases 2840 may be arranged in a wide variety of architectures and using a wide variety of data access and manipulation means. For example, in various embodiments one or more databases 2840 may comprise a relational database system using a structured query language (SQL), while others may comprise an alternative data storage technology such as those referred to in the art as "NoSQL" (for example, Hadoop Cassandra, Google Bigtable, and so forth). In some embodiments, variant database architectures such as column-oriented databases, in-memory databases, clustered databases, distributed databases, or even flat file data repositories may be used according to the invention. It will be appreciated by one having ordinary skill in the art that any combination of known or future database technologies may be used as appropriate, unless a specific database technology or a specific arrangement of components is specified for a particular embodiment herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, most embodiments of the invention may make use of one or more security systems 2860 and configuration systems 2850. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments of the invention without limitation, unless a specific security 2860 or configuration system 2850 or approach is specifically required by the description of any specific embodiment.

Figure 29:
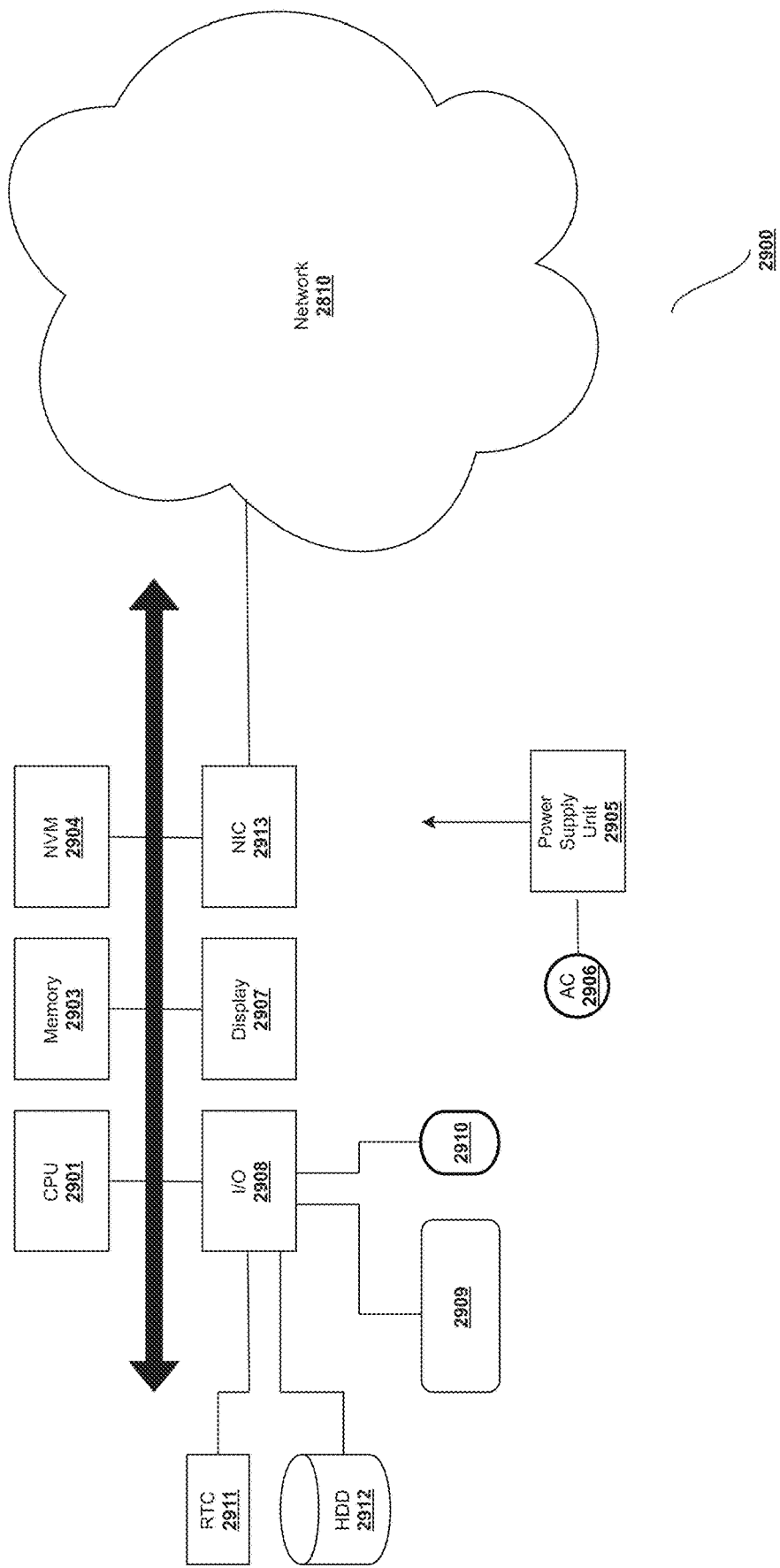
FIG. 29 is another block diagram illustrating an exemplary hardware architecture of a computing device used in various embodiments of the invention.

FIG. 29 shows an exemplary overview of a computer system 2900 as may be used in any of the various locations throughout the system. It is exemplary of any computer that may execute code to process data. Various modifications and changes may be made to computer system 2900 without departing from the broader spirit and scope of the system and method disclosed herein. CPU 2901 is connected to bus 2902, to which bus is also connected memory 2903, non-volatile memory 2904, display 2907, I/O unit 2908, and network interface card (NIC) 2913. I/O unit 2908 may, typically, be connected to keyboard 2909, pointing device 2910, hard disk 2912, and real-time clock 2911. NIC 2913 connects to network 2914, which may be the Internet or a local network, which local network may or may not have connections to the Internet. Also shown as part of system 2900 is power supply unit 2905 connected, in this example, to ac supply 2906. Not shown are batteries that could be present, and many other devices and modifications that are well known but are not applicable to the specific novel functions of the current system and method disclosed herein. It should be appreciated that some or all components illustrated may be combined, such as in various integrated applications (for example, Qualcomm or Samsung SOC-based devices), or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various embodiments, functionality for implementing systems or methods of the present invention may be distributed among any number of client and/or server components. For example, various software modules may be implemented for performing various functions in connection with the present invention, and such modules may be variously implemented to run on server and/or client components.

Figure 30:
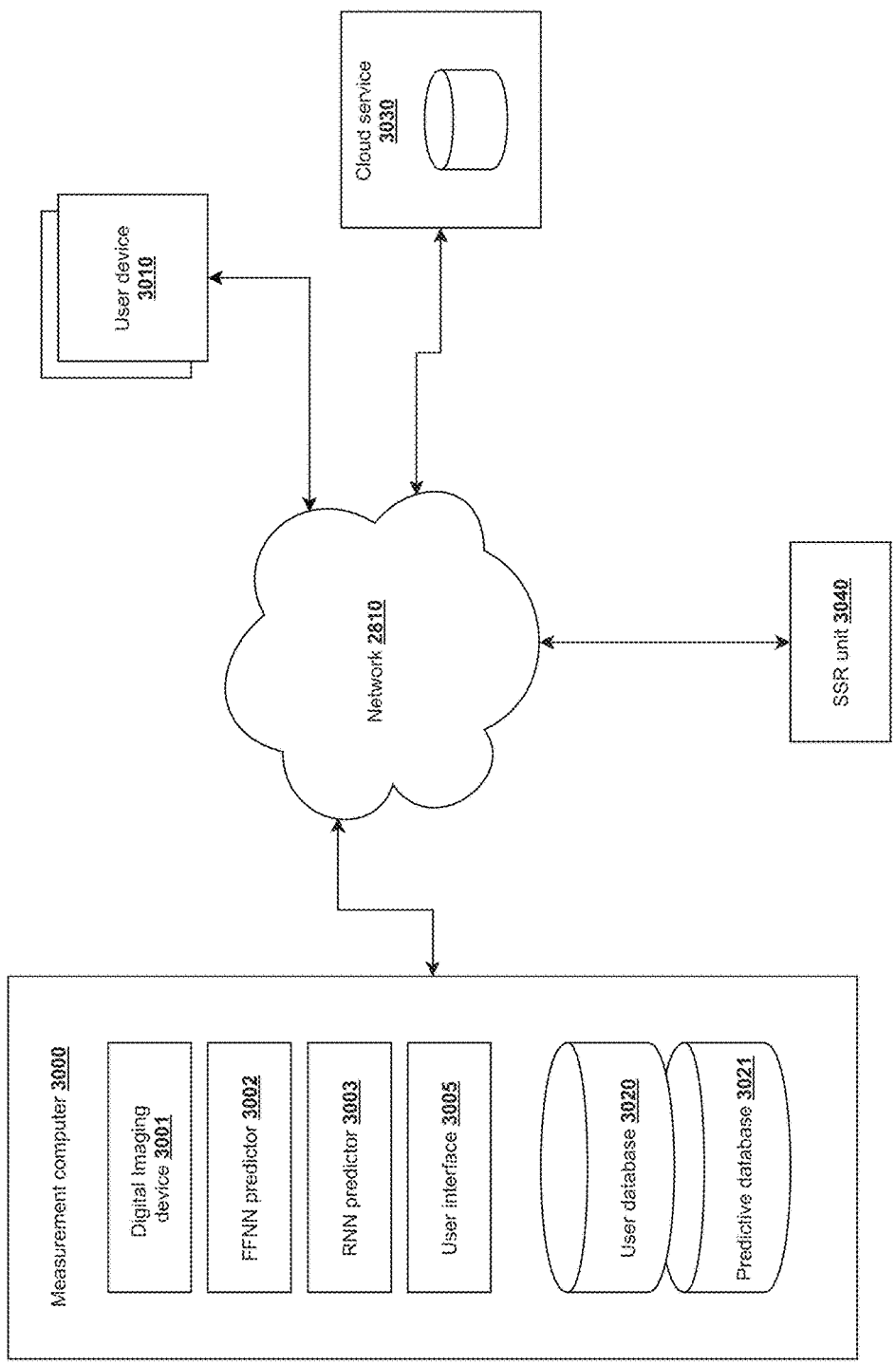
FIG. 30 is a is a block diagram illustrating a system for automating eye measurements, according to a preferred embodiment of the invention.

FIG. 30 is a block diagram illustrating a system for automating eye measurements, according to a preferred embodiment of the invention. According to the embodiment, measurement computer 3000 comprises, at least, memory 2903, processor 2901, and a plurality of programming instructions, the plurality of programming instructions when executed by processor 2901 cause the processor to automate eye measurements comprising: digital image device 3001 to capture images of a user of SSR unit 3040, for example, to receive a digital profile associated with the user from user database 3020, cloud service 3030, or stored in a user device 3010 over network 2810; FFNN predictor 3002 may be used to predict a starting point for a spherical component during an SSR process with a specific number of inputs, outputs, number of layers, activation functions and the like. According to a preferred embodiment, an FFNN may be used to predict a spherical starting component for SSR using SSR unit 3040. Measurement computer 3000 further comprises RNN predictor 3003 may be used to find a user's spherical and/or cylindrical component during an SSR process in accordance with some embodiments of the invention (referring to FIG. 34); user interface 3005 may be used to retrieve data from network sources such as from user device 3010, or from some other network connected device or service; cloud service 3030 may be used as a network-accessible data store or as an application server to provide user profile and predictive information to a plurality of distributed SSR units 3040 (for example, as disclosed in FIG. 37); cloud service 3030 may comprise a user database 3020, predictive database 3021, and the like; user database 3020 may be used to store user (also herein referred to as patient) profile information which may comprise previous eye measurements, past eye prescriptions, demographic information, or other information associated with a user; predictive database 3021 may be used to store patient/user data (i.e. develop a training dataset) after each user completes a SSR process so the data can later be used to train ANNs as illustrated by 3102 in FIG. 31 and identify patterns for predictive modeling; one or more user device 3010 may be used send user information, control SSR unit 3040, store user information, and the like;

SSR unit 3040 comprises a combination of hardware and programming instructions for performing subjective self-refraction (referring to, at least, FIGS. 1-19). It should be noted that, in some embodiments, measurement computer 3000 may be comprised completely or partially within SSR unit 3040.

In some embodiments, measurement computer 3000 may work without a digital image device 3001 and instead use any visual test object.

Figure 31:
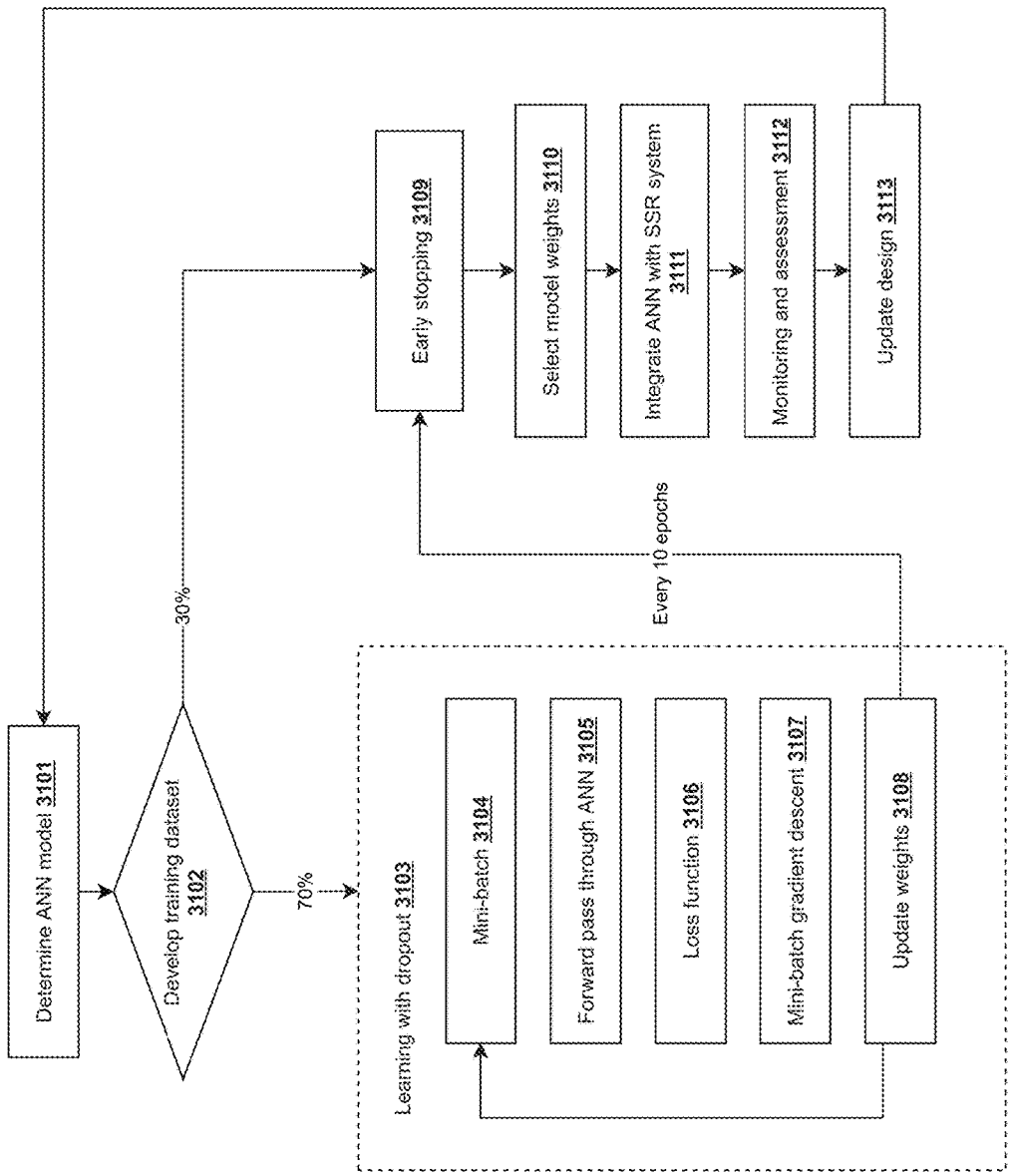
FIG. 31 is flow diagram illustrating a method for developing, training, implementing, and integrating an ANN with an SSR system, according to an embodiment of the invention.

FIG. 31 is flow diagram illustrating an exemplary development, training, validation, integration, use, and monitoring of an ANN with an SSR system. In this example, an ANN may be used, by FFNN predictor 3002 or RNN predictor 3003 to predict a starting or ending points for SSR. According to the embodiment, an FFNN may be used to predict a starting position of a plurality of spherical lenses, which may be motorized into the predicted position by an SSR system as embodied in FIG. 4 and FIG. 14. In a step 3101 an ANN model (e.g. FFNN, RNN, convolutional neural network, and the like) is chosen that is best suited to predict a desired eye measurement. Next in step 3102 training data is sourced from medical records, population studies, medical literature, and the like. Also, saved data that has accumulated on different users in database 3020 from prior uses of an SSR unit 3040, may be aggregated into predictive database 3021 in order to further build the training dataset. Development of this training dataset 3102, may invoke the process of feature selection and feature engineering. The training dataset may be further normalized or scaled in such a way that is best suitable for predicting eye measurement. Next, the training dataset may be partitioned into 70% for training the ANN and 30% for testing and early stopping. During the training or learning process 3103, dropout may be used. In step 3104, the partitioned 70% of the training dataset may be fed forward through the ANN in mini batches. Weights may be initialized randomly then updated following iterations (i.e. one mini-batch of data passing forward, in step 3105, then backwards through the ANN) using a backpropagation and gradient descent algorithm whereby the gradient of the loss function with respect to each weight in the ANN is calculated in step 3106. In this example mini-batch gradient descent may be used in step 3107. Weights may be updated (i.e. after each mini-batch is backpropagated through the ANN), in step 3108, using the following equation:

$$W' = W - \eta \frac{\partial E}{\partial W}$$

Where W is a particular weight within the ANN after a previous epoch, W' is the new updated weight after subtracting η ∂E/∂W, where η is the learning rate, ∂E/∂W is the partial derivative of the total error calculated from a pre-chosen loss function with respect to W.

In this particular embodiment the learning rate may be chosen or changed between epochs or an adaptive learning rate may be used, such as Adam [Kingma et al. "Adam: A Method for Stochastic Optimization." 2014.].

In this particular embodiment dropout is used, whereby some nodes are randomly excluded (i.e. their activation function is set to zero) during each iteration, so that when the ANN is used to predict eye measurements from unseen input data (i.e. independent variables of new users) the ANN will better predict the desired eye measurement because it generalizes more and did not simply memorize the training dataset.

According to the embodiment, early stopping may be used, in step 3109, and assessments after every 10 epochs are made, although any number of epochs may be used. By monitoring decreasing trend in error of the ANN on the test data or unseen data (i.e. top line on the graph) one may find the point at which the error on the test data starts to increase and diverge from the decreasing trend in error of the ANN on the training data (i.e. bottom line on the graph) and stop the training early to avoid having the ANN over fitting the training data. In a next step 3110, the weights are selected for the ANN.

After the ANN is developed it may be integrated with an SSR system in step 3111. One embodiment of how this integration may work is shown in FIG. 32.

While the integrated ANN and SSR system is being used to predict, measure and verify eye measurements, it may be monitored, in step 3112, and assessed for efficacy from time to time. In a next step 3113, updates may be made to the model and new ANNs developed. In a next step the process may iterate and begin again at step 3101. When iterating from step 3113 back to step 3101, the types of feature data used to train an ANN for predicting eye measurements may change. For example, instead of using numerical interval data (e.g. slant of palpebral fissure angle), numerical ratio data may be used instead (e.g. slant of palpebral fissure angle divided by length of palpebral fissure).

Figure 32:
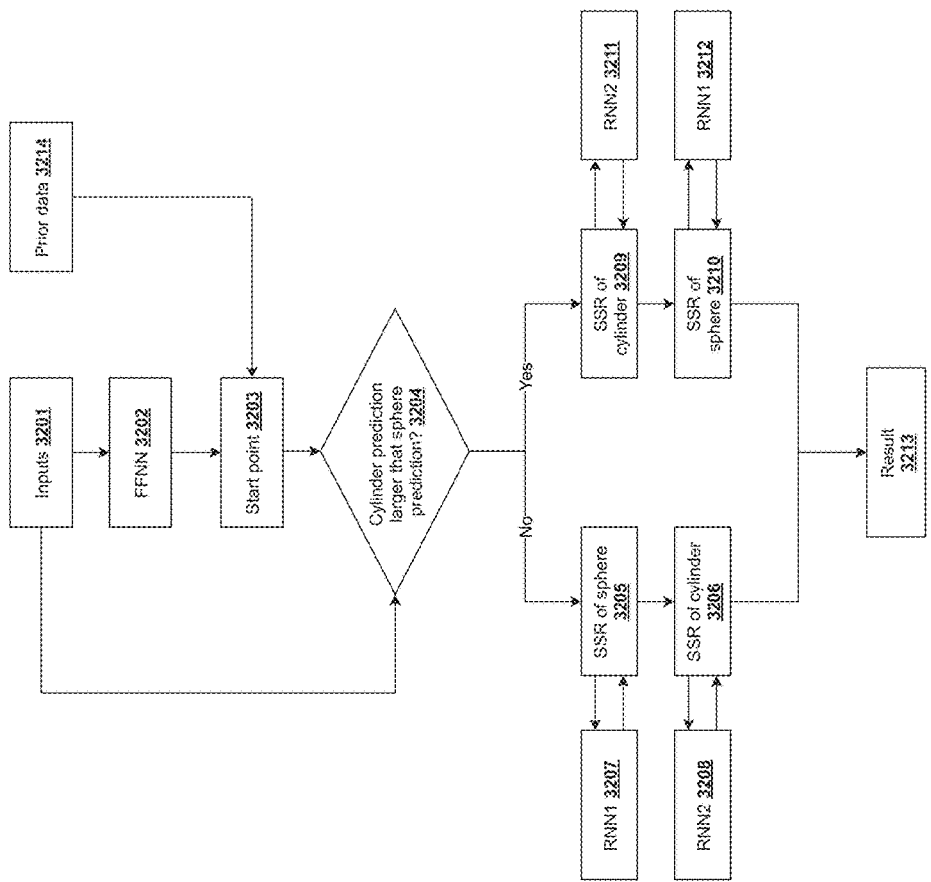
FIG. 32 is a flow chart describing one particular embodiment of how artificial neural networks may be integrated with an SSR system in accordance with some embodiments of the invention.

FIG. 32 is a flow chart describing one particular embodiment of how artificial neural networks may be integrated with an SSR unit 3040 in accordance with some embodiments of the invention. According to the embodiment, an example SSR unit 3040 with integrated ANNs is disclosed. In a first step 3201, a plurality of inputs, $X_1$ 3301 through $X_5$ 3305 may represent demographic and measurement data on a user. In a next step 3202 the plurality of inputs is computed by FFNN predictor 3002 to find a spherical start point for SSR that may be close to the user's best spherical component. In some embodiments, other data, from step 3214, such as prior lens prescriptions, lensometer results, autorefractor results, prior saved eye measurements, and the like, may be used as a sphere starting point (this data may be retrieved from a user profile), in step 3203, for SSR of a user's spherical component instead of utilizing an FFNN. For example, in some embodiments a user with eye measurements from an SSR process that are less than a month old, may be used at step 3203, rather than the FFNN. In additional embodiments, SSR unit 3040 may bypass or not require steps 3201 and 3202 if the user has recent eye measurements from subjective refraction. In such embodiments, SSR unit 3040 would use the recent subjective refraction measurements at step 3203. According to the embodiment, $X_5$ 3305 may represent a measurement such as a user's degree of palpebral fissure slant, which has been shown to correlate with higher magnitudes of astigmatism. [Garcia, L. M., Huang, D., Crowe, S., Traboulsi, E., (2003). Relationship between the axis and degree of high astigmatism and obliquity of palpebral fissure. *Journal of American Association for Pediatric Ophthalmology and Strabismus*, 7(1), 14-22.] Thus, $X_5$ 3305 may predict a large cylindrical component. The arrow from box 3201 to 3204 represents this mathematical prediction. This prediction may be made using a linear model, for example:

$$\text{predicted diopter cylindrical component} = \frac{2 \text{ diopters}}{\text{degrees}} |\text{slant angle}| + 0.2$$

wherein the absolute value of the slant angle measured in degrees is multiplied by 2 diopters per degree, next 0.2 is added to get the predicted diopter cylindrical component. Non-linear predictive models may also be used to predict a cylindrical component. More advanced predictive models using ANNs to predict cylindrical component may be used. For example an ANN with an input layer, may include other independent variables than degree of palpebral fissure slant, such as gender, or ratio of palpebral fissure slant to palpebral fissure length, and the like. The output from this particular ANN (i.e. the predicted diopter cylindrical component) may then be used at step 3204.

Step 3204 makes a decision to start SSR with either refraction of the spherical component or the cylindrical component. If the sphere is the main defect causing visual acuity loss, SSR starts with sphere refraction followed by cylinder refraction. If the cylinder is the main defect causing visual acuity loss (i.e. a relatively large cylindrical component is needed for correction) then the order of refraction is reversed as shown in FIG. 32. Example preprogramming of this decision tree may be as follows: in a next step 3204, if a predicted cylindrical component is, for example, less than 75% magnitude of the predicted spherical component, then SSR begins first with refracting the sphere, step 3205; if predicted cylindrical component is more than 75% magnitude of the predicted spherical component, then SSR begins with refraction of the cylinder, step 3206.

At step SSR of sphere 3205, SSR unit 3040 feeds sequential data (e.g. magnitude of diopter spherical changes $X_1$ 3401 and the rate of changes $X_2$ 3402) during an SSR process through RNN1 3207 (representing FIG. 34) and receives back a spherical prediction that SSR unit 3040 may use to advance the user through the SSR process faster. For example, a user may need spherical component of 6.00 D and the FFNN 3202 starts them at predicted 0.75 D, which is better than Plano, but even if the user sorts through the lenses in 0.25 D steps every 6 seconds, the user may take a while to reach the need 6.00 D spherical component for best vision. However, if for example the user is accelerating from 0.75 D to 2.5 D, the RNN1 may predict 4.75 D to SSR unit 3040 and the user skips nine 0.25 D steps in arriving at 6.00 D. In a next step SSR of cylinder 3206 a similar process takes place, whereby SSR unit 3040 feeds sequential data (e.g. magnitude of diopter cylindrical changes $X_1$ 3601 and the rate of changes $X_2$ 3602) during an SSR process through RNN2 3208 (representing FIG. 36) and receives back a spherical prediction that SSR unit 3040 may use to advance the user through the SSR process faster.

In a next step 3209, results comprising eye measurements are provided to a user and may be saved in cloud 3030 for future use.

Figure 33:
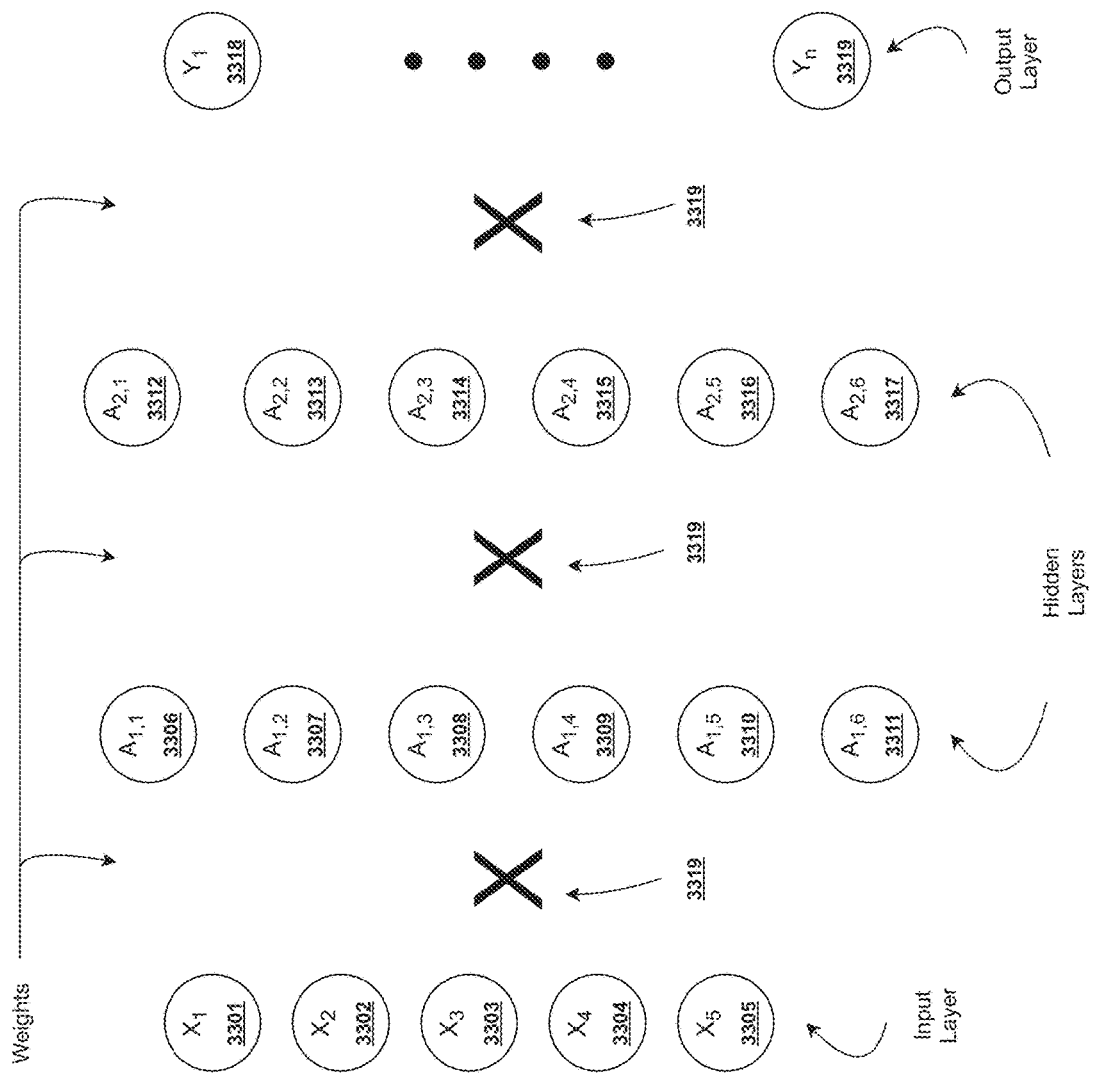
FIG. 33 is flow diagram illustrating a feed forward neural network (FFNN) that may be used to predict a user's best spherical component in accordance with some embodiments of the invention.

FIG. 33 is flow diagram illustrating a feed forward neural network (FFNN) that may be used to predict a user's best spherical component in accordance with some embodiments of the invention. This specific input layer contains five features, for example age ($X_1$ 3301), gender ($X_2$ 3302), height ($X_3$ 3303), palpebral fissure width ($X_4$ 3304), and slant of palpebral fissure ($X_5$ 3305). There are two hidden layers, each with six nodes. In a preferred embodiment, there may be 56 outputs ($y_1$ hat 3318 through $y_{56}$ hat 3319) representing all possible spherical component outputs for this particular embodiment, starting with minus 8.75 D sphere ($y_1$ hat 3318) to plus 5.00 D sphere ($y_{56}$ hat 3319), in 0.25 D increments and including a Plano lens. Each layer is fully connected as represented by 3319, however other embodiments may not have fully connected layers.

$X_2$ 3302 may be normalized to 0 for female or 1 for male. The StandardScaler equation:

$$x' = (x - \mu)/\sigma$$

may be used to normalize the other features (i.e. $X_1$ 3301 through $X_5$ 3305 not including $X_2$ 3302) because they follow a normal distribution. X' is the normalized value, x is the original value, μ is the mean of x, and σ is the standard deviation of x. This will assign a value from −1 to +1 for each input feature.

A sigmoid function may be used as the activation function A, at each node in the hidden layers $A_{1,1}$ 3306-$A_{1,6}$ 3311 and $A_{2,1}$ 3312-$A_{2,6}$ 3317. This will result in $y_1$ hat 3318 through $y_{56}$ hat 3319 receiving a value ranging from 0 to 1. When training the FFNN, the weights may be initialized with random numbers. After each training epoch, the values assigned to $y_1$ hat 3318 through $y_{56}$ hat 3319 will be compared to their corresponding targets $y_1$ through $y_{56}$ in order to calculate the loss function and update the weights during a backpropagation algorithm.

A set of training data, comprised of demographics and measurements (i.e. $X_1$ 3301 through $X_5$ 3305), from a plurality of users, along with each user's target spherical component, may be used to train the FFNN. The target spherical components of each user is assigned a value of 1, while all other spherical components that are known to not be the target are assigned a value of 0. For example, during a training epoch, a particular user's data will be fed forward through the FFNN. Each possible output from the FFNN ($y_1$ 3318 to $y_{56}$ 3319) corresponding to each spherical component (minus 8.75 D sphere through plus 5.00 D sphere) respectively, will be assigned a value from 0 to 1. If for example during a training epoch, the training data has a target spherical component of plus 2.00 D (representing $y_{40}$), then a value of 1 will be assigned to $y_{40}$ and a value of 0 to all other y's. When the y hat values are compared to their corresponding target y values, the weights will be optimized in such a way that after each epoch the y hat values match or come close to matching the target y values. In this example it would be ideal, that after many epochs, the FFNN has become sufficiently trained, whereby the $y_{40}$ hat was assigned an output of 1 (or nearly 1), while all other y hat outputs were given a value of 0 (or nearly 0). Ideally, once the FFNN is trained, the SSR processor would then be able to read the user's best spherical component, which is assigned an output value closest to one.

Figure 34:
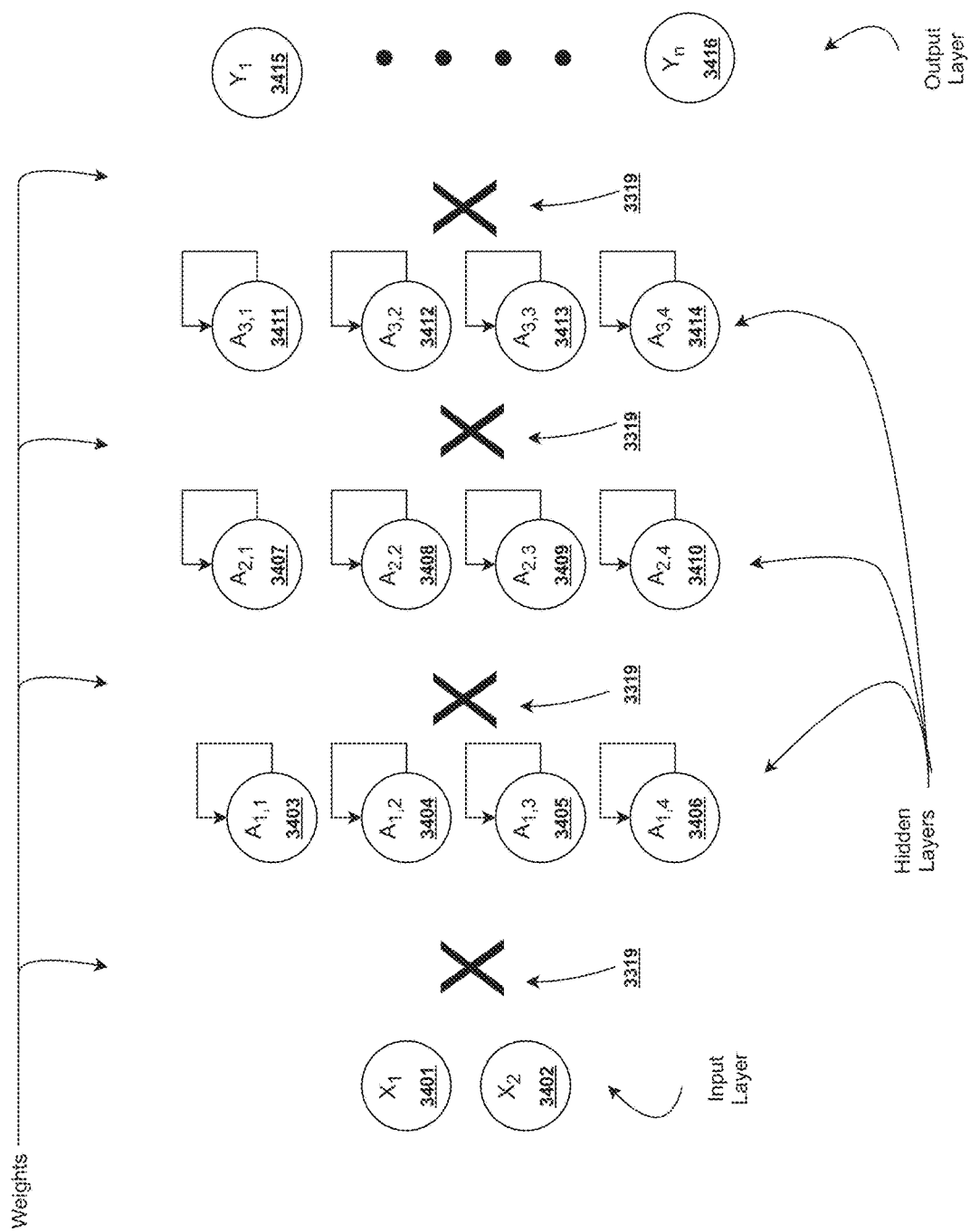
FIG. 34 is flow diagram illustrating a recurrent neural network (RNN) that may be used to find a user's best spherical component during an SSR process in accordance with some embodiments of the invention.

FIG. 34 is flow diagram illustrating a recurrent neural network 1 (RNN1) that may be used to find a user's best spherical component during an SSR process in accordance with some embodiments of the invention. According to the embodiment, an exemplary RNN1 process, by RNN predictor 3003, with two input features $X_1$ 3401 and $X_2$ 3402, three fully connected 3319 hidden layers $A_{1,1}$ 3403-$A_{1,4}$ 3406, $A_{2,1}$ 3407-$A_{2,4}$ 3410, and $A_{3,1}$ 3411-$A_{3,4}$ 3414, with 4 nodes in each layer, along with 56 outputs, $Y_1$ hat 3415 to $Y_{56}$ hat 3416 representing all possible spherical components in this particular embodiment is disclosed. $X_1$ 3401 may represent sequential changes in the spherical component, while $X_2$ 3402 may represent the sequence of time allotments to each change in spherical component.

RNNs are different from FFNNs in that time dependent sequential data may be passed through RNNs. At time zero ($t_0$), the first set of input data is fed forward through the network and at $t_1$, a second set of input data is fed forward through the network. Also, at $t_1$, the previous outputs from each node (the $t_0$ outputs), become an additional input at $t_1$. This process continues through time and depends on the length of the time dependent sequential data. In this way, earlier data in the time dependent sequential data, influences later outputs, via nodes in the hidden layers having memory of previously computed hidden state. While training the RNN, backpropagation through time is used to optimize the weights, in order for the RNN to provide more accurate outputs.

The RNN1 in FIG. 34 may be used to predict, by RNN1 predictor 3003, a user's best sphere component during SSR, before the user has found their best spherical component, while they are actively using an SSR system. The RNN1 may be designed so that after a certain predetermined number of time steps, the RNN1 finishes the sequence. The output sequence can then be read by the SSR processor, which then arranges a plurality of corrective lenses in such a way that the spherical component at the end of the output sequence is place in front of a user's eye.

FIG. 35 illustrates exemplary sequential vision measurement data (i.e. one row of training data within a training dataset for training an RNN) that may be fed forward through an RNN, such as RNN1 3207, 3805, and FIG. 34 in accordance with some embodiments of the invention. This data may be gathered from a database (for example, from database 3020, predictive database 3021, cloud service 3030, user device 3010, or the like). Some of this data may come from medical records, medical literature, or prior SSR sessions, wherein each user input during a prior SSR sessions has been saved directly on SSR unit 3040 or to the cloud 3030. This data may be compiled into a training dataset 3102 of FIG. 31 in order to train RNN1. According to the embodiment, an example of time dependent sequential data that may be used to train RNN1, by RNN predictor 3003. A sequence of spherical component changes and the time in milliseconds a user required to make the changes has been recorded previously. Note that during SSR, this particular user switched from minus 3.00 D to minus 3.25 D and then back to 3.00 D, before selecting 3.00 D. This reversal took longer than the other adjustments because the user's visual acuity is very similar at 0.25 D intervals in this range of minus spherical lenses. The longest sequence in the entire data set is 26 time-steps long. Thus, the shorter sequences are padded prior to being fed to the RNN. The output sequences may be of varying lengths.

User's with very severe refractive error will require more adjustments to reach their best spherical component. If for example, users of SSR never require more than 30 adjustments of the spherical component to reach their best spherical component, regardless of the severity of their refractive error, then 10 may be an optimum number of time-steps, before which the RNN finishes the sequence with a series of outputs. Those with minimal refractive error would find their best spherical component in 10 adjustments or less, while others may have their best spherical component approximated after 10 adjustments. In this way, the automation of vision measurements is more efficient and less time consuming.

Figure 36:
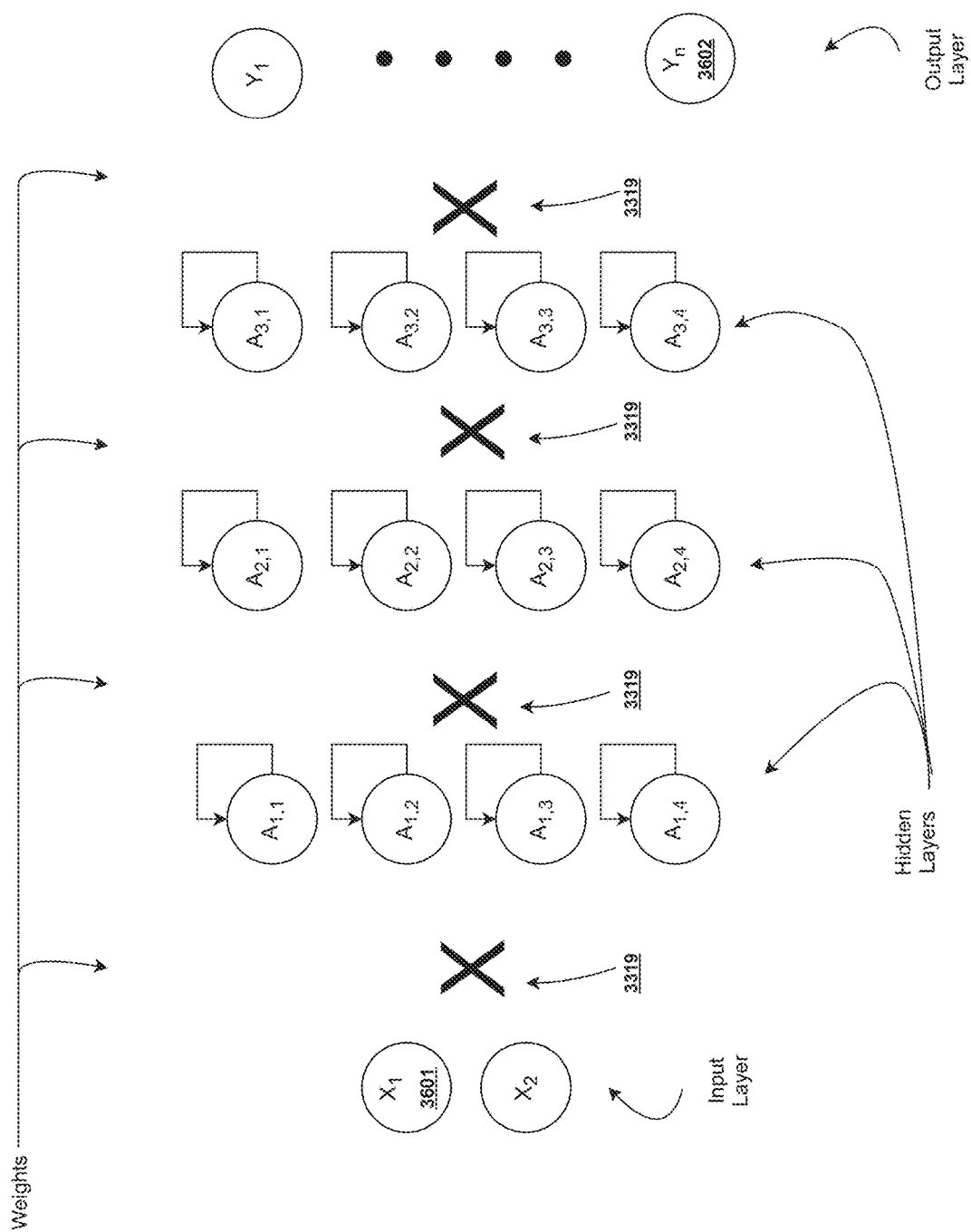
FIG. 36 is an RNN that may be used to find a user's best cylindrical component in accordance with some embodiments of the invention

FIG. 36 represents RNN2 that may be used to find a user's best cylindrical component in accordance with some embodiments of the invention. It is shaped similar to RNN1, however it is trained on cylindrical dataset. Thus, it is used to predict the cylindrical component during an SSR process. The parameters (i.e. weights and biases) will thus be different between RNN1 and RNN2. $X_1$ 3601 represents the sequential changes in cylindrical component and $X_2$ 3602 represents the time it takes the user to make the changes in cylindrical component. RNN2 has 16 possible outputs, that is $Y_1$ hat 3603 to Y16 hat 3604, representing a plano lens through minus 3.75 D cylindrical component in 0.25 D increments. This RNN may be trained and used similar to the RNN1 in FIG. 34.

It is important to understand that the ANNs used to calculate eye measurements are not limited to what is disclosed herein, but may include a plurality of types (e.g. RNN, convolutional artificial neural network, and the like), be designed with any plurality of inputs, outputs, layers, nodes, node types (e.g. LSTMs), activation functions, training algorithms, validation algorithms, and the like.

Figure 37:
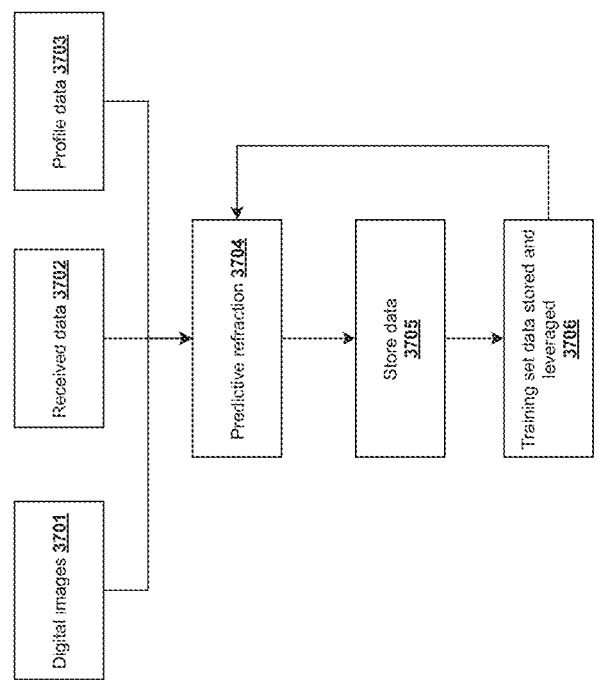
FIG. 37 illustrates a data flow diagram that demonstrates a method for data gathered for predictive refraction, according to an embodiment of the invention.

FIG. 37 illustrates a data flow diagram that demonstrates a method for gathering data for predictive refraction. In step 3701, an image of a user may be captured by a digital imaging device 3001 for predicting eye measurements during SSR. Digital imaging device 3001 may be located in a reception waiting area or it may be incorporated into a user device 3010 (for example, a smartphone, tablet, or the like). In other embodiments, the image may be received over network 2810. In step 3702, additional data may be received from a user interface 3005, for example from a cloud service 3030 via network 2810. In step 3703, other known data from prior office visits, for example profile data from user database 3020, cloud service 3030, or user device 3010 may also be incorporated into the predictive method. An example of profile data may be a patient's last known eyeglasses prescription. At least a portion of this data may be used for predicting a refraction in step 3704. An example of which is described in FIG. 32. There may be other predictive methods utilized in future predictive models.

In a next step 3705, patient data may be stored for future use following the data intake process (for example, to a user database 3020, a cloud service 3030, to a user device 3010, or the like). In a next step 3706, data may be stored, in predictive database 3021, and utilized to train future predictive models. As the data set grows, over time, predicative methods become more accurate. It is widely understood that AI, such as by use in ANN's, is able to identify patterns in data and utilize these patterns for application in predictive modeling. Therefore, it is beneficial to store patient data (for example, in cloud service 3030) as each user completes an SSR so that in turn, that data can be used to predict future refractive error, for example, returning to step 3704 to iterate, in other patients based on prior patient responses. Presbyopia is a condition where an eye's ability to focus on near objects gets worse and requires reading glasses. User data generated over many years from saved SSR sessions may be used to help predict reading glass strengths.

The dataflow method described herein may be paired with an office based refractive setting such as those utilized in traditional subjective refraction. It may be paired with an SSR process as described previously. The dataflow method may also be conducted with only a smartphone and a web-application. In this embodiment, an application, for example cloud service 3030, may be accessible by user devices 3010 through an on-line app store or a data subscription service offered to, for example, physicians' offices. As a subscription service, this method could be beneficial as a benchmark method against other subjective or objective refraction methods.

Figure 21:
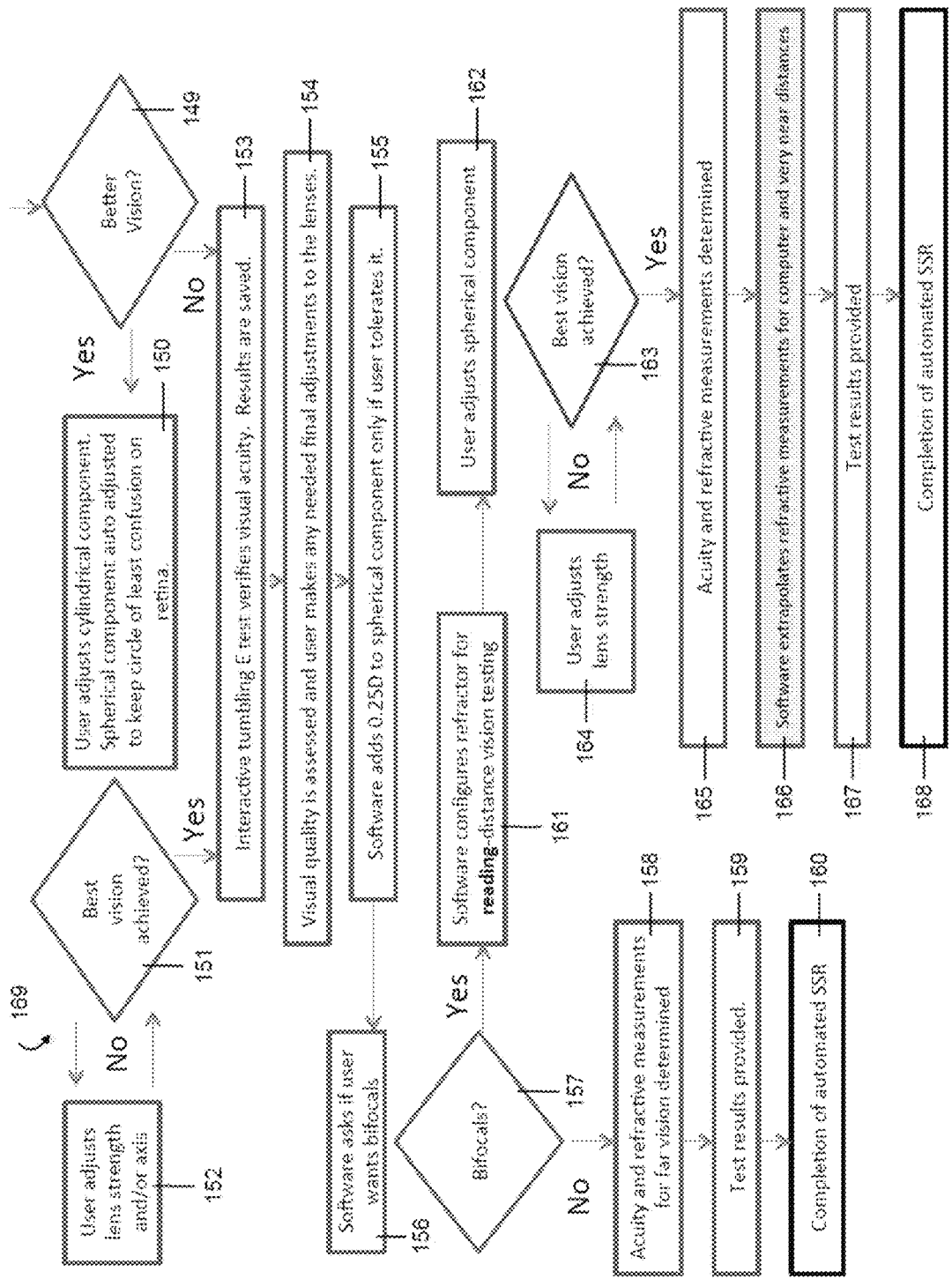
FIG. 21 is a continuation of FIG. 20 and illustrates a system for directing a user through a comprehensive SSR process in accordance with some embodiments of the invention.
Figure 38A:
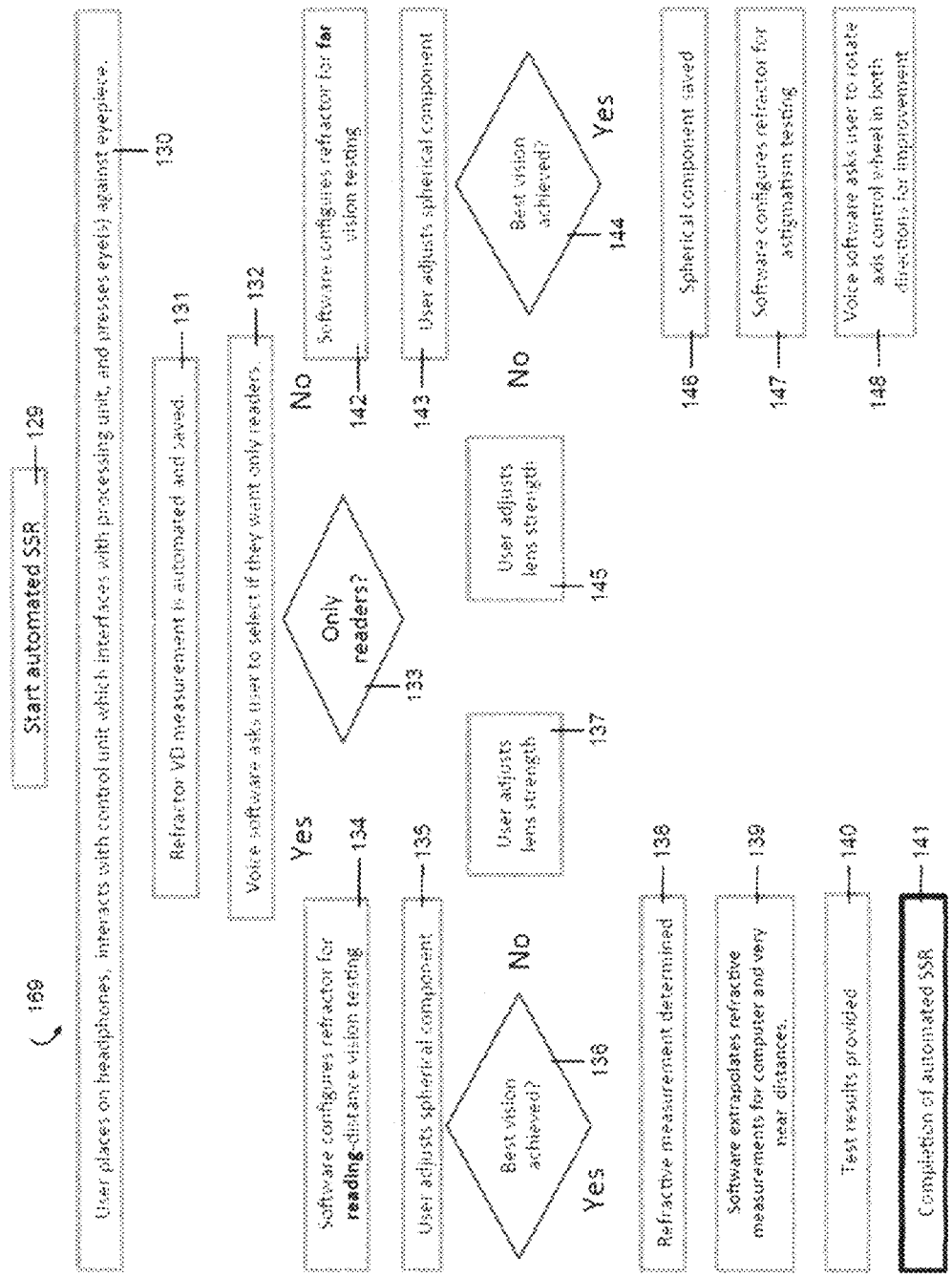
FIGS. 38A-B illustrate a method for SSR wherein ANNs may be used, according to a preferred embodiment of the invention.
Figure 38B:
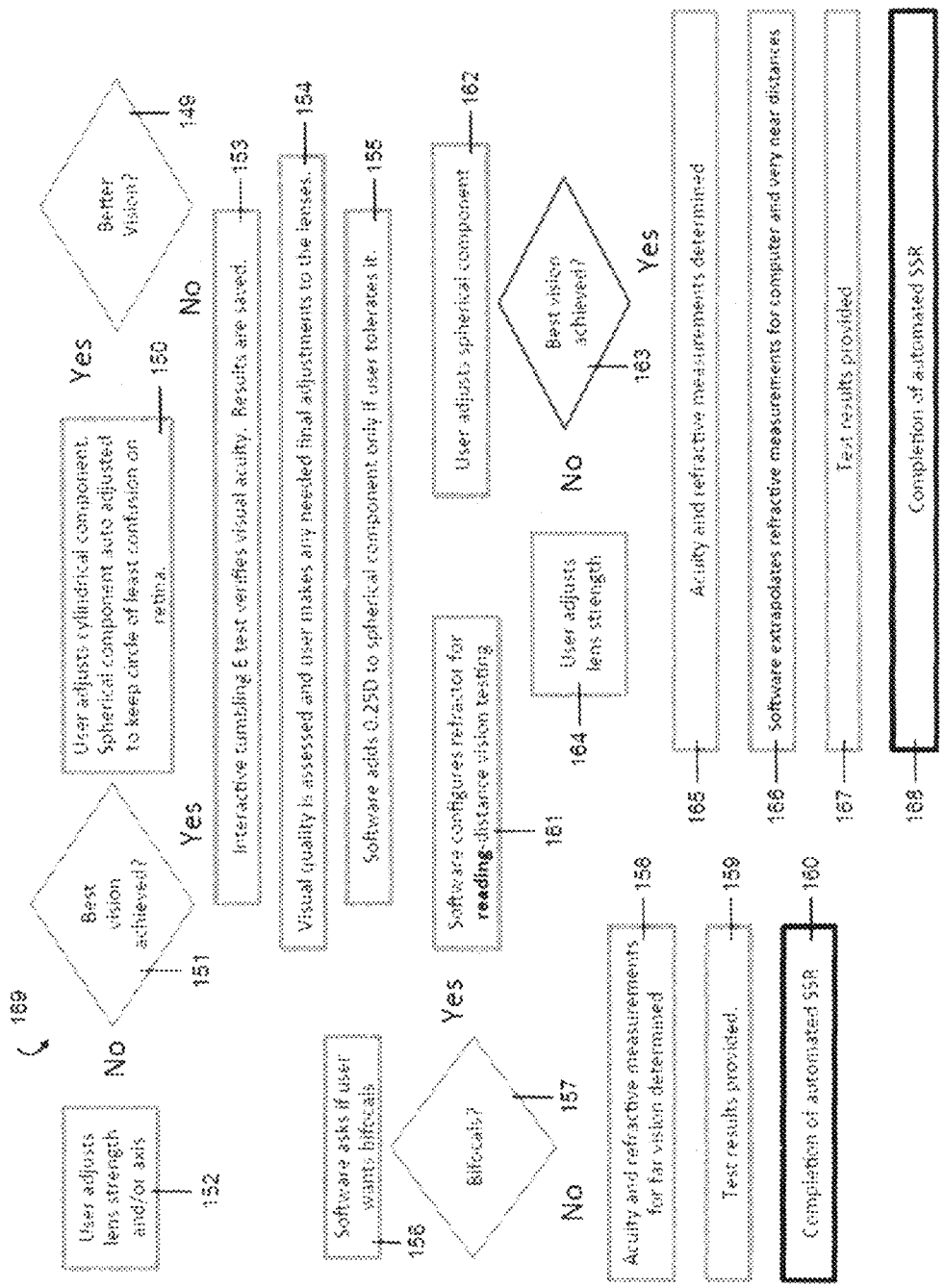

Table 1 lists a series of steps, a series of voice commands (for example as received by the user from output devices 2760, such as headphones 9), preprogramming, and an algorithmic process that may be used in accordance with an embodiment of the SSR process. Table 1 is further representative of a set of programmable instructions, that when executed by processor 43 (or processor 2710), takes a user through an SSR process. An SSR process may be further illustrated as seen in FIG. 20 and continued on FIG. 21, or as seen in FIG. 38. The algorithmic process described in Table 1 (i.e. 301-332), along with programming instructions, preprogramming of SSR unit 3040, and measurement computer 3000 as shown connected to cloud service 3030 in FIG. 30, together may perform a series of steps to guide a user through an SSR process. Additionally, ANNs that have been trained using the method of FIG. 31, may be integrated with an SSR unit 3040 (as shown in FIG. 32 and FIG. 38), may be used to make predictions throughout an SSR process. It should be understood that, in some embodiments, SSR unit 3040 may run algorithms from Table 1, without a need of ANNs. It should also be understood that eye measurements may be auto saved in a plurality of locations (e.g. in cloud 3030, user database 3020, predictive database 3021, locally on SSR unit 3040, or the like) after every eye measurement throughout the algorithms presented in Table 1.

TABLE 1

200 Instruction:
    Place the headphones over your ears and press the On/Off button. Adjust the
    volume on the controller as needed. Follow the voice commands to test your
    vision.
301 Stage 1 of Program Algorithm:
    After the user presses the on/off Button 68 on control unit 10, the user is taken to
    Voice Command Number 1.
201 Voice Command Number 1:
    Welcome to Vipassana, your partner in seeing things as they truly are. Now place
    the controller in your hands. Practice pressing the up and down buttons with your
    thumb. You will use these buttons to change the power of the lenses. Next, place
    your finger on the wheel of the controller and practice rotating it in both
    directions. You will use this wheel to change the axis of the lenses. Next, press
    the X button. You will use this button to change the type of lenses. Now let's get
    started. Slide the test switch on the controller to the other side.
302 Stage 2 of Program Algorithm:
    During Voice Command Number 1:
    In certain embodiments where ANNs are used, further instruction may be given to
    a user that directs them to enter feature data into SSR unit 3040. User video
    camera 11 along with SSR unit 3040 may be used to auto-match a user with their
    previous account using facial recognition software, as well as auto-capture feature
    data such as slant of palpebral fissure. This feature data is then fed through FFNN TABLE 1-continued 3202, 3801, FIG. 33 and a user's predicted final spherical component is provided to SSR unit 3040.
Sliding the Test Switch 69 to the other side after Voice Command Number 1 causes:
All 4 Disks 25, 27, 29, 31 to rotate in such a way that the center of each Plano lens FIG. 14 is centered on optical path 23 or 24 for the eye selected 21 or 22 depending on which eye label 75 or 78 the Test Switch 69 is resting over on Control Unit 10. In certain embodiments where ANNs are used, an SSR unit 3040 may place the predicted final spherical component from FFNN FIG. 33 in the appropriate optical path 23 or 24. Next, the user is taken to Voice Command Number 2.

202 Voice Command Number 2:
If you only want reading glasses without correcting for astigmatism press the X button. If not press the up button.

303 Stage 3 of Program Algorithm:
Pressing the X Button 67 after Voice Command Number 2 causes:
The SSR unit 3040 to set up for the Add 2 near vision test distance FIG. 9B (other embodiments may suffice for this stage of near vision testing as depicted in FIG. 13C). The appropriate eyepiece light 17 or 18 to flash for a few seconds depending on the position of Test Switch 69. The user is taken to Voice Command Number 20.
Pressing Up Button 71 is pressed after Voice Command Number 2 causes:
Each Plano lens to remain centered on the optical path 23 or 24 for the eye that was chosen by sliding Test Switch 69 during Voice Command Number 1. In certain embodiments where ANNs are used, the predicted final spherical component from Stage 2 of Program Algorithm will remain centered on the appropriate optical path 23 or 24. Next, the appropriate eyepiece light 17 or 18 will flash for a few seconds. Next, the user is taken to Voice Command Number 3.

203 Voice Command Number 3:
Look into the eyehole that is flashing.

304 Stage 4 of Program Algorithm:
After Voice Command Number 3 the user is taken to Voice Command Number 5.

204 Voice Command Number 4:
Now look into the other eyehole that is flashing.

305 Stage 5 of Program Algorithm:
After Voice Command Number 4 the user is taken to Voice Command Number 5.

205 Voice Command Number 5:
Make sure your eye is snug against the eyepiece. Close your other eye. Now focus on the lowest line that you can see. Try not to tilt your head left or right. Now start pressing the up button to see if it improves your vision.
You may press the down button to go in the other direction. Keep making adjustments until you can clearly see the direction each E is pointing on the lowest line that you can. Take your time.
After you find the lowest line you can read, press the X button.

306 Stage 6 of Program Algorithm:
During Voice Command Number 5:
Standardization of VD or auto-measurement of VD depending on the embodiment used (i.e. FIG. 18A, FIG. 18B or FIG. 18C) was performed. The Up and Down Buttons 71 and 73 will only cause -/+ 0.25 D changes respectively in the Spherical Component. In certain embodiments where ANNs are used, RNN1 3207, 3805 and FIG. 34, may be used to predict a final spherical component that SSR unit 3040 places in the appropriate optical path 23 or 24, which the user may further adjust if needed.
Pressing the X Button 67 after Voice Command Number 5 causes:
Optical element 4 on disk L-CYL FIG. 14 to be rotate into optical path 23 or 24 depending on which eye the Test Switch 69 has currently selected. Rotation of H-SPH Disk 25 and L-SPH Disk 27 in such a way that 0.25 D of convex (i.e. plus or converging) is added to the Spherical Component. This keeps the circle of least confusion on the retina, while testing for astigmatism. Next, the axis of optical element 4 on disk L-CYL FIG. 14 at this stage will start at 60 degrees during right eye refraction and 150 degrees during left eye refraction, according to FIG. 16. If needed Control Unit 10 will vibrate in order to assist the user in keeping the axis within a predetermined 210-degree arc in order to speed up the refraction process FIG. 16. Next, the user to be taken to Voice Command Number 6.

206 Voice Command Number 6:
Now use your finger to rotate the wheel on the controller in either direction. Stop where the E's on the lowest line you can see become most sharp. The controller will vibrate when you have gone too far in one direction, so you will need to start turning the wheel in the other direction. Stop at a place where the image is the sharpest.
If the image does not get sharper anywhere while turning the wheel fully in both directions, then push the X button.
If you can find a place on the wheel where the image is sharper, then leave the wheel in that position and press the up button.

307 Stage 7 of Program Algorithm:
Pressing the X button 67 after Voice command Number 6 (i.e. the user does not have astigmatism in the eye currently being tested) causes:
The Plano lens FIG. 14 on H-CYL Disk 29 and L-CYL Disk 31 to line up on optical path 23 or 24, depending on the eye selected on control unit 10. Next, H-

TABLE 1-continued

SPH Disk 25 and/or L-SPH Disk 27 are rotated in such a way that removes the convex (i.e. plus or converging) 0.25 D from the Spherical Component that was added in Stage 6 of Program Algorithm. Next, the user is taken to Voice Command Number 10 and SSR unit 3040 is set up for assessing visual quality (e g FIG. 12B or FIG. 13B) depending on the embodiment chosen.
Pressing the Up Button 71 after Voice Command Number 6 (i.e. user has astigmatism in the eye currently being tested) causes:
Changes in the Cylindrical Component by (-) 0.25 D, the axis remains unchanged and the user is taken to Voice Command Number 7.

207 Voice Command Number 7:
Keep pressing the up button to see if the image gets sharper. You can press the down button to go in the other direction. Keep pressing either the up or down button until you find where the E's are the sharpest on the lowest line you can read.
After finding the sharpest image with the up/down buttons, rotate the wheel again with your finger in either direction to see if you can make the E's on the lowest line you can read even sharper. When finished press the X button.

308 Stage 8 of Program Algorithm:
During Voice Command Number 7:
The Up/Down Buttons 71 and 73 cause -/+ 0.25 D incremental changes respectively in the cylindrical component. In certain embodiments where ANNs are used, RNN2 3208, 3808 and FIG. 36, may be used to further predict a final spherical component that SSR unit 3040 places in the appropriate optical path 23 or 24, which the user may further adjust if needed.
The cylindrical lenses are manipulated in such a way that the axis of the Cylindrical Component remains the same while adjusting the diopter strength of the Cylindrical Component with Up or Down Buttons 71 or 73.
Also, the cylindrical lenses are also manipulated in such a way that the diopter strength of the Cylindrical Component remains the same while adjusting the axis of the Cylindrical Component with Axis Control Wheel 70.
Also, during Voice Command Number 7, each -/+ 0.50 D change in the Cylindrical Component results in same-time automatic changes of the Spherical Component in such a way that keeps the circle of least confusion focused on the retina (i.e. maintaining the spherical equivalent). Taking into account that this particular embodiment uses the lens chamber depicted in FIG. 14, which has cylindrical lenses of only the concave (i.e. minus or diverging) variety, for the purpose of minimizing size and manufacturing costs, the following two examples show how SSR unit 3040 would process and auto-update the changes:
Example 1: If 0.5 D of concave (i.e. minus or diverging) Cylindrical Component is added, and the user has a convex (i.e. plus or converging) Spherical Component in front of the eye, then the SSR unit 3040 will add 0.25 D of convex Cylindrical Component.
Example 2: If 0.5 D of concave (i.e. minus or diverging) Cylindrical Component is added, and the user has a concave (i.e. minus or diverging) Spherical Component in front of the eye, then the SSR unit 3040 will remove 0.25 D of concave Cylindrical Component.
Pressing the X Button 67 after Voice Command Number 7 causes:
The user to be taken to Voice Command Number 10 and SSR unit 3040 sets up for assessing visual quality (e.g. FIG. 12B or FIG. 13B) depending on the embodiment chosen.

208 Voice Command Number 8:
Now use the Up and Down buttons to select the lowest line in which you can still see the direction that all the E's are pointing and then press the X button.

309 Stage 9 of Program Algorithm:
During Voice Command Number 8:
Each press of the Up or Down button 71 or 73 will cause a different line to be highlighted and pressing X Button 67 will select the highlighted line on Digital Acuity Chart 49. The other lines on Digital Acuity Chart 49 will disappear. A large E facing upwards will appear above the highlighted line as a reference. The user is then taken to Voice Command Number 9.

209 Voice Command Number 9:
Notice the large E that appears above the line you highlighted. Rotate the wheel with your finger to change the orientation of each E so that is matches the orientation of the large E on the screen. After orienting each E, use the Right button to go to the next E. You may use the Left button to go back. Press the X button when finished.

310 Stage 10 of Program Algorithm:
During Voice Command Number 9:
Each E will be selected one at a time with a cursor starting with the most left E, while the user is orienting the E. The user's visual acuity will be verified by orienting the E's to match the orientation of the large upward facing E on the screen as embodied in FIG. 25C, by using Axis Control Wheel 70. Pressing X Button 67 saves the visual acuity for that line along a percentage indicating the number of correctly oriented E's for that line. This information is displayed under the appropriate eye label FIG. 17 depending on the location of the Test Switch 69 and saved.
The user is then taken to Voice Command Number 30 if this is their first eye tested.
If this is their second eye tested and the user did not want bifocals when testing their first eye, they are taken to Voice Command Number 19.

TABLE 1-continued

If this is their second eye tested and the user wanted bifocals when testing their first eye, they are taken to Voice Command Number 22 and SSR unit 3040 is set up for Add 2 distance testing.

210 Voice Command Number 10
Now you will see the area around you. Focus on objects that are at least 20 feet away. Use the up and down buttons if any further adjustment is needed improve the quality of your vision. You may use the Left and Right buttons to rotate the device and look left or right. Press the X button when finished.

311 Stage 11 of Program Algorithm:
During Voice Command Number 10:
The Up and Down Buttons 71, 73 cause -/+ 0.25 D changes to the spherical component respectively. The Left and Right Buttons 74, 72 cause the apparatus to turn left and right respectively on a motorized swivel.
Pressing the X Button 67 at the end of Voice Command Number 10:
Takes the user to Voice Command Number 11 if the current eye being tested has astigmatism. If the current eye being tested was found to not have astigmatism during Voice Command Number 6, they are taken to Voice Command Number 12.

211 Voice Command Number 11
Now turn the wheel on the controller with your finger if needed to further improve the visual quality. When satisfied use the up and down buttons to make any further needed adjustments to your visual quality. When satisfied press the X button.

312 Stage 12 of Program Algorithm:
During Voice Command Number 11:
The control wheel 70 changes the cylindrical axis, while the up 71 and down 73 buttons change the strength of the Cylindrical Component.
Pressing the X Button 67 at the end of Voice Command Number 11:
Saves the cylindrical component and axis to Display Screen 77, FIG. 17. Next, the user is then taken to Voice Command Number 12

212 Voice Command Number 12:
You will now use the up and down buttons to go back and forth between two lenses.
Press the X button after finding the lens with the better quality of vision.
If you cannot find any difference between the two lenses, press the DOWN button one last time and then press the X button.

313 Stage 13 of Program Algorithm:
During Voice Command Number 12:
The starting Spherical Component at the start of Voice Command Number 12 is called "Z." During this stage the user will see if his/her refractive error will benefit from adding plus 0.25 D to Spherical Component "Z." This new Spherical Component will be called "Z plus 0.25." The Up and Down Buttons 71 and 73 will now only allow for changes between Spherical Components "Z" and "Z plus 0.25." For example, if Up Button 71 is pressed and "Z" is in the user's optical path 23 or 24, then no further plus 0.25 D removals from the Spherical Component will be made. If the user then presses Down Button 73, the Spherical Component will be changed to "Z plus 0.25" and further presses of the Down Button 73 will not cause any further additions of plus 0.25 D changes to the Spherical Component. This ensures that the final refractive measurement keeps the user's ciliary muscles relaxed as much as possible during accommodation. In some embodiments the user may keep being offered plus spherical changes in 0.25 D increments until the user's vision is worse. Then, SSR unit 3040 removes the last added plus 0.25 D sphere.
Pressing the X Button 67 after Voice Command Number 12:
Saves the Spherical Component and Cylindrical Component for optical infinity under the appropriate eye label on Display Screen 77, FIG. 17 depending on the position of the Test Switch 69. Then, SSR unit 3040 sets up for acuity verification testing FIG. 25A-C and the user is taken to Voice Command Number 8.

219 Voice Command Number 19:
If you would also like to measure your pupillary distance for better fitting of eyeglass frames press the X button. If not press the On/Off button.

320 Stage 20 of Program Algorithm:
Pressing the X Button 67 at the end of Voice Command Number 19 takes the user to Voice Command Number 28.
Pressing the On/Off Button 68 at the end of Voice Command Number 19 takes the user to Voice Command Number 27.

220 Voice Command Number 20:
Look into the eyehole that is flashing.

321 Stage 21 of Program Algorithm:
After Voice Command Number 20 the user is taken to Voice Command Number 22.

221 Voice Command Number 21:
Now look into the other eyehole that is flashing.

322 Stage 22 of Program Algorithm:
After Voice Command Number 21 the user is taken to Voice Command Number 22 if both eyes have not been tested yet at Add2 distance. If Add 2 distance testing is already completed for both eyes, and user has decided to test at Add 3 distance, but has not finished testing for both eyes, then user is taken to Voice Command Number 25. If user has completed Add 3 distance testing in both eyes TABLE 1-continued or decided to skip Add 3 distance testing, then the user is taken to Voice
Command Number 26.
- 222 Voice Command Number 22:
  Make sure your eye is snug against the eyepiece. Close your other eye. Now
  focus on the lowest line that you can see. Try not to tilt your head left or right.
  Now start pressing the up button to see if it improves your vision.
  You may press the down button to go in the other direction. Keep making
  adjustments until you can clearly see the direction each E is pointing on the
  lowest line that you can. Take your time.
  After you find the lowest line you can read, press the X button.
- 323 Stage 23 of Program Algorithm:
  During Voice Command Number 22:
  The Up and Down Buttons 71 and 73 make -/+ 0.25 D changes respectively to the
  Spherical Component during.
  Keeping the eye snug against the eyepiece will allow for standardization of the
  VD or auto-measurement depending on the embodiment used (i.e. FIG. 18A, FIG.
  18B or FIG. 18C). These measurements are saved for each eye by the SSR unit
  3040 for later access.
  Pressing the X Button 67 after Voice Command Number 22:
  Saves refractive measurements for Add 2 under the appropriate eye label on
  Display Screen 77, FIG. 17 based on whether this is the first or second eye tested.
  Causes the user to be taken to Voice Command Number 23 if they are still testing
  their first eye.
  If this was the user's second eye tested at the Add 2 distance and the user did not
  want testing at Add 3 and Add 1 distance for their first eye, then the user is taken
  to Voice Command Number 19.
  If this was the user's second eye tested at the Add 2 distance and the user already
  completed Add 3 and Add 1 distance testing on their first eye, then the SSR unit
  3040 is set up for Add 3 near vision test distance FIG. 9C (other embodiments
  may suffice for this stage of near vision testing as depicted in FIG. 13C for
  example). The user is then taken to Voice Command Number 25.
  If this was the user's second eye tested at the Add 2 distance and the user did not
  complete testing at Add 3 distance on their first eye, but did complete testing at
  Add 1 distance for their first eye, then the SSR unit 3040 is set up for Add 1 near
  vision test distance FIG. 9A (other embodiments may suffice for this stage of
  near vision testing as depicted in FIG. 13C for example). The user is then taken
  to Voice Command Number 26.
  If this was the user's second eye tested at the Add 2 distance and the user
  completed testing at Add 3 distance on their first eye, but did complete testing at
  Add 1 distance for their first eye, then the SSR unit 3040 is set up for Add 3 near
  vision test distance FIG. 9C (other embodiments may suffice for this stage of
  near vision testing as depicted in FIG. 13C for example). The user is then taken
  to Voice Command Number 25.
- 223 Voice Command Number 23:
  If you would like glasses for reading at computer monitor distance press the up
  button. If you do not want glasses for computer monitor distance press the X
  button.
- 324 Stage 24 of Program Algorithm:
  Pressing the Up Button 71 at the end of Voice Command Number 23:
  Removes 0.25 D of convex (i.e. plus or converging) from the Spherical
  Component and sets the SSR unit 3040 up for the Add 3 near vision test distance
  FIG. 9C (other embodiments may suffice for this stage of near vision testing as
  depicted in FIG. 13C for example). Causes the user to be taken to Voice
  Command Number 25.
  Pressing X Button 67 at the end of Voice Command Number 23:
  Takes the user to Voice Command Number 24.
- 224 Voice Command Number 24:
  If you would like glasses for very close work such as fly tying, sewing, or
  soldering press the down button. If you do not want glasses for very close work
  press the X Button.
- 325 Stage 25 of Program Algorithm:
  Pressing X Button 67 at the end Voice Command Number 24:
  Causes the SSR unit 3040 to configure to the Add 2 near vision test distance
  configuration FIG. 9B (other embodiments for near vision testing may be used as
  depicted in FIG. 13C). Next, the Add 2 Spherical Component found for the first
  eye is then aligned in the appropriate optical path 23 or 24 for testing the second
  eye. Next, appropriate eyepiece lights 17 or 18 for testing the second eye flash a
  few times and the user is taken to Voice Command Number 21. If the user has
  tested only one eye at optical infinity at this stage, then all eye measurements at
  this point are saved for the eye selected by Test Switch 69 and the user is taken to
  Voice Command Number 31.
  Pressing the Down button 73 at the end of Voice Command Number 24:
  Adds 0.25 D of convex (i.e. plus or converging) to the Spherical Component along
  the appropriate optical path 23 or 24 that the user is viewing. Next, SSR unit 3040
  sets up for Add 1 near vision test distance as embodied by FIG. 9A (other
  embodiments for near vision testing may be used as depicted in FIG. 13C) and
  takes the user to Voice Command Number 26.
- 225 Voice Command Number 25:
  Keep pressing the up button and down button as needed until you can read the
  print most clearly. When finished press the X button.

TABLE 1-continued

326 Stage 26 of Program Algorithm:
Pressing the X Button at the end of Voice Command Number 25:
Saves refractive measurements for Add 3 (i.e. computer reading distance) under
the appropriate eye label on Display Screen 77, FIG. 17 based on whether this
was the first or second eye tested. The user is then taken to Voice Command
Number 24 if this is their first eye being tested.
If this was the user's second eye being tested at Add 3 distance and the user did
not want Add 1 distance testing done on their first eye, then the user is taken to
Voice Command Number 19.
If this was the user's second eye being tested at Add 3 distance and the user's first
eye has already been tested at Add 1 distance, then the user is taken to Voice
Command Number 26.
226 Voice Command Number 26:
Keep pressing the down button and if needed the up button until you can read the
print most clearly. When finished press the X Button.
327 Stage 27 of Program Algorithm:
Pressing X Button 67 at the end of Voice Command Number 26:
Saves refractive measurements for Add 1 (i.e. soldering or fly tying) distance
under the appropriate eye label on the Display Screen 77, FIG. 17 based on
whether this is the first or second eye being tested. If the user has tested only one
eye at optical infinity at this stage, then all eye measurements at this point are
saved for the eye selected by Test Switch 69 and the user is taken to Voice
Command Number 31.
If this was the second eye tested at Add 1 distance, the user is taken to Voice
Command Number 19.
If not, the Spherical Component saved previously at the Add 2 distance for the
first eye, is placed in the appropriated optical path 23 or 24 in preparation for
testing of the second eye. The SSR unit 3040 then sets up to test the second eye at
Add 2 near vision test distance FIG. 9B (other embodiments may suffice for this
stage of near vision testing as depicted in FIG. 13C). The user is then taken to
Voice Command Number 21 and the other eyepiece light 17 or 18 for the second
eye starts flashing for a few seconds.
227 Voice Command Number 27:
Thank you for using Vipassana. Your eye measurements will print shortly.
328 Stage 28 of Program Algorithm:
Data on Display Screen 77, FIG. 17 are printed during Voice Command Number
27. The device then shuts off
228 Voice Command Number 28:
Place your forehead against the headrest and don't move it. Now close one eye.
You will use the Left and Right Buttons to move a needle so that it points to the
exact center of your pupil. Your pupil is the black circle in the center of your eye,
which is reflected in the mirror. When finished press the X button.
329 Stage 29 of Program Algorithm:
Pressing Left Button 74 during Voice Command Number 28 moves PD Needle
98 to the left via PD Motorized Ball Screw 96 riding on PD Ball Screw Guide
Rail 97. Pressing Right Button 72 moves PD Needle 98 in the other direction.
Pressing X Button 67 causes device to store the position of PD Needle 98 along
PD Ball Screw Guide Rail 97 for calculation of PD in Stage 30 of Program
Algorithm. The user is then taken to Voice Command Number 29.
229 Voice Command Number 29:
Now open your other eye and close the eye you just tested. Use the Left and Right
Buttons again to move the needle to the exact center of your pupil. When finished
press the X button.
330 Stage 30 of Program Algorithm:
Pressing X Button 67 at the end of Voice Command Number 29 causes Operating
Unit and Processor 43 to note the position of PD Needle 98 along the PD Ball
Screw Guide Rail 97 and calculate the distance in millimeters between this
current position and the stored positional data of PD Needle 98 from Stage 29 of
Program Algorithm. This number represents the user's PD, which is then
displayed on Display Screen 77, FIG. 17. The user is then they are taken to Voice
Command Number 27.
230 Voice Command Number 30:
If you want reading glasses or bifocals press the up button. If you do not want
reading glasses or bifocals press the move the test switch to the other side.
331 Stage 31 of Program Algorithm:
Pressing the Up Button 71 at the end of Voice Command Number 30:
Causes SSR unit 3040 to set up for Add 2 near vision test distance FIG. 9B and
takes the user to Voice Command Number 22.
Moving Test Switch 69 to the other eye at the end of Voice Command Number 30
causes:
The appropriate eyepiece light 17 or 18 to start flashing for a few seconds in order
to test the second eye. Optical disks FIG. 14 are rotated in such a way that the
Spherical Component currently in the user's optical path is moved to the other
optical path 23 or 24 to start testing the second eye. The optical disks FIG. 14 are
rotated in such that the user's second eye is tested starting at Plano for the
Cylindrical Component. All eye measurements up to this point have been saved
for the appropriate eye and displayed in their proper place FIG. 15. The user is
then taken to Voice Command Number 4.
231 Voice Command Number 31:
Move the test switch to the other side.

TABLE 1-continued

332 Stage 32 of Program Algorithm:
    Moving Test Switch 69 to the other eye at the end of Voice Command Number 31
    causes:
    The appropriate eyepiece light 17 or 18 to start flashing for a few seconds in order
    to test the user's second eye. The user is then taken to Voice Command Number
    4.

FIG. 38 illustrates an SSR process by SSR unit 3040 comprising a plurality of programming instructions outlined in Table 1. In a first step 3801, a trained FFNN (referring to FIG. 33), may receive input data from SSR unit 3040 and outputs a predicted spherical component to start SSR. In a next step 3802, SSR unit 3040 may send a request to an output device (for example, device 2907 or headphones 9) requesting a selection of reading glasses without correcting for astigmatism Table 1, 202, or not. If "yes" is received, in a next step 3815, SSR unit 3040 iteratively refracts a user's near vision (referring to Table 1: 202, 220-226, 303, 321-327), at any combination of three distances (e.g. Add1, Add2, Add3 as described by the algorithmic process in Table 1) based on a preference received from the user. During step 3815 a VD is measured, at step 3816, using any systems described in FIG. 18A-C. Once refraction of a first eye associated to the user is complete, they are looped back to step 3817 through the algorithm Table 1: 202, 220-226, 303, 321-327, to test a second eye associated with the user. After the second eye has been refracted at near distance, in a next step 3819 a PD is optionally measured and all eye measurements are saved (for example in user device 3010, to database 3020, in cloud service 3030, or any combination thereof) and provided in step 3820. Referring again to step 3802, if "no" is received, SSR unit 3040 refracts the spherical component at optical infinity in step 3803 using instructions from Table 1. Step 3803 further receives a VD measurement from step 3804 (using systems described in FIG. 18A-C). Further in step 3803 RNN1 3805 receives time sequential data from SSR unit 3040, to predict a spherical component that is used by SSR unit 3040 to update the spherical component along a user's appropriate optical path 23, 24. In a next step 3806, SSR unit 3040 instructs a user to operate axis control wheel 70 to adjust a cylindrical axis of in this embodiment 0.75 D in order to test if the user has astigmatism, without the need for a Jackson Cross Cylinder. If it is determined that the user has astigmatism, in a next step 3807 an axis and cylinder is further refracted by SSR unit 3040. Further in step 3807, RNN2 3808 receives time sequential data from SSR unit 3040, to predict a cylindrical component that is used by SSR unit 3040 to update the cylindrical component along a user's appropriate optical path 23, 24. In a next step 3809, SSR unit 3040 refines a user's sphere for visual quality. If a user has astigmatism, in a next step 3810, SSR unit 3040 refines the cylinder and axis for visual quality. After a user has had their visual quality assessed, in a next step 3811, SSR unit 3040 checks to see if the user will tolerate an extra plus 0.25 D spherical component to keep the ciliary muscle relaxed and avoid overminusing. In a next step 3812 SSR unit 3040 verifies the user's visual acuity (referring to FIG. 25A-C), using instructions described in Table 1: 208-209, 309-310. If this was the second eye tested at optical infinity and indication of "no" was received for bifocals (from step 3813 described below) when testing the first eye, in a next step 3819 a PD is optionally measured, and all eye measurements are saved (for example in user device 3010, to database 3020, in cloud service 3030, or any combination thereof) and provided in step 3820. If a user has verified only one eye for visual acuity, in a next step 3813, SSR unit 3040 sends a request to an output device to select if bifocals are desired. If "no" is received, the process loops to step 3803 to test the second eye. Otherwise if "yes" is received (referring again to step 3813), the process continues to step 3815 (as described previously). Once testing is complete for near vision at any combination of three distance (Add1, Add2, Add3 as described previously) the process loops back to step 3803 to test a second eye.

In some embodiments a user may be directed through the SSR process as shown in Table 1 and FIG. 38, but wherein ANNs and voice recognition software may be used with or without hand-held controller 10. In this configuration of SSR unit 3040, a user is directed through the SSR process by receiving audio instructions similar to what an eye care profession would say and the user responds verbally as they might in an eye clinic setting.

It is to be understood that the above description is intended to be illustrative and not restrictive. Therefore, the scope of the invention should be determined not with reference to the above description, but instead should be determined with reference to the appended claims along with full scope of their equivalents.

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for predicting eye measurements comprising:
an eye measurement prediction computer comprising a memory, a processor, and a plurality of programming instructions, the plurality of programming instructions stored in the memory that when executed by the processor cause the processor to:
receive feature data from one or more input devices;
determine one or more eye measurements using an artificial neural network previously trained using a plurality of previous eye measurements, the trained artificial neural network comprising a plurality of nodes, the nodes arranged in a plurality of layers, wherein:
a first subset of nodes, of the plurality of nodes, comprise an input layer, of the plurality of layers, the input layer comprising the feature data;
a second subset of nodes, of the plurality of nodes, comprising at least one hidden layer of the plurality of layers; and
a third subset of nodes, of the plurality of nodes, comprising an output layer of the plurality of layers, the output layer comprising the one or more eye measurements;

send the one or more eye measurements to one or more output devices;

wherein results from the input layer are passed to the at least one hidden layer;

wherein results from the at least one hidden layer is passed to the output layer;

wherein the input layer, the at least one hidden layer, and the output layer are connected sequentially in series by weights.

2. The system of claim 1, wherein one or more of the nodes process sequential time dependent data by memory of a previously computed hidden state.

3. A system for providing at least one automated eye measurement to a user comprising:

a plurality of prearranged corrective lenses, the plurality of corrective lenses operable to be arranged by a plurality of motors;

one or more input devices;

one or more output devices;

one or more visual test objects, the one or more visual test objects being a configurable distance from the corrective lenses;

an eye measurement prediction computer comprising a memory, a processor, and a plurality of programming instructions, the plurality of programming instructions stored in the memory that, when executed by the processor cause the processor to:

receive feature data from one or more input devices;

determine one or more eye measurements using an artificial neural network previously trained using a plurality of previous eye measurements, the trained artificial neural network comprising a plurality of nodes, the nodes arranged in a plurality of layers, wherein:

a first subset of nodes, of the plurality of nodes, comprise an input layer, of the plurality of layers, the input layer comprising the feature data;

a second subset of nodes, of the plurality of nodes, comprising at least one hidden layer of the plurality of layers; and a third subset of nodes, of the plurality of nodes, comprising an output layer of the plurality of layers, the output layer providing the one or more eye measurements;

arrange a start position for the plurality of corrective lenses based on the one or more eye measurements provided from the output layer;

wherein the input layer, the at least one hidden layer, and the output layer are connected sequentially in series by weights;

iteratively:

provide instructions to the one or more output devices;

receive input via the one or more input devices;

optionally change the configurable distance between the one or more visual test objects and the corrective lenses;

arrange, by the plurality of motors, at least one corrective lens, the arrangement based on the input;

receive a selection from the one or more input devices, the selection setting a final arrangement of one or more corrective lenses;

provide at least one eye measurement to the one or more output devices.

4. The system of claim 3, wherein one or more previously trained artificial neural networks each with a plurality of nodes capable of processing sequential time dependent data by memory of a previously computed hidden state, is used along-side the iteration to provide a position for the plurality of corrective lenses.

5. The system of claim 4, wherein the one or more input devices automatically capture biometric data to create a user profile or to match a preexisting user profile, associated with a user, the user associated with the biometric data.

6. The system of claim 5, wherein the user profile comprising, at least, one or more eye measurements, personal preferences, and prior purchase data is saved to the cloud.

7. The system of claim 6, wherein the eye measurement prediction computer decides to either use a most recent eye measurement from the user profile or the artificial neural network's predicted eye measurement for the start position of the plurality of corrective lenses.

8. The system of claim 7, wherein the plurality of corrective lenses is automatically arranged to keep a circle of least confusion focused on a retina associated with a user.

9. The system of claim 8, wherein at least a portion of the plurality of corrective lenses are cylindrical lenses wherein if the user has an axis of astigmatism, the axis is found without the use of a Jackson Cross Cylinder.

10. The system of claim 9, wherein the plurality of corrective lenses is arranged in order to successively add 0.25 diopter of convex to an eye measurement, further wherein a final eye measurement keeps a ciliary muscle, associated with a user, relaxed, without worsening a best vision associated with the user.

11. The system of claim 10, wherein the plurality of programming instructions when further executed by the processor cause the processor to:

iteratively:

provide instructions via the one or more output devices;

receive a response from the one or more input devices, the response based on the instructions and how they relate to the visual test object;

receive a final response from the one or more input devices, the final response associated with the visual test object;

provide a visual acuity measurement;

provide a measure of confidence of the visual acuity measurement based on a number of correct and incorrect responses regarding the visual test object.

12. The system of claim 11, wherein a vertex distance, associated with a user, is measured.

13. The system of claim 12, wherein a pupillary distance, associated with a user, is measured.

14. The system of claim 13, wherein a point of sale device captures biometric data to access a user profile.

15. The system of claim 14, wherein the user assesses their visual quality.

* * * * *